US011058761B2

(12) United States Patent
Mebatsion et al.

(10) Patent No.: US 11,058,761 B2
(45) Date of Patent: Jul. 13, 2021

(54) RECOMBINANT VECTORS EXPRESSING ANTIGENS OF AVIAN INFLUENZA VIRUS AND USES THEREOF

(71) Applicants: MERIAL INC., Duluth, GA (US); The United States of America, as represented by the Secretary of Agriculture, Washington, DC (US)

(72) Inventors: Teshome Mebatsion, Watkinsville, GA (US); Joyce Pritchard, Gainesville, GA (US); David Swayne, Athens, GA (US)

(*) Notice: Subject to any disclaimer, the term of this patent is extended or adjusted under 35 U.S.C. 154(b) by 379 days.

(21) Appl. No.: 15/789,936

(22) Filed: Oct. 20, 2017

(65) Prior Publication Data

US 2018/0110852 A1 Apr. 26, 2018

Related U.S. Application Data

(60) Provisional application No. 62/410,885, filed on Oct. 21, 2016.

(51) Int. Cl.
*A61K 39/145* (2006.01)
*C12N 7/00* (2006.01)
*A61K 39/00* (2006.01)

(52) U.S. Cl.
CPC .............. *A61K 39/145* (2013.01); *C12N 7/00* (2013.01); *A61K 2039/5256* (2013.01); *A61K 2039/552* (2013.01); *C12N 2710/16343* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| | | | | |
|---|---|---|---|---|
| 7,910,112 B2 | 3/2011 | Poulet | | |
| 8,394,384 B2 | 3/2013 | Guo | | |
| 8,592,558 B2 | 11/2013 | Vaughn | | |
| 2009/0081255 A1* | 3/2009 | Bublot | .................. | A61K 39/12 424/210.1 |
| 2018/0110852 A1* | 4/2018 | Mebatsion | ........... | A61K 39/145 |

FOREIGN PATENT DOCUMENTS

| | | | |
|---|---|---|---|
| CN | 101 780 275 A | | 7/2010 |
| WO | 2012/052835 A1 | | 4/2012 |
| WO | WO 2013/082327 | * | 6/2013 |

OTHER PUBLICATIONS

Hghihghi et al. "Characterization of Host Responses against a Recombinant Fowlpox Virus-Vectored Vaccine Expressing the Hemagglutinin Antigen of an Avian Influenza Virus", Clin. Vacc. Immunol., 2010; 17(3): 454-463.*

Alignment of SEQ ID 1 with Geneseq db No. BAM80487 by Smietank et al. in WO 2013043067 Mar. 2013.*

Alignment of SEQ ID 2 with Geneseq db No. AYK02224 by Bublot et al in US2010255029 Nov. 2010.*

Alignment of SEQ ID 15 with Geneseq db acc No. BBM34802 by BuBlot et al in USPgPub20140234358.*

Kapczynski et al. (Vaccine. 2015; 33: 1197-1205).*

Li et al. (Vaccine. 2011; 29: 8257-8266).*

Alignment of SEQ 2 with UniProt db access A0A0C5BAK0_9INFA submitted Apr. 2015.*

Alignment of SEQ ID 12 with Geneseq db acc No. ARW17904 Jul. 2008 by Poulet et al.*

Swayne et al. (Avain Diseases. 1997; 1: 910-922).*

Bertran et al., 2016, "Lack of chicken adaptation of newly emergent Eurasian H5N8 and reassortant H5N2 high pathogenicity avian influenza viruses in the US is consistent with restricted poultry outbreaks in the Pacific flyway during 2014-2015", Virology 494, 190-197.

Tong et al., 2013, PLoS Pathogens, vol. 9 (10), "New World Bats harbor diverse influenza A viruses".

Hoffmann, et al., 2005, "Role of specific hemagglutinin amino acids in the immunogenicity and protection of H5N1 influenza virus vaccines", PNAS, 102(36), p. 12915-12920.

Kapcynski, D.R., et al., Vaccine protection of chickens against antigenically diverse H5 highly pathogenic avian influenza isolates with a live HVT vector vaccine expressing the influenza hemagglutinin gene derived from a clade 2.2 avian influenza virus, Vaccine, vol. 33, Issue 9, Feb. 25, 2015, pp. 1197-1205.

International Search Report for related PCT application WO 2018/039511, dated Mar. 23, 2018.

* cited by examiner

*Primary Examiner* — Shanon A. Foley
(74) *Attorney, Agent, or Firm* — Suzanne Seavello Shope; John Ezcurra

(57) ABSTRACT

The present invention provides recombinant viral vectors that contain and express antigens of avian pathogens, compositions comprising the recombinant viral vectors, polyvalent vaccines comprising the recombinant viral vectors. The present invention further provides methods of vaccination against a variety of avian pathogens and method of producing the recombinant viral vectors.

22 Claims, 37 Drawing Sheets

Specification includes a Sequence Listing.

Figure 1A

| SEQ ID NO: | type | Gene Name |
|---|---|---|
| 1 | DNA | DNA encoding H5N2 HA in plasmid pHVTIG1SVLPC-HAsyn SbfI and pHVTIG1HHV3gBroSVLPC-HAsyn SbfI (rHVT501 and rHVT502) , codon-optimized |
| 2 | protein | H5N2 HA protein in rHVT501, rHVT502 and rHVT510 |
| 3 | DNA | DNA encoding mutant H5N2 HA in plasmid pHVTIG1SVMut-HAsyn SbfI (rHVT503) |
| 4 | protein | Mutant H5N2 HA protein in plasmid pHVTIG1SVLPC-HAsyn SbfI (rHVT503) |
| 5 | DNA | SV40 promoter |
| 6 | DNA | HHV3gB promoter |
| 7 | DNA | Synthetic Poly A |
| 8 | DNA | Nucleotide sequence of donor plasmid pHVTIG1SVLPC-HAsyn SbfI |
| 9 | DNA | Nucleotide sequence of donor plasmid pHVTIG1HHV3gBroSVLPC-HAsyn SbfI |
| 10 | DNA | Nucleotide sequence of donor plasmid pHVTIG1SVMut-HAsyn SbfI |
| 11 | DNA | Vaccinia H6 promoter |
| 12 | DNA | Nucleotide sequence of donor plasmid pF8 H6pLPC-HA H5N |
| 13 | DNA | Nucleotide sequence of donor plasmid pF8 H6p3Mut-HA H5N2 |
| 14 | protein | highly pathogenic HA cleavage site RERRRKR |
| 15 | protein | low pathogenic HA cleavage site RETR |
| 16 | DNA | mCMV promoter |
| 17 | DNA | DNA encoding mutant H5N2 HA in plasmid pCD046-H5N2 HA (rHVT510), wild-type |
| 18 | DNA | SV40 PolyA tail |
| 19 | DNA | Nucleotide sequence of donor plasmid pCD046-H5N2 HA |
| 20 | protein | H5N2 HA protein GenBank No. ALT19477 (A/wood/Oregon/ AH0007263/2015(H5N2)) with modified low pathogenic cleave site |
| 21 | protein | H5N2 HA protein GenBank No. ALT19381 (A/mallard/Idaho/ AH0007413/2015(H5N2)) with modified low pathogenic cleave site |
| 22 | protein | H5N2 HA protein GenBank No. AKH14518 (A/turkey/Minnesota/ 7172-1/2015(H5N2)) with modified low pathogenic cleave site |
| 23 | protein | H5N2 HA protein GenBank No. ALH21333 (A/chicken/Montana/ 15-010559-1/2015(H5N2)) with modified low pathogenic cleave site |
| 24 | protein | H5N2 HA protein GenBank No. ALT19525 (A/mallard/Oregon/ AH0003952/2015(H5N2)) with modified low pathogenic cleave site |
| 25 | protein | H5N2 HA protein GenBank No. AKN08877 (A/chicken/Iowa/ 14589-1/2015(H5N2)) with modified low pathogenic cleave site |

Figure 1B

| | | |
|---|---|---|
| 26 | protein | H5N2 HA protein GenBank No. AJS16153 (A/duck/EasternChina/S0131/2014(H5N2)) with modified low pathogenic cleave site |
| | | |
| 27 | protein | H5N2 HA protein GenBank No. ALP30284 (A/duck/Zhejiang/727041/2014(H5N2)) with modified low pathogenic cleave site |
| 28 | protein | H5N2 HA protein GenBank No. ALP30234 (A/chicken/Zhejiang/727079/2014(H5N2)) with modified low pathogenic cleave site |

Genome Structure of HVT and Insertion Sites

Genomic Structure of HVT, ORFs of the *BamHI* fragment,
and Insertion/Replacement Locations
(GenBank accession number for HVT FC126 sequence: AF291866.1)

donor plasmid pHVTIG1SVLPC-HAsyn SbfI

Dual Immunofluorescent staining of recombinant rHVT501 virus expressing LPC-HA H5N2 protein HVT Mab L78 – TRITC AIV H5N2 chicken anti-sera – FITC Schematic representation of primer binding sites LPC-HA H5N2
H5N2 LPC F.3
Syn Poly A tail
syntailR
MB081
IG1 Arm SV40 Promoter
SV40PromoterF
MB080
IG1 Arm pHVTIG1SVLPC-HAsyn SbfI PCR Identification
7227 bp rHVT501 identity PCR Lane 1: no template
Lane 2: HVT FC126
Lane 3: pHVTIG1SVLPC-HAsyn SbfI donor plasmid
Lane 4: rHVT501 donor plasmid pHVTIG1HHV3gBroSVLPC-HAsyn SbfI

Dual Immunofluorescent staining of recombinant vHVT502 virus expressing LPC-HA H5N2 protein HVT Mab L78 – TRITC AIV H5N2 chicken anti-sera – FITC Schematic representation of primer binding sites rHVT502 identity PCR Lane 1: no template
Lane 2: HVT FC126
Lane 3: pHVTIG1HHV3gBroSVLPC-HAsyn SbfI donor plasmid
Lane 4: vHVT502 donor plasmid pHVTIG1SVMut-HAsyn SbfI

Dual Immunofluorescent staining of recombinant vHVT503 virus expressing 3 Mut-HA H5N2 protein HVT Mab L78 – TRITC AIV H5N2 chicken anti-sera – FITC Schematic representation of primer binding sites 3 Mut-HA H5N2
H5N2 Mut F.3
Syn Poly A tail
syntailR
MB081
IG1 Arm SV40 Promoter
SV40PromoterF
MB080
IG1 Arm pHVTIG1SVMut-HAsyn SbfI PCR Identification
7227 bp rHVT503 identity PCR Lane 1: no template
Lane 2: HVT FC126
Lane 3: pHVTIG1SVMut-HAsyn SbfI donor plasmid
Lane 4: rHVT503 pCD046-H5N2 HA plasmid map

PCR amplification of rHVT510

Lane 1 : vHVT510 X+12
Lane 2: pCD046-COBRA-C
Lane 3: HVT Fc126
Lane 4: water

Lane 1 : vHVT510 X+12
Lane 2: pHVT IG1-SV-CobraC
Lane 3: HVT Fc126
Lane 4: water A schematic representation of the position of the F8 insertion site within the fowlpox virus (TROVAC) genome TROVAC *Sal*I Map Schematic representation of primer binding sites rFPV3003 identity PCR Cloning steps of Fowlpox donor plasmid pF8 H6p3Mut-HA H5N2

Schematic representation of primer binding sites

Fragment of pF8 H6p3Mut-HA H5N2 few primers
5062 bp (molecule 7635 bp)

rFPV3004 identity PCR

Expected Band sizes:
Parental Fowl pox=1511 bp
Recombinant virus=2048 bp rHVT-H5 virus shedding data - RNA copy number/10 ul Serology results – A/Turkey/Minnesota/12582/2015 (H5N2) challenge Serology results – A/Egypt/N04915/2014 (H5N1) challenge Viral shedding results – A/Turkey/Minnesota/12582/2015 (H5N2) challenge 1. rHVT501
2. rHVT510
3. sham Viral shedding results – A/Egypt/N04915/2014 (H5N1) challenge 1. rHVT501
2. rHVT510
3. sham

Figure 24A

```
                 1                                                 50
SEQ ID NO:2   (1) MEKIVLLFAVISLVKSDQICIGYHANNSTKQVDTIMEKNVTVTHAQDILE
SEQ ID NO:4   (1) MEKIVLLFAVISLVKSDQICIGYHANNSTKQVDTIMEKNVTVTHAQDILE

                 51                                               100
SEQ ID NO:2  (51) RTHNGKLCDLNGVKPLILKDCSVAGWLLGNPMCDEFIRVPEWSYIVERAN
SEQ ID NO:4  (51) RTHNGKLCDLNGVKPLILKDCSVAGWLLGNPMCDEFIRVPEWSYIVERAN

                 101                                              150
SEQ ID NO:2 (101) PANDLCYPGTLNDYEELKHLLSRINHFEKTLIIPRSSWPNHETSLGVSAA
SEQ ID NO:4 (101) PANDLCYPGTLNDYEELKHLLSRINHFEKTLIIPRNSWPNHETSLGVSAA

                 151                                              200
SEQ ID NO:2 (151) CPYQGASSFFRNVVWLIKKNDAYPTIKISYNNTNREDLLILWGIHHSNNA
SEQ ID NO:4 (151) CPYQGASSFFRNVVWLIKKNNAYPTIKISYNNTNREDLLILWGIHHSNNA

                 201                                              250
SEQ ID NO:2 (201) AEQTNLYKNPDTYVSVGTSTLNQRLVPKIATRSQVNGQSGRMDFFWTILK
SEQ ID NO:4 (201) AEQTNLYKNPDTYVSVGTSTLNQRLVPKIATRSQVNGQNGRMDFFWTILK

                 251                                              300
SEQ ID NO:2 (251) PNDAIHFESNGNFIAPEYAYKIVKKGDSTIMKSEMEYGHCNTKCQTPIGA
SEQ ID NO:4 (251) PNDAIHFESNGNFIAPEYAYKIVKKGDSTIMKSEMEYGHCNTKCQTPIGA

                 301                                              350
SEQ ID NO:2 (301) INSSMPFHNIHPLTIGECPKYVKSNKLVLATGLRNSPLRETRGLFGAIAG
SEQ ID NO:4 (301) INSSMPFHNIHPLTIGECPKYVKSNKLVLATGLRNSPLRETRGLFGAIAG

                 351                                              400
SEQ ID NO:2 (351) FIEGGWQGMVDGWYGYHHSNEQGSGYAADKESTQKAIDGVTNKVNSIIDK
SEQ ID NO:4 (351) FIEGGWQGMVDGWYGYHHSNEQGSGYAADKESTQKAIDGVTNKVNSIIDK

                 401                                              450
SEQ ID NO:2 (401) MNTQFEAVGREFNNLERRIENLNKKMEDGFLDVWTYNAELLVLMENERTL
SEQ ID NO:4 (401) MNTQFEAVGREFNNLERRIENLNKKMEDGFLDVWTYNAELLVLMENERTL

                 451                                              500
SEQ ID NO:2 (451) DFHDSNVKNLYDKVRLQLRDNAKELGNGCFEFYHKCDNECMESVRNGTYD
SEQ ID NO:4 (451) DFHDSNVKNLYDKVRLQLRDNAKELGNGCFEFYHKCDNECMESVRNGTYD

                 501                                              550
SEQ ID NO:2 (501) YPKYSEEAILKREEISGVKLESIGTYQILSIYSTVASSLALAIIVAGLSL
SEQ ID NO:4 (501) YPKYSEEAILKREEISGVKLESIGTYQILSIYSTVASSLALAIIVAGLSL

                 551          564
SEQ ID NO:2 (551) WMCSNGSLQCRICI
SEQ ID NO:4 (551) WMCSNGSLQCRICI
```

SEQ ID NO:2 v. SEQ ID NO:4: 99.3% identical

Figure 24B

```
                          1                                                50
SEQ ID NO:1      (1)   ATGGAAAAGATTGTGCTGCTGTTTGCTGTGATTAGCCTGGTGAAGTCAGA
SEQ ID NO:17     (1)   ATGGAGAAAATAGTGCTTCTTTTTGCAGTGATTAGCCTTGTTAAAAGTGA
SEQ ID NO:3      (1)   ATGGAAAAGATTGTGCTGCTGTTTGCTGTGATTTCCCTGGTGAAGTCCGA
                          51                                              100
SEQ ID NO:1     (51)   TCAGATTTGTATCGGTTACCATGCCAATAATTCTACTAAACAGGTGGATA
SEQ ID NO:17    (51)   TCAGATTTGCATTGGTTACCATGCAAACAACTCAACAAAGCAGGTTGACA
SEQ ID NO:3     (51)   CCAGATTTGTATTGGCTACCACGCTAATAACTCAACCAAACAGGTGGATA
                          101                                             150
SEQ ID NO:1    (101)   CAATTATGGAAAAGAACGTGACCGTGACACACGCTCAGGACATCCTGGAG
SEQ ID NO:17   (101)   CGATAATGGAGAAAAACGTCACTGTTACACATGCCCAAGACATACTGGAA
SEQ ID NO:3    (101)   CAATTATGGAAAAGAACGTGACCGTGACACACGCTCAGGACATCCTGGAG
                          151                                             200
SEQ ID NO:1    (151)   AGAACTCATAACGGGAAGCTGTGCGATCTGAATGGTGTGAAACCCCTGAT
SEQ ID NO:17   (151)   AGGACACACAACGGGAAGCTCTGCGATCTTAATGGAGTGAAACCCCTGAT
SEQ ID NO:3    (151)   AGAACTCATAACGGGAAGCTGTGCGATCTGAATGGTGTGAAACCCCTGAT
                          201                                             250
SEQ ID NO:1    (201)   CCTGAAGGACTGCTCTGTGGCAGGCTGGCTGCTGGGAAACCCCATGTGTG
SEQ ID NO:17   (201)   TCTAAAGGATTGTAGCGTAGCTGGGTGGCTCCTTGGAAATCCAATGTGCG
SEQ ID NO:3    (201)   CCTGAAGGACTGCTCAGTGGCAGGCTGGCTGCTGGGAAACCCCATGTGTG
                          251                                             300
SEQ ID NO:1    (251)   ATGAGTTCATCAGAGTGCCTGAATGGTCCTACATTGTGGAGAGGGCTAAC
SEQ ID NO:17   (251)   ACGAGTTCATCAGGGTACCGGAATGGTCTTACATCGTGGAGAGGGCTAAC
SEQ ID NO:3    (251)   ATGAGTTCATCAGAGTGCCTGAATGGTCCTACATTGTGGAGAGGGCTAAC
                          301                                             350
SEQ ID NO:1    (301)   CCTGCAAATGATCTGTGCTACCCAGGAACCCTGAACGACTATGAGGAACT
SEQ ID NO:17   (301)   CCAGCCAACGACCTCTGTTACCCAGGGACCCTCAATGACTATGAGGAACT
SEQ ID NO:3    (301)   CCTGCAAATGATCTGTGCTACCCAGGAACCCTGAACGACTATGAGGAACT
                          351                                             400
SEQ ID NO:1    (351)   GAAGCACCTGCTGAGCCGCATCAACCATTTCGAAAAGACACTGATCATCC
SEQ ID NO:17   (351)   GAAACACCTATTGAGCAGAATAAATCATTTTGAGAAAACTCTGATCATCC
SEQ ID NO:3    (351)   GAAGCACCTGCTGAGTCGCATCAACCATTTCGAAAAGACACTGATCATCC
                          401                                             450
SEQ ID NO:1    (401)   CCCGGAGCTCCTGGCCTAATCACGAGACTAGCCTGGGAGTGTCCGCAGCT
SEQ ID NO:17   (401)   CCAGGAGTTCTTGGCCCAATCATGAAACATCATTAGGGGTGAGCGCAGCA
SEQ ID NO:3    (401)   CCCGGAACAGCTGGCCTAATCACGAGACTTCACTGGGCGTGAGTGCCGCT
                          451                                             500
SEQ ID NO:1    (451)   TGTCCATACCAGGGAGCATCTTCATTCTTTCGCAACGTGGTGTGGCTGAT
SEQ ID NO:17   (451)   TGTCCATACCAGGGAGCATCCTCATTTTTCAGAAATGTGGTATGGCTCAT
SEQ ID NO:3    (451)   TGTCCATACCAGGGAGCAAGCTCCTTCTTTCGCAACGTGGTGTGGCTGAT
                          501                                             550
SEQ ID NO:1    (501)   CAAGAAAAATGATGCCTACCCCACCATCAAAATCTCATACAACAACACAA
SEQ ID NO:17   (501)   CAAAAAGAACGATGCATACCCGACAATAAAGATAAGCTACAATAATACCA
SEQ ID NO:3    (501)   CAAGAAAAACAATGCCTACCCCACCATCAAAATCTCCTACAACAACACAA
                          551                                             600
SEQ ID NO:1    (551)   ACCGGGAAGATCTTCTGATCCTGTGGGGCATCCACCATTCCAACAATGCA
SEQ ID NO:17   (551)   ATCGGGAAGATCTTTTGATACTGTGGGGGATTCATCATTCCAACAATGCA
SEQ ID NO:3    (551)   ATCGGGAAGATCTTCTGATCCTGTGGGGCATCCACCATTCTAACAATGCA
                          601                                             650
SEQ ID NO:1    (601)   GCCGAGCAGACTAACCTGTACAAAAATCCTGATACCTATGTGTCTGTGGG
SEQ ID NO:17   (601)   GCAGAGCAGACAAATCTCTATAAAAACCCAGACACTTATGTTTCCGTTGG
SEQ ID NO:3    (601)   GCCGAGCAGACTAACCTGTACAAAAATCCTGACACCTATGTGAGCGTGGG
```

Figure 24C

```
                                651                                            700
SEQ ID NO:1      (651)  GACTTCAACCCTGAACCAGCGCCTGGTGCCAAAGATCGCCACTCGGTCAC
SEQ ID NO:17     (651)  GACATCAACATTAAACCAGAGATTGGTGCCAAAAATAGCTACTAGATCCC
SEQ ID NO:3      (651)  GACTTCCACCCTGAACCAGCGCCTGGTGCCAAAGATCGCCACTCGGTCTC
                        701                                            750
SEQ ID NO:1      (701)  AAGTGAATGGGCAGAGTGGTCGCATGGATTTCTTTTGGACCATCCTGAAG
SEQ ID NO:17     (701)  AAGTAAACGGGCAGAGTGGAAGAATGGATTTCTTCTGGACAATTTTAAAA
SEQ ID NO:3      (701)  AGGTGAACGGGCAGAATGGTCGCATGGATTTCTTTTGGACCATCCTGAAG
                        751                                            800
SEQ ID NO:1      (751)  CCAAACGACGCTATTCACTTCGAAAGCAACGGCAATTTTATCGCCCCCGA
SEQ ID NO:17     (751)  CCGAATGATGCAATCCACTTTGAGAGTAATGGAAATTTCATTGCTCCAGA
SEQ ID NO:3      (751)  CCAAATGACGCTATTCACTTCGAATCCAACGGCAATTTTATCGCCCCCGA
                        801                                            850
SEQ ID NO:1      (801)  GTACGCTTATAAGATTGTGAAGAAAGGAGACAGTACCATCATGAAAAGCG
SEQ ID NO:17     (801)  ATATGCATACAAAATTGTCAAGAAAGGGGACTCAACAATTATGAAAAGTG
SEQ ID NO:3      (801)  GTACGCTTATAAGATTGTGAAGAAAGGAGACTCTACCATCATGAAATCAG
                        851                                            900
SEQ ID NO:1      (851)  AGATGGAATACGGGCACTGCAACACAAAGTGTCAGACTCCTATCGGTGCC
SEQ ID NO:17     (851)  AAATGGAGTATGGCCACTGCAACACCAAATGTCAAACTCCAATAGGGGCG
SEQ ID NO:3      (851)  AGATGGAATACGGGCACTGCAACACAAAGTGTCAGACTCCTATCGGTGCC
                        901                                            950
SEQ ID NO:1      (901)  ATTAACAGTAGCATGCCATTCCACAATATCCATCCCCTGACAATTGGGGA
SEQ ID NO:17     (901)  ATAAACTCTAGCATGCCATTCCACAATATACACCCTCTCACCATCGGGGA
SEQ ID NO:3      (901)  ATTAACTCTTCAATGCCATTCCACAATATCCATCCCCTGACAATTGGGGA
                        951                                           1000
SEQ ID NO:1      (951)  GTGCCCCAAGTATGTGAAATCTAACAAGCTGGTGCTGGCTACTGGTCTGA
SEQ ID NO:17     (951)  ATGCCCCAAATACGTGAAGTCAAACAAATTAGTCCTTGCGACTGGGCTCA
SEQ ID NO:3      (951)  GTGCCCCAAGTATGTGAAATCAAACAAGCTGGTGCTGGCTACTGGTCTGA
                        1001                                          1050
SEQ ID NO:1     (1001)  GAAACAGCCCCCTGAGAGAGACCCGGGGCCTGTTTGGAGCAATTGCTGGG
SEQ ID NO:17    (1001)  GAAATAGTCCTCTAAGAGAAACGAGAGGACTATTTGGAGCTATAGCAGGG
SEQ ID NO:3     (1001)  GGAATAGTCCTCTGCGCGAAACCCGGGGCCTGTTTGGAGCAATTGCTGGT
                        1051                                          1100
SEQ ID NO:1     (1051)  TTTATTGAGGGCGGATGGCAGGGTATGGTGGATGGGTGGTACGGTTATCA
SEQ ID NO:17    (1051)  TTTATAGAGGGAGGATGGCAGGGAATGGTAGACGGTTGGTATGGGTATCA
SEQ ID NO:3     (1051)  TTTATTGAGGGCGGATGGCAGGGTATGGTGGATGGGTGGTACGGTTATCA
                        1101                                          1150
SEQ ID NO:1     (1101)  CCATTCCAACGAACAGGGGTCTGGTTACGCTGCAGATAAAGAGTCCACAC
SEQ ID NO:17    (1101)  TCATAGCAATGAGCAGGGGAGTGGGTACGCTGCAGACAAAGAATCAACCC
SEQ ID NO:3     (1101)  CCATAGTAACGAACAGGGGAGCGGTTACGCTGCAGATAAAGAGTCTACAC
                        1151                                          1200
SEQ ID NO:1     (1151)  AGAAGGCTATTGACGGAGTGACTAACAAAGTGAACAGCATCATTGACAAG
SEQ ID NO:17    (1151)  AAAAGGCAATAGATGGAGTTACCAATAAGGTCAACTCAATCATTGACAAA
SEQ ID NO:3     (1151)  AGAAGGCTATTGACGGAGTGACTAACAAAGTGAACAGCATCATTGACAAG
                        1201                                          1250
SEQ ID NO:1     (1201)  ATGAATACTCAGTTCGAGGCAGTGGGGAGAGAATTTAACAATCTGGAGAG
SEQ ID NO:17    (1201)  ATGAACACTCAATTTGAGGCCGTTGGAAGGGAATTTAATAACTTAGAAAG
SEQ ID NO:3     (1201)  ATGAACACTCAGTTCGAGGCAGTGGGGAGAGAATTTAACAATCTGGAGAG
                        1251                                          1300
SEQ ID NO:1     (1251)  AAGGATCGAAAACCTGAATAAGAAAATGGAAGATGGCTTCCTGGACGTGT
SEQ ID NO:17    (1251)  GAGAATAGAGAATTTAAACAAGAAAATGGAAGACGGATTCCTAGATGTCT
SEQ ID NO:3     (1251)  AAGGATCGAAAACCTGAATAAGAAAATGGAAGATGGCTTCCTGGACGTGT
```

Figure 24D

```
                       1301                                             1350
SEQ ID NO:1   (1301)  GGACCTACAACGCAGAGCTGCTGGTGCTGATGGAGAATGAAAGGACACTG
SEQ ID NO:17  (1301)  GGACTTATAATGCTGAACTTTAGTTCTCATGGAAAATGAGAGAACTCTA
SEQ ID NO:3   (1301)  GGACCTACAACGCAGAGCTGCTGGTGCTGATGGAGAATGAAAGGACACTG
                       1351                                             1400
SEQ ID NO:1   (1351)  GATTTTCACGACAGCAACGTGAAAAATCTGTATGATAAAGTGAGACTGCA
SEQ ID NO:17  (1351)  GATTTCCATGACTCAAATGTCAAGAACCTTTACGACAAAGTCCGACTACA
SEQ ID NO:3   (1351)  GATTTTCACGACAGCAACGTGAAAAATCTGTATGATAAAGTGAGACTGCA
                       1401                                             1450
SEQ ID NO:1   (1401)  GCTGAGGGACAACGCTAAAGAACTGGGCAATGGATGTTTCGAGTTTTACC
SEQ ID NO:17  (1401)  GCTTAGGGATAATGCAAAGGAGCTGGGTAATGGTTGTTTCGAGTTCTATC
SEQ ID NO:3   (1401)  GCTGAGGGACAACGCTAAAGAACTGGGCAATGGATGTTTCGAGTTTTACC
                       1451                                             1500
SEQ ID NO:1   (1451)  ATAAGTGCGATAACGAGTGTATGGAAAGTGTGAGAAATGGCACATACGAC
SEQ ID NO:17  (1451)  ATAAATGTGATAACGAATGTATGGAGAGCGTAAGAAATGGGACGTATGAC
SEQ ID NO:3   (1451)  ATAAGTGCGATAACGAGTGTATGGAAAGCGTGAGAAATGGCACATACGAC
                       1501                                             1550
SEQ ID NO:1   (1501)  TATCCAAAATATAGCGAGGAAGCAATCCTGAAGAGGGAGGAAATTAGCGG
SEQ ID NO:17  (1501)  TACCCTAAGTATTCAGAAGAAGCAATATTAAAAAGAGAAGAAATAAGCGG
SEQ ID NO:3   (1501)  TATCCAAAATATTCCGAGGAAGCAATCCTGAAGAGGGAGGAAATTTCCGG
                       1551                                             1600
SEQ ID NO:1   (1551)  CGTGAAACTGGAGTCCATCGGAACCTACCAGATCCTGTCAATTTATAGTA
SEQ ID NO:17  (1551)  AGTGAAATTAGAATCAATAGGAACTTACCAGATACTGTCAATTTATTCAA
SEQ ID NO:3   (1551)  CGTGAAACTGGAGTCTATCGGAACCTACCAGATCCTGTCCATTTATTCTA
                       1601                                             1650
SEQ ID NO:1   (1601)  CAGTGGCCTCCTCTCTGGCACTGGCCATCATTGTGGCTGGGCTGTCTCTG
SEQ ID NO:17  (1601)  CAGTGGCGAGTTCCCTAGCACTGGCAATCATAGTGGCTGGTCTATCTTTA
SEQ ID NO:3   (1601)  CAGTGGCCAGTAGCCTGGCACTGGCCATCATTGTGGCTGGTCTGTCTCTG
                       1651                                   1692
SEQ ID NO:1   (1651)  TGGATGTGTAGTAACGGGAGTCTGCAGTGTAGGATTTGTATC
SEQ ID NO:17  (1651)  TGGATGTGCTCTAATGGTCGTTACAATGCAGAATTTGCATC
SEQ ID NO:3   (1651)  TGGATGTGTTCAAACGGTAGTCTGCAGTGTAGAATCTGTATC
```

Sequence identity percentage (%)

| SEQ ID NO: | 1 | 3 | 17 |
|---|---|---|---|
| 1 | | 94.4 | 76.8 |
| 3 | | | 76.9 |
| 17 | | | |

Figure 24E

```
                        1                                                50
SEQ ID NO:2     (1)   MEKIVLLFAVISLVKSDQICIGYHANNSTKQVDTIMEKNVTVTHAQDILE
SEQ ID NO:4     (1)   MEKIVLLFAVISLVKSDQICIGYHANNSTKQVDTIMEKNVTVTHAQDILE
SEQ ID NO:23    (1)   MEKIVLLFAVVNLVKSDQICIGYHANNSTKQVDTIMEKNVTVTHAQDILE
SEQ ID NO:24    (1)   MEKIVLLFAVVSLVKSDQICIGYHANNSTKQVDTIMEKNVTVTHAQDILE
SEQ ID NO:26    (1)   MEKIVLLLAIVSLVKSDQICIGYHANNSTKQVDTIMEKNVTVTHAQDILE
SEQ ID NO:27    (1)   MEKIVLLLAVVSLVKSDQICIGYHANNSTEQVDTIMEKNVTVTHAQDILE
SEQ ID NO:28    (1)   MEKIVLLLAVVSLVKSDQICIGYHANNSTEQVDTIMEKNVTVTHAQDILE
SEQ ID NO:25    (1)   MEKIVLPFAVISLVKSDQICIGYHANNSTKQVDTIMEKNVTVTHAQDILE
SEQ ID NO:20    (1)   MEKIVLLFAVISLVKSDQICIGYHANNSTKQVDTIMEKNVTVTHAQDILE
SEQ ID NO:21    (1)   MEKIVLLFAVISLVKSDQICIGYHANNSTKQVDTIMEKNVTVTHAQDILE
SEQ ID NO:22    (1)   MEEIVLLFAVISLVKSDQICIGYHANNSTKQVDTIMEKNVTVTHAQDILE
                        51                                              100
SEQ ID NO:2     (51)  RTHNGKLCDLNGVKPLIILKDCSVAGWLLGNPMCDEFIRVPEWSYIVERAN
SEQ ID NO:4     (51)  RTHNGKLCDLNGVKPLIILKDCSVAGWLLGNPMCDEFIRVPEWSYIVERAN
SEQ ID NO:23    (51)  KTHNGKLCDLNGVKPLIILKDCSVAGWLLGNPMCDEFIRVPEWSYIVERAN
SEQ ID NO:24    (51)  KTHNGKLCDLNGVKPLIILKDCSVAGWLLGNPMCDEFIRVPEWSYIVERAN
SEQ ID NO:26    (51)  KTHNGKLCDLNGVKPLIILKDCSVAGWLLGNPMCDEFIRVPEWSYIVERAN
SEQ ID NO:27    (51)  KTHNGKLCDLNGVKPLIILKDCSVAGWLLGNPMCDEFIRVPEWSYIVERAN
SEQ ID NO:28    (51)  KTHNGKLCDLNGVKPLIILKDCSVAGWLLGNPMCDEFIRVPEWSYIVERAN
SEQ ID NO:25    (51)  KTHNGKLCDLNGVKPLIILKDCSVAGWLLGNPICDEFIRVPEWSYIVERAN
SEQ ID NO:20    (51)  KTHNGKLCDLNGVKPLIILKDCSVAGWLLGNPMCDEFIRIPEWSYIVERAN
SEQ ID NO:21    (51)  KTHNGKLCDLNGVKPLIILKDCSVAGWLLGNPMCDEFIRVPEWSYIVERAN
SEQ ID NO:22    (51)  KTHNGKLCDLNGVKPLIILKDCSVAGWLLGNPMCDEFIRVPEWSYIVERAN
                        101                                             150
SEQ ID NO:2     (101) PANDLCYPGTLNDYEELKHLLSRINHFEKTLIIPRSSWPNHETSLGVSAA
SEQ ID NO:4     (101) PANDLCYPGTLNDYEELKHLLSRINHFEKTLIIPRNSWPNHETSLGVSAA
SEQ ID NO:23    (101) PANDLCYPGTLNDYEELKHLLSRINHFEKTLIIPRSSWPNHETSLGVSAA
SEQ ID NO:24    (101) PANDLCYPGTLNDYEELKHLLSRINHFEKTLIIPRSSWPNHETSLGVSAA
SEQ ID NO:26    (101) PANDLCYPGTLNDYEELKHLLSRINHFEKTLIIPKSSWPNHETSLGVSAA
SEQ ID NO:27    (101) PANDLCYPGNLNDYEELKHLLSRINHFEKTLIIPKSSWPNHETSLGVSAA
SEQ ID NO:28    (101) PANDLCYPGNLNDYEELKHLLSRINHFEKTLIIPKSSWPNHETSLGVSAA
SEQ ID NO:25    (101) PANDLCYPGTLNDYEELKHLLSRINHFEKTLIIPRSSWPNHETSLGVSAA
SEQ ID NO:20    (101) PANDLCYPGTLNDYEELKHLLSRINHFEKTLIIPRSSWPNHETSLGVSAA
SEQ ID NO:21    (101) PANDLCYPGTLNDYEELKHLLSRINHFEKTLIIPRSSWPNHETSLGVSAA
SEQ ID NO:22    (101) PANDLCYPGTLNDYEELKHLLSRINHFEKTLIIPRSSWPNHETSLGVSAA
                        151                                             200
SEQ ID NO:2     (151) CPYQGASSFFRNVVWLIKKNDAYPTIKISYNNTNREDLLILWGIHHSNNA
SEQ ID NO:4     (151) CPYQGASSFFRNVVWLIKKNNAYPTIKISYNNTNREDLLILWGIHHSNNA
SEQ ID NO:23    (151) CPYQGASSFFRNVVWLIKKNDAYPTIKISYNNTNREDLLILWGIHHSNNA
SEQ ID NO:24    (151) CPYQGASSFFRNVVWLIKKNDAYPTIKISYNNTNREDLLILWGIHHSNNA
SEQ ID NO:26    (151) CPYQGASSFFRNVVWLIKKNDAYPTIKISYNNTNREDLLILWGIHHSNNA
SEQ ID NO:27    (151) CPYQGMPSFFRNVVWLTKKNDAYPTIKMSYNNTNREDLLILWGIHHSNNA
SEQ ID NO:28    (151) CPYQGMPSFFRNVVWLTKKNDAYPTIKMSYNNTNREDLLILWGIHHSNNA
SEQ ID NO:25    (151) CPYQGAPSFFRNVVWLIKKNDAYPTIKISYNNTNREDLLILWGIHHSNNA
SEQ ID NO:20    (151) CPYQGASSFFRNVVWLIKKNDAYPTIKISYNNTNREDLLILWGIHHSNNA
SEQ ID NO:21    (151) CPYQGASSFFRNVVWLIKKNDAYPTIKISYNNTNREDLLILWGIHHSNNA
SEQ ID NO:22    (151) CPYQGASSFFRNVVWLIKKNDAYPTIKISYNNTNREDLLILWGIHHSNNA
                        201                                             250
SEQ ID NO:2     (201) AEQTNLYKNPDTYVSVGTSTLNQRLVPKIATRSQVNGQSGRMDFFWTILK
SEQ ID NO:4     (201) AEQTNLYKNPDTYVSVGTSTLNQRLVPKIATRSQVNGQNGRMDFFWTILK
SEQ ID NO:23    (201) AEQTNLYKNPDTYVSVGTSTLNQRLVPKIATRSQVNGQSGRMDFFWTILK
SEQ ID NO:24    (201) AEQTNLYKNPDTYVSVGTSTLNQRLVPKIATRSQVNGQSGRMDFFWTILK
SEQ ID NO:26    (201) AEQTNLYKNPDTYVSVGTSTLNQRLVPKIATRSQVNGQRGRMDFFWTILK
```

Figure 24F

```
SEQ ID NO:27   (201)  AEQTNLYKNPTTYVSVGTSTLNQRLVPKIATRSQVNGQRGRMDFFWTILK
SEQ ID NO:28   (201)  AEQTNLYKNPTTYVSVGTSTLNQRLVPKIATRSQVNGQRGRMDFFWTILK
SEQ ID NO:25   (201)  AEQTNLYKNPDTYVSVGTSTLNQRLVPKIATRSQVNGQSGRMDFFWTILK
SEQ ID NO:20   (201)  AEQTNLYKNPDTYVSVGTSTLNQRLVPKIATRSQVNGQSGRMDFFWTILK
SEQ ID NO:21   (201)  AEQTNLYKNPDTYVSVGTSTLNQRLVPKIATRSQVNGQSGRMDFFWTILK
SEQ ID NO:22   (201)  AEQTNLYKNPDTYVSVGTSTLNQRLVPKIATRSQVNGQSGRMDFFWTILK
                      251                                             300
SEQ ID NO:2    (251)  PNDAIHFESNGNFIAPEYAYKIVKKGDSTIMKSEMEYGHCNTKCQTPIGA
SEQ ID NO:4    (251)  PNDAIHFESNGNFIAPEYAYKIVKKGDSTIMKSEMEYGHCNTKCQTPIGA
SEQ ID NO:23   (251)  PNDAIHFESNGNFIAPEYAYKIVKKGDSTIMKSEMEYGHCNTKCQTPIGA
SEQ ID NO:24   (251)  PNDAIHFESNGNFIAPEYAYKIVKKGDSTIMKSEMEYGHCNTKCQTPIGA
SEQ ID NO:26   (251)  PNDAIHFESNGNFIAPEYAYKIVKKGDSTIMKSEVEYGHCNTKCQTPIGA
SEQ ID NO:27   (251)  PNDAIHFESNGNFIAPEYAYKIVKKGDSTIMKSEMEYGHCNTKCQTPIGA
SEQ ID NO:28   (251)  PNDAIHFESNGNFIAPEYAYKIVKKGDSTIMKSEMEYGHCNTKCQTPIGA
SEQ ID NO:25   (251)  PNDAIHFESNGNFIAPEYAYKIVKKGDSTIMKSEMEYGHCNTKCQTPIGA
SEQ ID NO:20   (251)  PNDAIHFESNGNFIAPEYAYKIVKKGDSTIMKSEMEYGHCNTKCQTPIGA
SEQ ID NO:21   (251)  PNDAIHFESNGNFIAPEYAYKIVKKGDSTIMKSEMEYGHCNTKCQTPIGA
SEQ ID NO:22   (251)  PNDAIHFESNGNFIAPEYAYKIVKKGDSTIMKSEMEYGHCNTKCQTPIGA
                      301                                             350
SEQ ID NO:2    (301)  INSSMPFHNIHPLTIGECPKYVKSNKLVLATGLRNSPLRETR---GLFGA
SEQ ID NO:4    (301)  INSSMPFHNIHPLTIGECPKYVKSNKLVLATGLRNSPLRETR---GLFGA
SEQ ID NO:23   (301)  INSSMPFHNIHPLTIGECPKYVKSNKLVLATGLRNSPLRETR---GLFGA
SEQ ID NO:24   (301)  INSSMPFHNIHPLTIGECPKYVKSNKLVLATGLRNSPLRETR---GLFGA
SEQ ID NO:26   (301)  INSSMPFHNIHPLTIGECPKYVKSNKLVLATGLRNSPLRETR---GLFGA
SEQ ID NO:27   (301)  INSSMPFHNIHPLTIGECPKYVKSNKLVLATGLRNSPLRERRRKRGLFGA
SEQ ID NO:28   (301)  INSSMPFHNIHPLTIGECPKYVKSNKLVLATGLRNSPLRETR---GLFGA
SEQ ID NO:25   (301)  INSSMPFHNIHPLTIGECPKYVKSNKLVLATGLRNSPQRETR---GLFGA
SEQ ID NO:20   (301)  INSSMPFHNIHPLTIGECPKYVKSNKLVLATGLRNSPLRETR---GLFGA
SEQ ID NO:21   (301)  INSSMPFHNIHPLTIGECPKYVKSNKLVLATGLRNSPLRETR---GLFGA
SEQ ID NO:22   (301)  INSSMPFHNIHPLTIGECPKYVKSNKLVLATGLRNSPLRETR---GLFGA
                      351                                             400
SEQ ID NO:2    (348)  IAGFIEGGWQGMVDGWYGYHHSNEQGSGYAADKESTQKAIDGVTNKVNSI
SEQ ID NO:4    (348)  IAGFIEGGWQGMVDGWYGYHHSNEQGSGYAADKESTQKAIDGVTNKVNSI
SEQ ID NO:23   (348)  IAGFIEGGWQGMVDGWYGYHHSNEQGSGYAADKESTQKAIDGVTNKVNSI
SEQ ID NO:24   (348)  IAGFIEGGWQGMVDGWYGYHHSNEQGSGYAADKESTQKAIDGVTNKVNSI
SEQ ID NO:26   (348)  IAGFIEGGWQGMVDGWYGYHHSNEQGSGYAADKESTQKAIDGVTNKVNSI
SEQ ID NO:27   (351)  IAGFIEGGWQGMVDGWYGYHHSNEQGSGYAADRESTQKAIDGVTNKVNSI
SEQ ID NO:28   (348)  IAGFIEGGWQGMVDGWYGYHHSNEQGSGYAADRESTQKAIDGVTNKVNSI
SEQ ID NO:25   (348)  IAGFIEGGWQGMVDGWYGYHHSNEQGSGYAADKESTQKAIDGVTNKVNSI
SEQ ID NO:20   (348)  IAGFIEGGWQGMVDGWYGYHHSNEQGSGYAADKESTQKAIDGVTNKVNSI
SEQ ID NO:21   (348)  IAGFIEGGWQGMVDGWYGYHHSNEQGSGYAADKESTQKAIDGVTNKVNSI
SEQ ID NO:22   (348)  IAGFIEGGWQGMVDGWYGYHHSNEQGSGYAADKESTQKAIDGVTNKVNSI
                      401                                             450
SEQ ID NO:2    (398)  IDKMNTQFEAVGREFNNLERRIENLNKKMEDGFLDVWTYNAELLVLMENE
SEQ ID NO:4    (398)  IDKMNTQFEAVGREFNNLERRIENLNKKMEDGFLDVWTYNAELLVLMENE
SEQ ID NO:23   (398)  IDKMNTQFEAVGREFNNLERRIENLNKKMEDGFLDVWTYNAELLVLMENE
SEQ ID NO:24   (398)  IDKMNTQFEAVGREFNNLERRIENLNKKMEDGFLDVWTYNAELLVLMENE
SEQ ID NO:26   (398)  IDKMNTQFEAVGREFNNLERRIENLNKKMEDGFLDVWTYNAELLVLMENE
SEQ ID NO:27   (401)  IDKMNTQFEAVGREFNNLERRIENLNKKMEDGFLDVWTYNAELLVLMENE
SEQ ID NO:28   (398)  IDKMNTQFEAVGREFNNLERRIENLNKKMEDGFLDVWTYNAELLVLMENE
SEQ ID NO:25   (398)  IDKMNTQFEAVGREFNNLERRIENLNKKMEDGFLDVWTYNAELLVLMENE
SEQ ID NO:20   (398)  IDKMNTQFEAVGREFNNLERRIENLNKKMEDGFLDVWTYNAELLVLMENE
SEQ ID NO:21   (398)  IDKMNTQFEAVGREFNNLERRIENLNKKMEDGFLDVWTYNAELLVLMENE
SEQ ID NO:22   (398)  IDKMNTQFEAVGREFNNLERRIENLNKKMEDGFLDVWTYNAELLVLMENE
```

Figure 24G

```
                         451                                              500
SEQ ID NO:2     (448)  RTLDFHDSNVKNLYDKVRLQLRDNAKELGNGCFEFYHKCDNECMESVRNG
SEQ ID NO:4     (448)  RTLDFHDSNVKNLYDKVRLQLRDNAKELGNGCFEFYHKCDNECMESVRNG
SEQ ID NO:23    (448)  RTLDFHDSNVKNLYDKVRLQLRDNAKELGNGCFEFYHKCDNECMESVRNG
SEQ ID NO:24    (448)  RTLDFHDSNVKNLYDKVRLQLRDNAKELGNGCFEFYHKCDNECMESVRNG
SEQ ID NO:26    (448)  RTLDFHDSNVKNLYDKVRLQLRDNAKELGNGCFEFYHKCDNECMESVRNG
SEQ ID NO:27    (451)  RTLDFHDSNVKNLYDKVRLQLRDNAKELGNGCFEFYPKCDNECMESVRNG
SEQ ID NO:28    (448)  RTLDFHDSNVKNLYDKVRLQLRDNAKELGNGCFEFYPKCDNECMESVRNG
SEQ ID NO:25    (448)  RTLDFHDSNVKNLYDKVRLQLRDNAKELGNGCFEFYHKCDNECMESVRNG
SEQ ID NO:20    (448)  RTLDFHDSNVKNLYDKVRLQLRDNAKELGNGCFEFYHKCDNECMESVRNG
SEQ ID NO:21    (448)  RTLDFHDSNVKNLYDKVRLQLKDNAKELGNGCFEFYHKCDNECMESVRNG
SEQ ID NO:22    (448)  RTLDFHDSNVKNLYDKVRLQLRDNAKELGNGCFEFYHKCDNECMESVRNG
                         501                                              550
SEQ ID NO:2     (498)  TYDYPKYSEEAILKREEISGVKLESIGTYQILSIYSTVASSLALAIIVAG
SEQ ID NO:4     (498)  TYDYPKYSEEAILKREEISGVKLESIGTYQILSIYSTVASSLALAIIVAG
SEQ ID NO:23    (498)  TYDYPKYSEEAILKREEISGVKLESIGTYQILSIYSTVASSLALAIIVAG
SEQ ID NO:24    (498)  TYDYPKYSEEAILKREEISGVKLESIGTYQILSIYSTVASSLALAIIVAG
SEQ ID NO:26    (498)  TYDYPQYSEEARLKREEISGVKLESIGTYQILSIYSTVASSLVLAIIVAG
SEQ ID NO:27    (501)  TYDYPQYSEEARLKREEISGVKLESIGTYQILSIYSTVASSLALAIIVAG
SEQ ID NO:28    (498)  TYDYPQYSEEARLKREEISGVKLESIGTYQILSIYSTVASSLALAIIVAG
SEQ ID NO:25    (498)  TYDYPKYSEEAILKREEISGVKLESIGTYQILSIYSTVASSLALAIIVAG
SEQ ID NO:20    (498)  TYDYPKYSEEAILKREEISGVKLESIGTYQILSIYSTVASSLALAIIVAG
SEQ ID NO:21    (498)  TYDYPKYSEEAILKREEISGVKLESIGTYQILSIYSTVASSLALAIIVAG
SEQ ID NO:22    (498)  TYDYPKYSEEAILKREEISGVKLESIGTYQILSIYSTVASSLALAIIVAG
                         551             567
SEQ ID NO:2     (548)  LSLWMCSNGSLQCRICI
SEQ ID NO:4     (548)  LSLWMCSNGSLQCRICI
SEQ ID NO:23    (548)  LSLWMCSNGSLQCRICI
SEQ ID NO:24    (548)  LFLWMCSNGSLQCRICI
SEQ ID NO:26    (548)  LSLWMCSNGSLQCRICI
SEQ ID NO:27    (551)  LSLWMCSNGSLQCRICI
SEQ ID NO:28    (548)  LSLWMCSNGSLQCRICI
SEQ ID NO:25    (548)  LSLWMCSNGSLQCRICI
SEQ ID NO:20    (548)  LSLWMCSNGSLQCRICI
SEQ ID NO:21    (548)  LSLWMCSNGSLQCRICI
SEQ ID NO:22    (548)  LSLWMCSNGSLQCRICI
```

Sequence identity percentage (%)

| SEQ ID NO: | 2 | 4 | 20 | 21 | 22 | 23 | 24 | 25 | 26 | 27 | 28 |
|---|---|---|---|---|---|---|---|---|---|---|---|
| 2 | | 99.5 | 99.6 | 99.6 | 99.6 | 99.5 | 99.5 | 99.1 | 98.2 | 96.5 | 97.2 |
| 4 | | | 99.1 | 99.1 | 99.1 | 98.9 | 98.9 | 98.6 | 97.9 | 96.1 | 96.8 |
| 20 | | | | 99.6 | 99.6 | 99.5 | 99.5 | 99.1 | 98.2 | 96.5 | 97.2 |
| 21 | | | | | 99.6 | 99.5 | 99.5 | 99.1 | 98.2 | 96.5 | 97.2 |
| 22 | | | | | | 99.5 | 99.5 | 99.1 | 98.2 | 96.5 | 97.2 |
| 23 | | | | | | | 99.6 | 98.9 | 98.4 | 96.6 | 97.3 |
| 24 | | | | | | | | 98.9 | 98.4 | 96.6 | 97.3 |
| 25 | | | | | | | | | 97.7 | 96.3 | 97.0 |
| 26 | | | | | | | | | | 97.2 | 97.9 |
| 27 | | | | | | | | | | | 99.3 |
| 28 | | | | | | | | | | | |

RECOMBINANT VECTORS EXPRESSING ANTIGENS OF AVIAN INFLUENZA VIRUS AND USES THEREOF

CROSS-REFERENCE TO RELATED APPLICATIONS

This application claims priority to U.S. provisional application 62/410,885 filed on Oct. 21, 2016.

FIELD OF THE INVENTION

The invention relates to recombinant viral vectors for the insertion and expression of foreign genes for use as safe immunization vehicles to protect against a variety of pathogens. It also relates to multivalent composition or vaccine comprising one or more recombinant viral vectors for protection against a variety of pathogens. The present invention relates to methods of making and using the recombinant viral vectors.

BACKGROUND OF THE INVENTION

Influenza virus is a member of Orthomyxoviridae family (Murphy and Webster, Orthomyxoviruses, Fields Virology, Third Edition, vol. 1, pp. 1397-1445, 1996). There are three types of influenza viruses designated A, B, and C. The influenza virion contains a segmented negative-sense RNA genome. The influenza virion includes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2) proteins. The NP and the matrix protein M1 are used to classify the influenza virus into group A, B or C.

The HA and NA proteins are envelope glycoproteins. The HA protein is responsible for virus attachment and penetration of the viral particles into the cell and contains the major immunodominant epitopes for virus neutralization and protective immunity. Both HA and NA proteins are considered the most important components for prophylactic influenza vaccines. To date, eighteen different HA subtypes and eleven different NA subtypes have been identified (Tong et al., 2013, PLoS Pathogens, Vol. 9 (10), New World Bats harbor diverse influenza A viruses).

Globally, influenza is the most economically significant respiratory disease in humans, pigs, horses and poultry. Influenza virus is known for its continuous genetic and antigenic changes, which impede effective control of the virus. Of particular concern for prevention of epidemics and pandemics is the emergence of a new subtype of the virus by genetic re-assortment or inter-species transmission.

The highly pathogenic Influenza A virus subtype H5N1 virus is an emerging avian influenza virus (AIV) that has been causing global concern as a potential pandemic threat. H5N1 has killed millions of poultry in a growing number of countries throughout Asia, Europe and Africa. Health experts are concerned that the co-existence of human flu viruses and avian flu viruses (especially H5N1) will provide an opportunity for genetic material to be exchanged between species-specific viruses, possibly creating a new virulent influenza strain that is easily transmissible and lethal to humans (Food Safety Research Information Office. "A Focus on Avian Influenza". Created May 2006, Updated November 2007). U.S. Pat. No. 8,394,384 reported the making of avian influenza vaccines using plant expression system. U.S. Pat. No. 7,910,112 disclosed poxvirus vectored vaccines against avian influenza. U.S. Pat. No. 8,592,558 disclosed vaccines containing H5 proteins. WO2007019094 studied the immunogenicity of the HA molecule when specific HA residues are substituted.

During Dec. 15, 2014 and Jan. 16, 2015, the U.S. Department of Agriculture received 14 reports of birds infected with Asian-origin, highly pathogenic avian influenza A (HPAI), including H5N2 viruses. These reports represent the first reported infections with these viruses in U.S. wild or domestic birds. Although these viruses are not known to have caused disease in humans, their appearance in North America might increase the likelihood of human infection in the United States (Morbidity and Mortality Weekly Report, Centers for Disease Control and Prevention, Feb. 6, 2015/64(04), 111; Bertran et al., 2016, Virology 494, 190-197).

Considering the susceptibility of animals, including humans, to AIV, a method of preventing AIV infection and protecting animals is essential. Accordingly, there is a need for methods to produce effective vaccines against influenza.

SUMMARY OF THE INVENTION

The present invention relates to a recombinant herpesvirus of turkey (HVT) vector or fowlpox virus (FPV) vector comprising one or more heterologous polynucleotides coding for and expressing at least one antigen of an avian pathogen.

The present invention provides a composition or vaccine comprising one or more recombinant HVT or FPV vectors comprising one or more heterologous polynucleotides coding for and expressing at least one antigen of an avian pathogen.

The present invention also provides a polyvalent composition or vaccine comprising one or more recombinant HVT or FPV vectors comprising heterologous polynucleotides coding for and expressing at least one antigen of an avian pathogen and one or more recombinant HVT or FPV vectors comprising heterologous polynucleotides coding for and expressing at least one antigen of an avian pathogen.

The present invention relates to a method of vaccinating an animal, or inducing an immunogenic or protective response in an animal, comprising at least one administration of the composition or vector of the present invention.

The present invention showed surprising result that the recombinant viral vectors expressing the modified HA protein provided better protection in avian than the recombinant viral vectors expressing the mutant HA protein. The present invention also demonstrated that polyvalent compositions or vaccines comprising the viral vectors were effective to protect animals against a variety of avian pathogens without interference.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIGS. 1A and 1B depicts a table showing the SEQ ID NO assigned to each DNA and protein sequence.

FIGS. 24A-24G depict the DNA and protein sequence alignments.

DETAILED DESCRIPTION OF THE INVENTION

Figure 2:
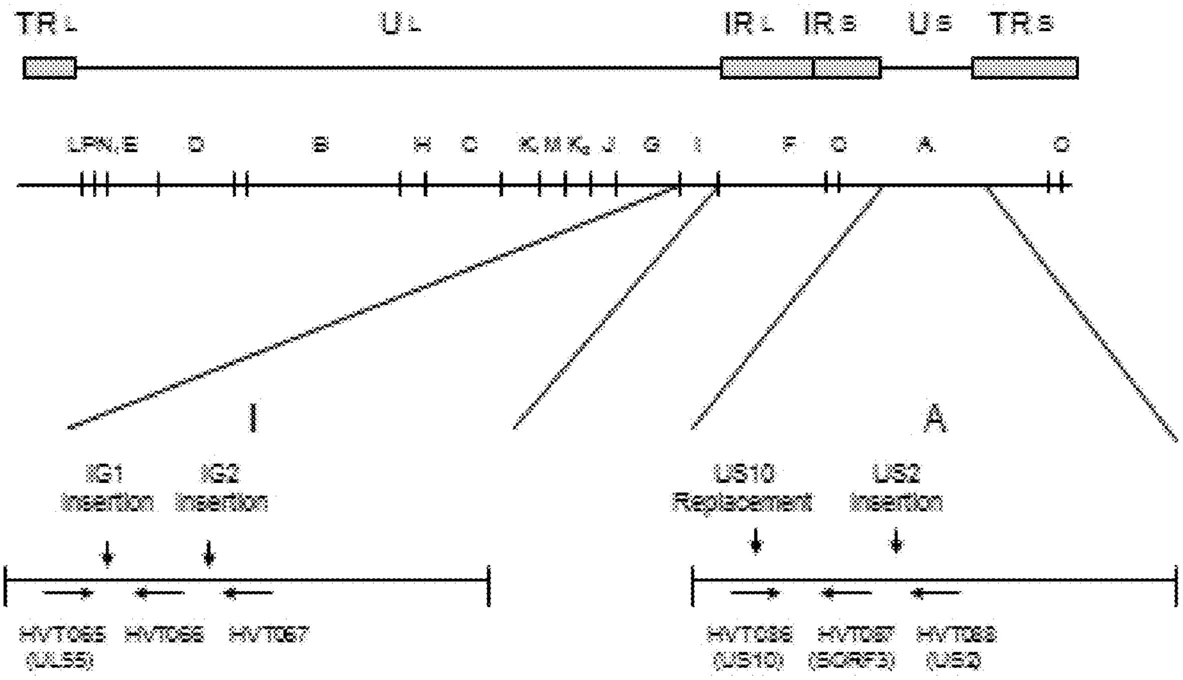
FIG. 2 depicts the genome structure of HVT and its insertion sites. The UL55 insertion site is shown.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a", "an" and "the" include plural referents unless context clearly indicates otherwise. Similarly, the word "or" is intended to include "and" unless the context clearly indicate otherwise. The word "or" means any one member of a particular list and also includes any combination of members of that list.

The term "about" as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

A particular antigenic polypeptide of interest is hemagglutinin (HA). Influenza hemagglutinin refers to a type of hemagglutinin found on the surface of the influenza viruses. It is an antigenic glycoprotein and is responsible for binding the virus to the cell that is being infected. There are different HA antigens, any of which can be used in the practice of the invention. Of interest is the HA from H5N2, a highly pathogenic avian flu virus. However, HA from other influenza viruses (i.e. H1-H16) may be used in the practice of the invention including H1, H3, H5, H6, H7, H9 and the like. It is further recognized that HA precursors of any of the HA proteins can be used.

HA is a homotrimeric transmembrane protein with an ectodomain composed of a globular head and a stem region. Both regions carry N-linked oligosaccharides, which plays an important role in the biological function of HA (Schulze, I. T., J Infect Dis, 1997. 176 Suppl 1: p. S24-8; Deshpande, K. L., et al., PNAS USA, 1987, 84(1): p. 36-40). Among different subtypes of influenza A viruses, there is significant variation in the glycosylation sites of the head region, whereas the stem oligosaccharides are more conserved and required for fusion activity (Ohuchi, R., et al., J Virol, 1997, 71(5): p. 3719-25). Glycans near antigenic peptide eptiopes interfere with antibody recognition (Skehel, J. J., et al., *PNAS USA,* 1984, 81(6): p. 1779-83), and glycans near the proteolytic site modulate cleavage and influence the infectivity of influenza virus (Deshpande, K. L., et al., 1987). Nucleotide sequence analysis of 62 H5 genes supported the hypothesis that additional glycosylation near the receptor binding site within the HA globular head is an adaptation of the virus following interspecies transmission from wild birds, particularly waterfowl, to poultry (Banks, J., et al., Avian Dis, 2003, 47(3 Suppl): p. 942-50).

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene), transcription terminators (in general the terminator is located within approximately 50 nucleotides downstream of the stop codon of the coding sequence or gene). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers to a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, or a mixture of recombinant viral vectors and wild-type viruses in active or attenuated or killed forms.

One embodiment of the invention provides a recombinant HVT viral vector comprising one or more heterologous polynucleotides coding for and expressing at least one antigen or polypeptide of an avian pathogen. The HVT strains used for the recombinant viral vector may be any HVT strains, including, but not limited to, the HVT strain FC126 (Igarashi T. et al., J. Gen. Virol. 70, 1789-1804, 1989).

Another embodiment of the invention provides a recombinant poxvirus viral vector comprising one or more heterologous polynucleotides coding for and expressing at least one antigen or polypeptide of an avian pathogen. The poxvirus may be a vaccinia virus or an avipox virus, such as fowlpox virus and canarypox virus. The canarypox virus or fowlpox virus strains may be attenuated strains, such as an attenuated recombinant canarypox virus, for instance ALVAC (U.S. Pat. No. 5,756,103), or an attenuated fowlpox virus, for instance TROVAC (U.S. Pat. Nos. 5,766,599, 5,174,993, 5,505,941). Both ALVAC and TROVAC include derivatives that have been passaged from the parental strains of ALVAC or TROVAC, and/or the progenies or descendants of ALVAC or TROVAC. In one embodiment, the recombinant TROVAC vaccine may be used as an avian influenza vaccine. In the case of fowlpox, the insertion site or sites are ORFs F7 and/or F8. The F8 insertion locus corresponds to the fowlpox gene encoding photolyase described by Srinivasan and Tripathy (2005, Veterinary Microbiology 108: 215-223). This gene is also described under the name FPV158 in the complete sequence of the fowlpox genome (GenBank accession No. AF198100.1). In the case of canarypox, the insertion site or sites are ORF(s) C3, C5 and/or C6; see also documents cited herein, especially those pertaining to canarypox virus.

Thus, the viral vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc.

Another embodiment of the invention provides a recombinant NDV viral vector comprising one or more heterologous polynucleotides coding for and expressing at least one antigen or polypeptide of an avian pathogen. The NDV strains may be any NDV strains, including, but not limited to, Ulster 2C, Queensland V4, Hitchner B1, F (e.g., Asplin), La Sota, strain H, Mukteswar, Roakin, Beaudette C, Texas G B, N Y parrot 70181, Italien, Milano, Herts 33/56, and AVINEW®.

The genes coding for antigen or polypeptide may be those coding for avian influenza virus HA protein. The antigen or polypeptide may be any antigen from the poultry pathogen of avian influenza virus. The avian influenza virus may be any subtype AIV, including, but not limited to, H5, H7 and H9.

Moreover, homologs of aforementioned antigens or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences of antigens described above, and will exhibit a similar function.

In one embodiment, the present invention provides a recombinant HVT or FPV viral vector comprising one or more heterologous polynucleotides coding for and expressing the AIV-HA antigen or polypeptide. In one aspect of the embodiment, the AIV-HA antigen or polypeptide has at least 70%, 75%, 80%, 85%, 90%, 95%, 96%, 97%, 98% or 99% sequence identity to a polypeptide having the sequence as set forth in SEQ ID NO:2, 4, 20, 21, 22, 23, 24, 25, 26, 27, and 28 or a conservative variant, an allelic variant, a homolog or an immunogenic fragment comprising at least eight or at least ten consecutive amino acids of one of these polypeptides, or a combination of these polypeptides. The AIV-HA antigen or polypeptide may be modified at the cleavage site between HA1 and HA2 from a highly pathogenic avian influenza sequence (multiple basic amino acids: RERRRKR-SEQ ID NO:14) to a low pathogenic avian influenza sequence (RETR-SEQ ID NO:15). In another aspect of the embodiment, the heterologous polynucleotide encoding an AIV-HA antigen or polypeptide having at least 70%, 75%, 80%, 85%, 90%, 95%, 96%, 97%, 98% or 99% sequence identity to a polypeptide having the sequence as set forth in SEQ ID NO:2, 4, 20, 21, 22, 23, 24, 25, 26, 27, and 28. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:1, 3, 8, 9, 10, 12, 13 17, or 19.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for AIV-HA polypeptides, the DNA sequence of the AIV-HA protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of AIV-HA protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the AIV-HA polypeptide encoded by the nucleotide sequence is functionally unchanged.

Successful expression of the heterologous polynucleotides by the recombinant/modified infectious virus requires two conditions. First, the heterologous polynucleotides must be inserted or introduced into a region of the genome of the virus in order that the modified virus remains viable. The second condition for expression of inserted heterologous polynucleotides is the presence of a regulatory sequences allowing expression of the gene in the viral background (for instance: promoter, enhancer, donor and acceptor splicing sites and intron, Kozak translation initiation consensus sequence, polyadenylation signals, untranslated sequence elements).

The insertion site may be any non-essential region of the HVT genome, including, but not limited to, the region between the STOP codon of ORF UL55 and the junction of UL with the adjacent repeat region (intergenic region 1, the IG1 locus, U.S. Pat. No. 5,980,906), the IG2 (intergenic region 2) locus, the IG3 (intergenic region 3) locus, the UL43 locus, the US10 locus, the US2 locus, the SORF3/US2 locus (see FIG. 2)

In general, it is advantageous to employ a strong promoter functional in eukaryotic cells. The promoters include, but are not limited to, an immediate early cytomegalovirus (CMV) promoter, mouse CMV IE promoter, guinea pig CMV promoter, an SV40 promoter, Human Herpesvirus Type III glycoprotein B (HHV3gB) promoter, Pseudorabies Virus promoters such as that of glycoprotein X promoter, Herpes Simplex Virus-1 such as the alpha 4 promoter, Marek's Disease Viruses (including MDV-1, MDV-2 and HVT) promoters such as those driving glycoproteins gC, gB, gE, or gI expression, Infectious Laryngotracheitis Virus promoters such as those of glycoprotein gB, gE, gI, gD genes, or other herpesvirus promoters.

One embodiment of the invention provides a recombinant HVT vector comprising a heterologous polynucleotide coding for and expressing the AIV-HA antigen or polypeptide. In one aspect of the embodiment, the polynucleotide encoding the AIV-HA polypeptide is operably linked to the SV40 promoter having the sequence as set forth in SEQ ID NO:5 and therefore the expression of the AIV-HA antigen or polypeptide is regulated by the SV40 promoter. In another aspect of the embodiment, the polynucleotide encoding the AIV-HA polypeptide is operably linked to the mCMV promoter having the sequence as set forth in SEQ ID NO:16 and therefore the expression of the AIV-HA antigen or polypeptide is regulated by the mCMV promoter. In yet another aspect of the embodiment, the expression of AIV-HA antigen or polypeptide is regulated by the synthetic polyA signal having the sequence as set forth in SEQ ID NO:7. In yet another aspect of the embodiment, the expression of AIV-HA antigen or polypeptide is regulated by the SV40 PolyA having the sequence as set forth in SEQ ID NO:18. In yet another aspect of the embodiment, the polynucleotide encoding the AIV-HA polypeptide is operably linked to the HHV3gB promoter in reverse orientation having the sequence as set forth in SEQ ID NO:6 and therefore the expression of the NDV-F antigen or polypeptide is regulated by the HHV3gB promoter and/or SV40 promoter. In one aspect, the polynucleotide encoding the AIV-HA polypeptide is codon-optimized. In yet another aspect, the polynucleotide encoding the AIV-HA polypeptide is wild-type DNA.

Another embodiment of the invention provides a recombinant FPV vector comprising a heterologous polynucleotide coding for and expressing the AIV-HA antigen or polypeptide. In one aspect of the embodiment, the polynucleotide encoding the AIV-HA polypeptide is operably linked to linked to vaccinia H6 (H6) promoter having the sequence as set forth in SEQ ID NO:11 and therefore the expression of the AIV-HA antigen or polypeptide is regulated by the H6 promoter.

In another embodiment, the present invention provides a pharmaceutical composition or vaccine comprising an HVT or FPV viral vector comprising a polynucleotide encoding an AIV-HA antigen, and optionally a pharmaceutically or veterinarily acceptable carrier, excipient, vehicle or adjuvant. In another embodiment, the present invention provides a pharmaceutical polyvalent composition or vaccine comprising two or more viral vectors comprising polynucleotides encoding AIV-HA antigens, and optionally a pharmaceutically or veterinarily acceptable carrier, excipient, vehicle or adjuvant. The viral vectors may be HVT vector or FPV vector.

The pharmaceutically or veterinarily acceptable carriers or adjuvants or vehicles or excipients are well known to the one skilled in the art. Other pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate) or polyvinylpyrrolidone. The pharmaceutically or veterinarily acceptable carrier or vehicle or adjuvant or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvants or vehicles or excipients, including, but not limited to, alum; CpG oligonucleotides (ODN), in particular ODN 2006, 2007, 2059, or 2135 (Pontarollo R. A. et al., *Vet. Immunol. Immunopath,* 2002, 84: 43-59; Wernette C. M. et al., *Vet. Immunol. Immunopath,* 2002, 84: 223-236; Mutwiri G. et al., *Vet. Immunol. Immunopath,* 2003, 91: 89-103); polyA-polyU, dimethyldioctadecylammonium bromide (DDA) ("Vaccine Design The Subunit and Adjuvant Approach", edited by Michael F. Powell and Mark J. Newman, *Pharmaceutical Biotechnology,* 6: p. 03, p. 157); N,N-dioctadecyl-N',N'-bis(2-hydroxyethyl) propanediamine (such as AVRIDINE®) (Ibid, p. 148); carbomer, chitosan (see U.S. Pat. No. 5,980,912 for example).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In one embodiment, the adjuvant may include TS6 TS7, TS8 and TS9 (U.S. Pat. No. 7,371,395), LR2, LR3 and LR4 (U.S. Pat. No. 7,691,368), TSAP (U520110129494), TRIGEN™ (Newport Labs), synthetic dsRNAs (e.g. poly-IC, poly-ICLC [HILTONOL®]), and MONTANIDE™ adjuvants (W/O, W/O/W, O/W, IMS and Gel; all produced by SEPPIC).

In one embodiment, the invention provides for the administration of a therapeutically effective amount of a vaccine or composition for the delivery of recombinant HVT and FPV vectors in a target cell. Determination of the therapeutically effective amount is routine experimentation for one of ordinary skill in the art.

Another aspect of the invention relates to a method for inducing an immunological response in an animal against one or more antigens or a protective response in an animal against one or more avian pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more avian pathogens in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster. The prime-boost protocol according to the invention comprises a primary administration followed by at least a second administration to boost the response.

In one aspect of the prime-boost protocol of the invention, a composition or vaccine comprising a recombinant viral vector that contains and expresses an avian influenza antigen in vivo is administered followed by the administration of a composition or vaccine comprising a recombinant viral vector that contains and expresses an avian influenza antigen in vivo. The recombinant viral vector used in prime-administration may be different in nature from those used as a later booster recombinant vector. The viral vector used in the prime-administration may be selected from HVT or FPV, and the viral vector used in the boost-administration may be selected from HVT or FPV that is different from the viral vector used in the prime administration. It is noted however that the prime and boost composition or vaccine may contain the same recombinant vector. It is also noted that the prime and boost composition or vaccine may be polyvalent position or vaccine which may contain two or more viral vectors.

A prime-boost regimen may comprise at least one prime-administration and at least one boost administration using at least one common polypeptide or antigen. A prime-boost regimen may also comprise at least one prime-administration and at least one boost administration using different polypeptides or antigens. The prime-administration may comprise one or more administrations. Similarly, the boost administration may comprise one or more administrations.

The avian pathogens may be Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus coccidiosis (*Eimeria* sp.), *Campylobacter* sp., *Salmonella* sp., *Mycoplasma gallisepticum, Mycoplasma synoviae, Pasteurella* sp., *Avibacterium* sp., *E. coli* or *Clostridium* sp.

Usually, one administration of the vaccine is performed either at one day-of-age by the subcutaneous or intramuscular route or in ovo in 17-19 day-old embryo. A second administration can be done within 5-30 days after the first administration.

A variety of administration routes in day-old chicks may be used such as subcutaneously or intramuscularly, intradermally, transdermally. The in ovo vaccination can be performed in the amniotic sac and/or the embryo. Commercially available in ovo and SC administration devices can be used for vaccination.

The composition or vaccine may contain a dose from about $10^2$ to about $10^{20}$, about $10^3$ to about $10^{18}$, about $10^4$ to about $10^{16}$, about $10^5$ to about $10^{12}$ VLPs (virus like particles) produced in vitro or in vivo from a viral vector, a plasmid, or baculovirus. The viral vector may be titrated based on any virus titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose), and the VLPs produced in vitro can be titrated by hemagglutination assay, ELISA, and electron microscopy. Other methods may also be applicable depending on the type of VLP. The composition or vaccine may contain from about $10^{2.0}$ to about $10^{10.0}$ pfu/dose of viral vector.

The dose volumes can be between about 0.1 and about 10 ml, between about 0.1 and about 5 ml.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, N.Y., 2014).

Example 1

Construction of Recombinant HVT Vectors Expressing H5N2-HA

Example 1.1

Construction of Recombinant HVT501 Expressing H5N2-HA

The objective of the study is to construct a recombinant HVT virus in which an expression cassette containing Simian Virus 40 (SV40) promoter, Avian Influenza Virus Hemagglutinin (HA) glycoprotein, and a synthetic poly A tail is inserted in the intergenic site of UL55 in HVT virus (FIG. 2).

The parental virus used in the construct is HVT FC126. An Avian Influenza Virus Heagglutinin (HA) glycoprotein (named LPC-HA) corresponding to H5N2-HA sequence (SEQ ID NO:2 encoded by SEQ ID NO:1, codon-optimized) was chemically synthesized (GenScript). The H5N2-HA (LPC-HA) was derived from a highly pathogenic avian influenza A virus (A/chicken/Washington/61-9/2014(H5N2) isolate (GenBank accession No. KP739381.1). The synthetic HA (LPC-HA) gene was modified at the cleavage site between HA1 and HA2 from a highly pathogenic avian influenza sequence (multiple basic amino acids: RERRRKR—SEQ ID NO:14) to a low pathogenic avian influenza sequence (RETR—SEQ ID NO:15).

The promoter is Simian Virus 40 (SV40) promoter (SEQ ID NO:5). The insertion locus is intergenic site of UL55 (IG1) in HVT (FIG. 2). Donor plasmid pHVTIG1SVLPC-HAsyn SbfI (an insertion plasmid containing the UL55 flanking regions of HVT virus+SV40+synthetic poly A) was constructed as described below. Chicken embryo fibroblast cells (CEF) were used for in vitro recombination.

Donor Plasmid Construction

To construct the donor plasmid pHVTIG1SVLPC-HAsyn SbfI, a fragment encompassing the synthetic H5N2-HA gene was excised from LPC-HA H5N2 in pUC57 (synthesized by GeneScript) using NotI and inserted into the same site as the pHVTIG2SVCaFsyn SbfI plasmid containing SV40 promoter, NDV-F gene, and synthetic polyA tail which was also NotI digested and CIP treated, to replacing the NDV-F gene with the LPC-HA. The NotI digested insert (LPC-HA) and vector (pHVTIG2) was gel extracted using Qiagens Gel Extraction Kit and then ligated. Ligated material was transformed using Top10 Oneshot kit (cat #C404002, Invitrogen). Bacterial colonies were grown in LBamp broth and plasmid was extracted using Qiagens MiniSpin Prep kit. The plasmids were screened for insert orientation using SmaI digestion. The correct donor plasmid was designated pHVTIG2SVLPC-HAsyn SbfI. pHVTIG2SVLPC-HAsyn SbfI mini-prep plasmid was transfected onto one well of a 6-well plate and an IFA was performed using chicken anti-sera against Avian Influenza H5N2 (Charles Rivers Laboratories, Lot #J0210) and anti-chicken FITC (Sigma, Cat #F8888). Once transient expression was verified the plasmid was grown in a larger scale culture and plasmid extraction was done by using Qiagens Maxi Prep kit.

Figure 3:
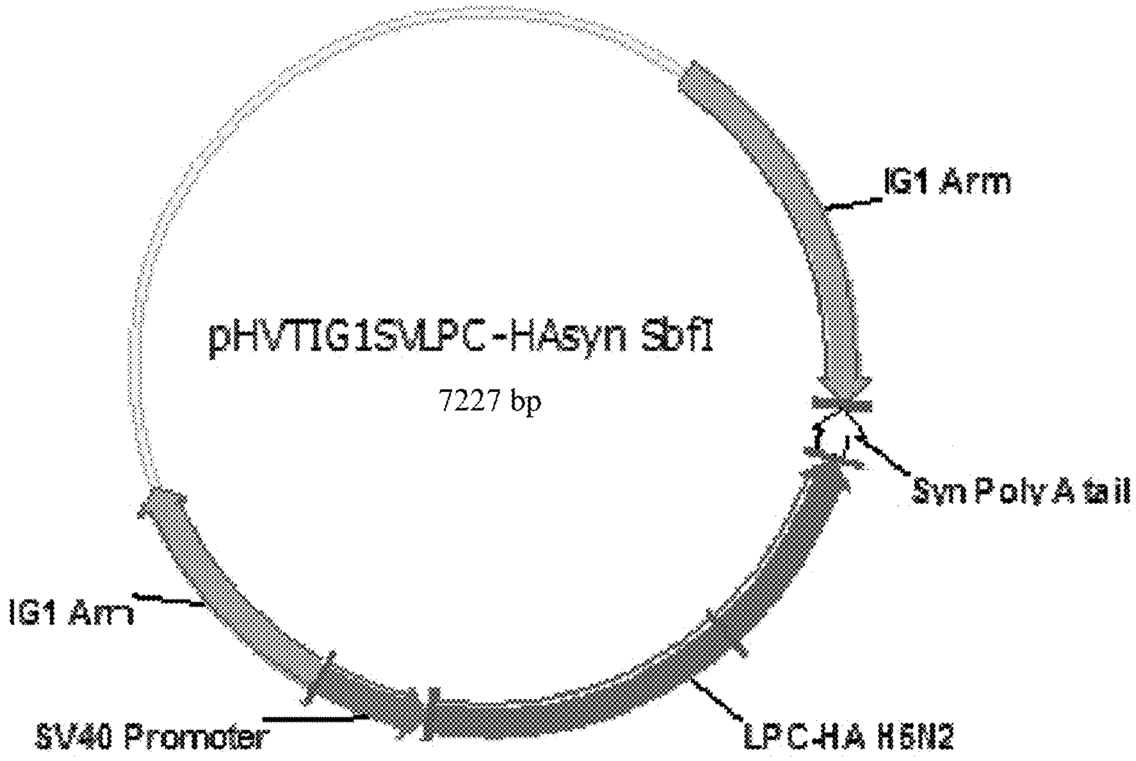
FIG. 3 depicts pHVTIG1SVLPC-HAsyn SbfI plasmid map.

An SbfI digest was performed on the pHVTIG2SVLPC-HAsyn SbfI maxi prep and pIG1HHV3gBroCaFoptsyn SbfI maxi prep (a previously constructed and sequence verified plasmid). The SV40 H5N2-HA synthetic poly A tail expression cassette flanked by SbfI restriction enzymes was gel extracted from the pHVTIG2SVLPC-HAsyn SbfI plasmid using Qiagens Gel Extraction Kit. The pIG1HHV3gBroCaFoptsyn SbfI vector flanked by SbfI restriction enzymes was also gel extracted and CIP treated. The pHVTIG2SVLPC-HAsyn SbfI expression cassette was ligated to the pIG1HHV3gBCaFsyn SbfI vector. Ligated material was transformed using Top10 Oneshot kit (cat #C404002, Invitrogen). Bacterial colonies were grown in LBamp broth and plasmid was extracted using Qiagens MiniSpin Prep kit. The plasmids were screened for insert orientation using EcoRI+SmaI digestion. An anti-genome orientation plasmid was selected, grown in a larger scale culture, and plasmid extraction was done by using Qiagens Maxi Prep kit. This plasmid was sequence verified and designated pHVTIG1SVLPC-HAsyn SbfI (FIG. 3).

Recombinant Generation

A standard homologous recombination procedure was followed by co-electroporation of secondary CEF cells using pHVTIG1SVLPC-HAsyn SbfI donor plasmid and viral DNA isolated from HVT FC126 virus. Co-electroporation was performed using $1\times10^7$ 2° CEF in 300 μl Opti-MEM and shocked at 150 volts with 950 capacitance in a 2 mm electroporation cuvette. The transfected cells were seeded into 96-well plate and incubated for 4 days. The cells grown in the 96-well plate were then duplicated into two 96-well plates and incubated for 3 more days. One set of 96-well plates was used for IFA using chicken polyclonal sera against Avian Influenza H5N2 to identify positive wells containing recombinants and another set of 96-well plates was used for recovering the infected cells from the positive wells.

The recombinant viral purification methods were performed first by 96-well plate duplication and IFA selection for the wells containing the most IFA positive plaques with the least amount of IFA negative plaques. Wells matching those criteria were then harvested and adjusted to 1 ml in DMEM+2% FBS. From the 1 ml stock 5-20 μl (depending on the number of visible plaques) were removed and mixed with $1\times10^7$ CEFs in 10 ml DMEM+2% FBS and aliquoted onto a new 96-well plate in an attempt to have single HVT plaques per well. The 96-well plates were duplicated after 3 days of incubation and wells that contained plaques were tested for the presence of recombinant HVT and absence of parental virus by IFA and PCR. Again the wells that appeared to have more recombinant virus, by comparing the PCR banding results, were harvested and adjusted to 1 ml and aliquoted onto new 96-well plates (the same as before). After three rounds of purification of virus infected cells, recombinant HVT expressing LPC-HA protein was isolated and the purity of the recombinant virus was tested by IFA and PCR to confirm the absence of parental virus. Selected recombinant virus was then passed from one well of a 96-well plate (P0) to 2×T-25 flasks (P1), then 2×T-75 flasks (P2), then 2×T-150 flasks (P3), and finally 3×850 $cm^2$ roller bottles (pre-MSV stock or P4). Vials with 2 ml aliquot were stored in liquid nitrogen.

Analysis of Recombinant by PCR

DNA was extracted from a stock virus by phenol/chloroform extraction; ethanol precipitated, and resuspended in 20 mM HEPES. PCR primers were designed to specifically identify the H5N2-HA gene, the promoter, the poly A, as well as, the purity of the recombinant virus from HVT parental virus. PCR was performed using 200 μg of DNA template along with the specified primers pairs indicted in Table 1. PCR cycling conditions are as follows (unless otherwise noted): 94° C.-2 min; 30 cycles of 94° C.-30 sec, 60° C.-45 sec, 68° C.-2 min; 68° C.-3 min.

Expression Analysis

For immunofluorescence testing, the P4 material was diluted 1:100 in media. Approximately 50 μl of the diluted virus was added to 10 ml of DMEM+2% FBS with $1\times10^7$ CEFs and then aliquoted onto a 96 well plate (100 μl/well). The plates were incubated for 3 days at 37° C.+5% $CO_2$ until viral plaques were visible. The plates were fixed with 95% ice-cold acetone for three minutes and rinsed gently three times with water. Chicken anti-sera against Avian Influenza H5N2 (lot #J0210, Charles Rivers Laboratory) at 1:500 and HVT Mab L78 (lot #072103, Merial) at 1:3000 was added and the plates were incubated at 37° C. for 45 minutes. After the incubation, the plates were washed three times with PBS and FITC anti-chicken (cat #F8888, Sigma) at 1:500 and TRITC anti-mouse (cat #A10037, Life Technologies) at 1:300 was added. Again the plates were incubated at 37° C. for 45 minutes. After the incubation the cells were rinsed three times with PBS and visualized with a fluorescent microscope using fluorescein isothiocyanate (FITC) filter and tetramethyl rhodamine isothiocyanate filter (TRITC).

Results

The nucleotide and amino acid sequences of the donor plasmid pHVTIG1SVLPC-HAsyn SbfI are assigned SEQ ID NOs as shown in FIG. 1.

Recombinant Generation and Expression Analyses

Genomic DNA of HVT FC126 virus was co-electroporated with pHVTIG1SVLPC-HAsyn SbfI donor plasmid to generate recombinant HVT using homologous recombination technique. Recombinant virus was separated from parental HVT virus by immunofluorescent positive well selection and PCR screening in multiple rounds of plaque purification. A plaque purified recombinant HVT virus expressing the LPC-HA H5N2 protein, designated rHVT501, was scaled up from tissue culture flasks to 3×850 $cm^2$ roller bottles. After about 72 hrs post infection the infected CEFs were harvested. Aliquots were frozen in liquid nitrogen containing 10% FBS and 10% DMSO. Titrations were performed in triplicate on CEFs and a titer of $5.75\times10^5$ pfu/ml was obtained for rHVT501.

Figure 4:
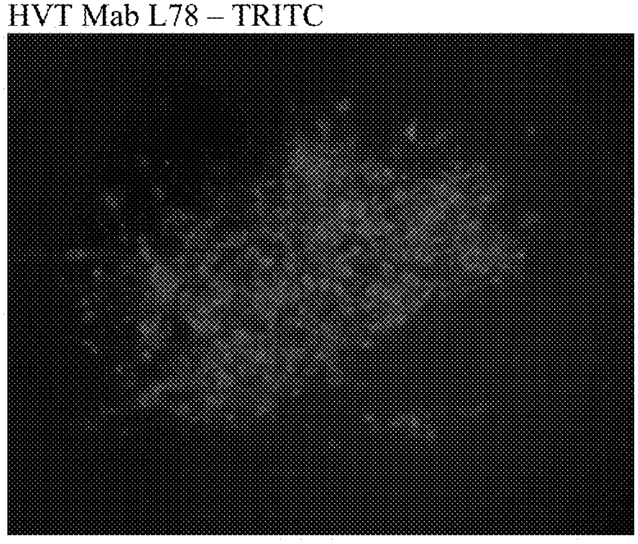
FIG. 4 depicts the dual immunofluorescent staining of recombinant vHVT501 virus expressing LPC-HA H5N2 protein.
Figure 4:
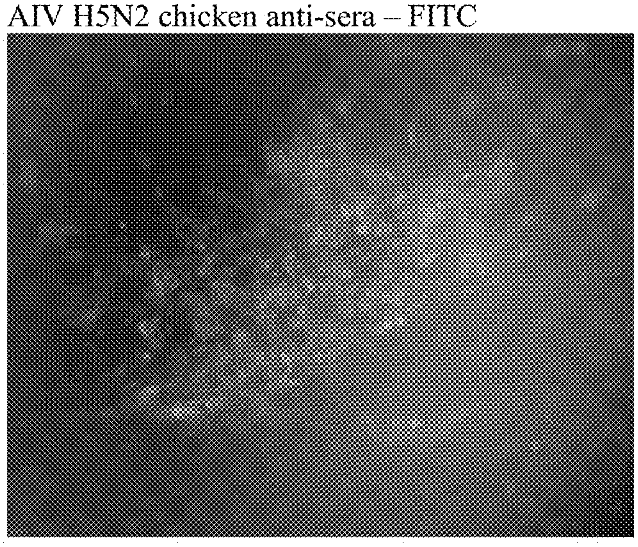

Immunofluorescents was performed using chicken antisera (lot #J0210, Charles Rivers Laboratories) and a monoclonal antibody specific to HVT (Merial) followed by a FITC labeled anti-chicken IgG (cat #F8888, Sigma) and TRITC labeled anti-mouse IgG (cat #A10037, Life Technologies). All examined plaques of rHVT501 were found to express LPC-HA H5N2 protein (FIG. 4).

PCR Analysis of rHVT501

Figure 5:
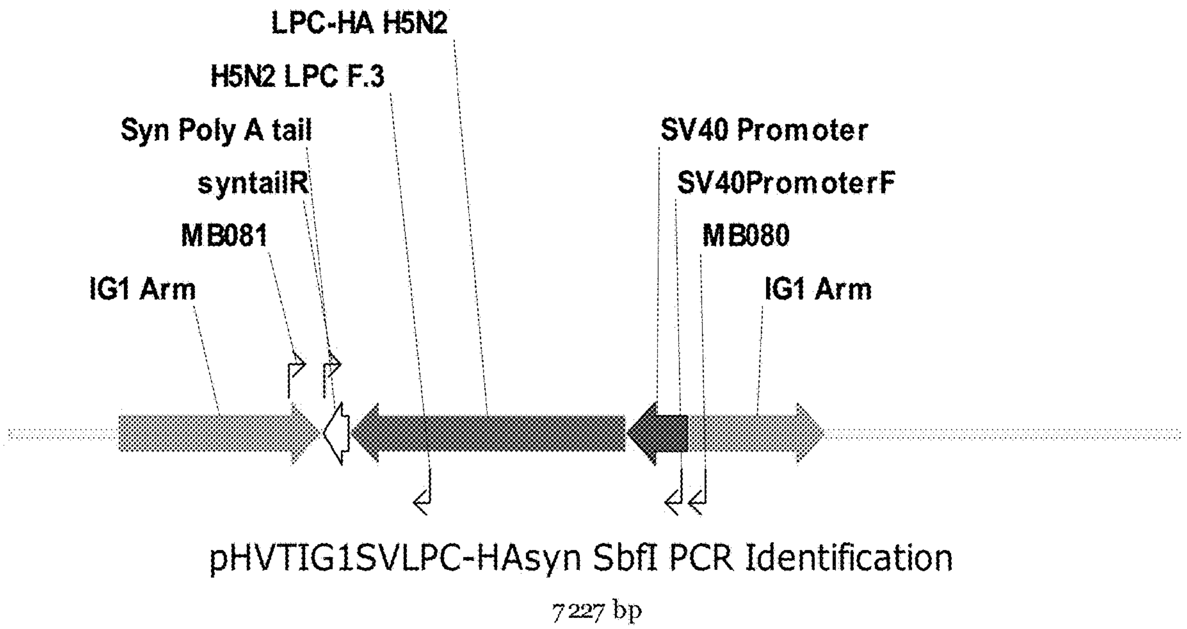
FIG. 5 depicts the schematic representation of primer binding sites.
Figure 6:
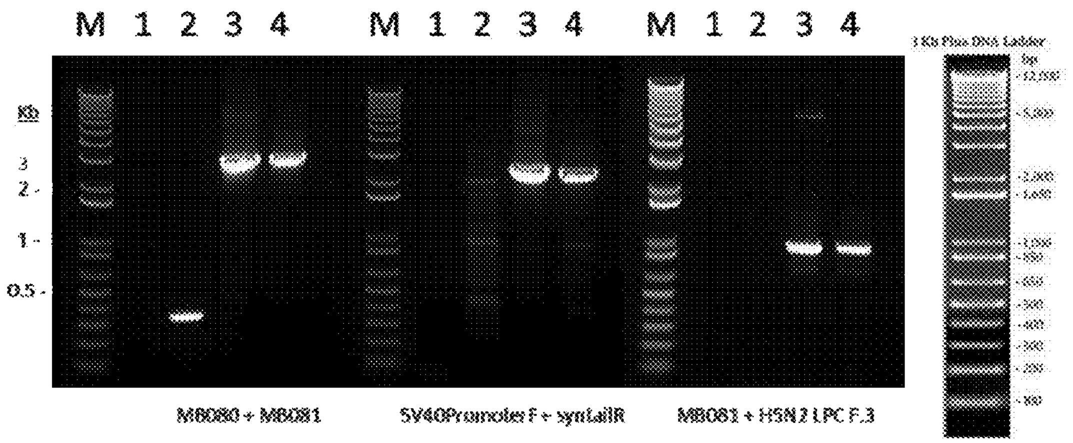
FIG. 6 depicts the PCR results to identify rHVT501.

Purity of recombinant virus was verified by PCR using primer pairs that are specific to the HVT flanking arms, the SV40 promoter, the LPC-HA H5N2 gene and the synthetic poly A tail. The PCR results demonstrate that recombinant virus rHVT501 carries the intended expression cassette and the virus stock is free from detectable amounts of parental HVT virus (Table 1 and FIG. 5-6).

TABLE 1

Primer and expected PCR bands

| primers | HVT FC126 | pHVTIG1SVLPC-HAsyn donor | rHVT501 |
|---|---|---|---|
| MB080 + MB081 | 323 bp | 2593 bp | 2593 bp |
| SV40PromoterF + syntailR | — | 2223 bp | 2223 bp |
| MB081 + H5N2 LPC F.3 | — | 888 bp | 888 bp |

PCR reactions with all primer pairs resulted in the expected PCR products and banding patterns. As shown above, there is no evidence of parental FC126 in rHVT501.

Conclusion

Based on PCR testing and immunofluorescence analysis, rHVT501 is a recombinant HVT expressing an H5N2-HA gene under the control of an SV40 promoter. rHVT501 is free of any detectable parental HVT virus.

Example 1.2

Construction of Recombinant HVT502 Expressing H5N2-HA

The objective of the study is to construct a recombinant HVT virus in which an expression cassette containing a Human Herpesvirus Type III glycoprotein B (HHV3gB) promoter in reverse orientation (ro), a Simian Virus 40 (SV40) promoter, Avian Influenza Virus Hemagglutinin (HA) glycoprotein, and a synthetic poly A tail is inserted in the intergenic site of UL55 in HVT virus (FIG. 2).

The parental virus used in the construct is HVT FC126. An Avian Influenza Virus Heagglutinin (HA) glycoprotein (named LPC-HA) corresponding to H5N2-HA sequence (SEQ ID NO:2 encoded by SEQ ID NO:1, codon-optimized) was chemically synthesized (GenScript). The promoters used are Human Herpesvirus Type III glycoprotein B (HHV3gB) in reverse orientation (ro) and Simian Virus 40 (SV40) promoter. The insertion locus is intergenic site of UL55 (IG1) in HVT (FIG. 2). Donor plasmid pHVTIG1HHV3gBroSVLPC-HAsyn SbfI (an insertion plasmid containing the UL55 flanking regions of HVT virus+HHV3gBro+SV40+synthetic poly A) was constructed as described below. Chicken embryo fibroblast cells (CEF) were used for the in vitro recombination.

Donor Plasmid Construction

Figure 7:
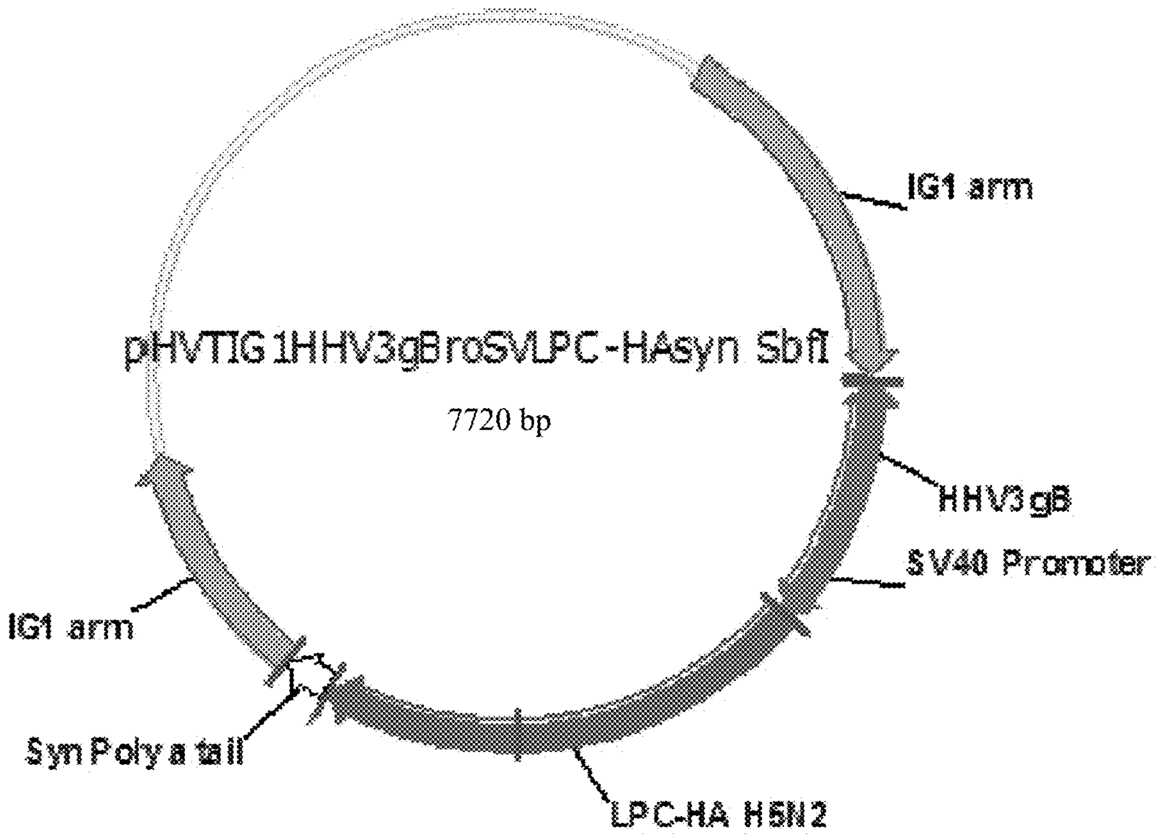
FIG. 7 depicts pHVTIG1HHV3gBroSVLPC-HAsyn SbfI plasmid map.

To construct the donor plasmid pHVTIG1HHV3gBroSVLPC-HAsyn SbfI, a fragment encompassing the synthetic H5N2-HA gene was excised from LPC-HA H5N2 in pUC57 (synthesized by GeneScript) using NotI and inserted into the same site as the pHVTIG1HHV3gBroSVCaFsyn SbfI plasmid (a previously constructed and sequence verified plasmid) containing HHV3gB promoter in the reverse orientation, SV40 promoter, NDV-F gene, and synthetic polyA tail which was also NotI digested and CIP treated, replacing the NDV-F gene with the LPC-HA. The NotI digested insert (LPC-HA) and vector (pHVTIG1) was gel extracted using Qiagens Gel Extraction Kit and then ligated. Ligated material was transformed using Top10 Oneshot kit (cat #C404002, Invitrogen). Bacterial colonies were grown in LBamp broth and plasmid was extracted using Qiagens MiniSpin Prep kit. The plasmids were screened for insert orientation using SmaI digestion. The correct donor plasmid was designated pHVTIG1HHV3gBroSVLPC-HAsyn SbfI. pHVTIG1HHV3gBroSVLPC-HAsyn SbfI mini-prep plasmid was transfected onto one well of a 6-well plate and an IFA was performed using chicken anti-sera against Avian Influenza H5N2 (Charles Rivers Laboratories, Lot #J0210) and anti-chicken FITC (Sigma, Cat #F8888). Once transient expression was verified the plasmid was grown in a larger scale culture and plasmid extraction was done by using Qiagens Maxi Prep kit. This plasmid was sequence verified and designated pHVTIG1HHV3gBroSVLPC-HAsyn SbfI (FIG. 7).

Recombinant Generation

The homologous recombination procedure as described in Example 1.1 was followed to make recombinant rHVT502.

Analysis of Recombinant by PCR

The PCR analysis procedure as described in Example 1.1 was performed to verify rHVT502.

Expression Analysis

The expression analysis described in Example 1.1 was performed to analyze the expression of rHVT502.

Results

The nucleotide and amino acid sequence of the donor plasmid pHVTIG1HHV3gBroSVLPC-HAsyn SbfI are assigned SEQ ID NOs as shown in FIG. 1.

Recombinant Generation and Expression Analyses

Genomic DNA of HVT FC126 virus was co-electroporated with pHVTIG1HHV3gBroSVLPC-HAsyn SbfI donor plasmid to generate recombinant HVT using homologous recombination technique. Recombinant virus was separated from parental HVT virus by immunofluorescent positive well selection and PCR screening in multiple rounds of plaque purification. A plaque purified recombinant HVT virus expressing the LPC-HA H5N2 protein, designated vHVT502, was scaled up from tissue culture flasks to 2×850 $cm^2$ roller bottles. After about 72 hrs post infection the infected CEFs were harvested. Aliquots were frozen in liquid nitrogen containing 10% FBS and 10% DMSO. Titrations were performed in triplicate on CEFs and a titer of $8.25\times10^5$ pfu/ml was obtained for vHVT502.

Figure 8:
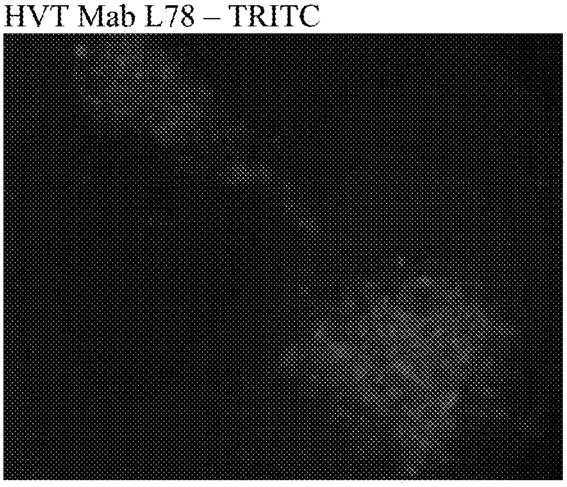
FIG. 8 depicts the dual immunofluorescent staining of recombinant vHVT502 virus expressing LPC-HA H5N2 protein.
Figure 8:
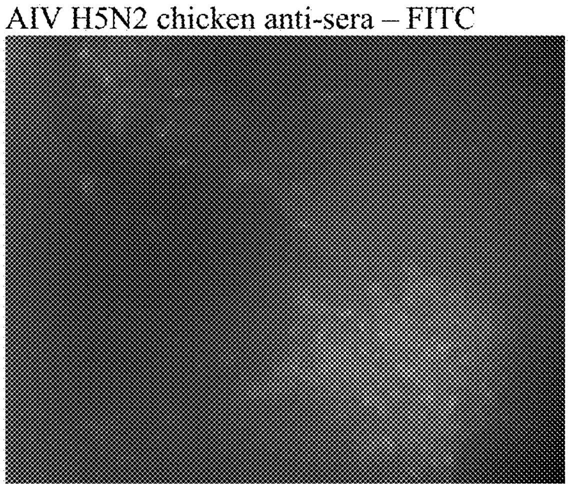

Immunofluorescents was performed using chicken antisera (lot #J0210, Charles Rivers Laboratories) and a monoclonal antibody specific to HVT followed by a FITC labeled anti-chicken IgG (cat #F8888, Sigma) and TRITC labeled anti-mouse IgG (cat #A10037, Life Technologies). All examined plaques of vHVT502 were found to express LPC-HA H5N2 protein (FIG. 8).

PCR Analysis of rHVT502

Figure 9:
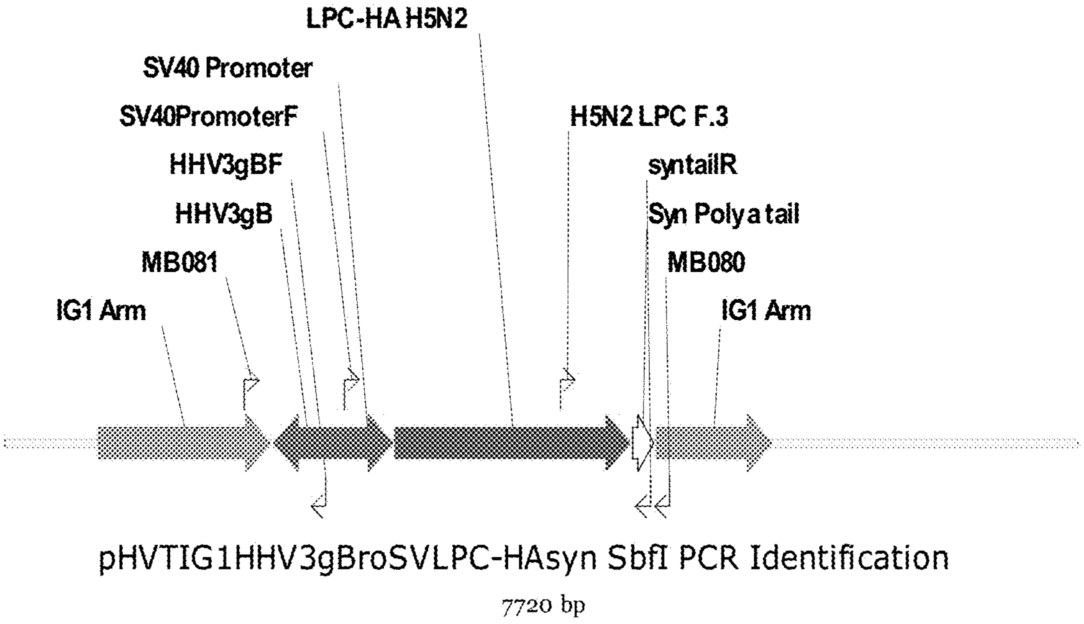
FIG. 9 depicts the schematic representation of primer binding sites.

Purity of recombinant virus was verified by PCR using primer pairs that are specific to the HVT flanking arms, the promoters, the LPC-HA H5N2 gene and the synthetic polyA tail. The PCR results demonstrate that recombinant virus rHVT502 carries the intended expression cassette and the virus stock is free from detectable amounts of parental HVT virus (Table 2 and FIG. 9-10).

TABLE 2

Primers and expected PCR bands

| primers | HVT FC126 | pHVTIG1HHV3gBroSVLPC-HAsyn donor | rHVT501 |
|---|---|---|---|
| MB080 + MB081 | 323 bp | 3086 bp | 3086 bp |
| SV40PromoterF + syntailR | — | 2223 bp | 2223 bp |
| MB081 + H5N2 LPC F.3 | — | 888 bp | 888 bp |
| MB080 + HEIV3gBF | — | 607 bp | 607 bp |

Figure 10:
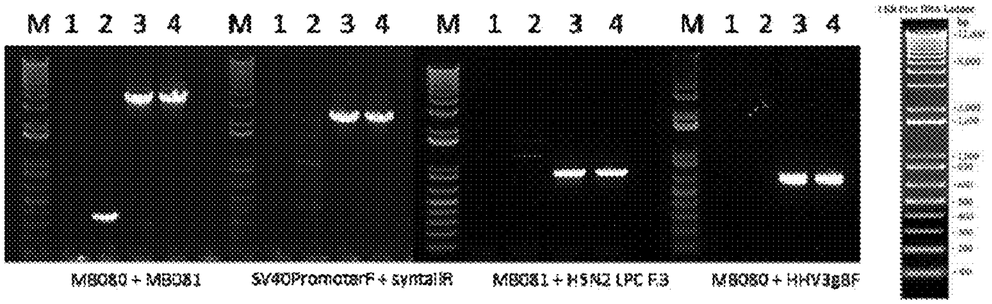
FIG. 10 depicts the PCR results to identify rHVT502.

PCR reactions with all primer pairs resulted in the expected PCR products and banding patterns. As shown in FIG. 10, there is no evidence of parental FC126 in rHVT502.

Conclusion

Based on PCR testing and immunofluorescence analysis, rHVT502 is a recombinant HVT expressing an H5N2-HA gene under the control of a reverse oriented HHV3gB and SV40 promoter. rHVT502 is free of any detectable parental HVT virus.

Example 1.3

Construction of Recombinant HVT503 Expressing Mutant H5N2-HA

The objective of the study is to construct a recombinant HVT virus in which an expression cassette containing Simian Virus 40 (SV40) promoter, Avian Influenza Virus mutant Hemagglutinin (HA) glycoprotein, and a synthetic poly A tail is inserted in the intergenic site of UL55 in HVT virus (FIG. 2).

The parental virus used is HVT FC126. A mutated Avian Influenza Virus Heagglutinin (HA) glycoprotein (named Mut-HA H5N2) corresponding to H5N2-HA sequence (SEQ ID NO:4 encoded by SEQ ID NO:3) was chemically synthesized (GenScript). The H5N2-HA (Mut-HA H5N2) was derived from a highly pathogenic avian influenza A virus (A/chicken/Washington/61-9/2014(H5N2) isolate (GenBank accession No. KP739381.1). The synthetic HA glycoprotein cleavage site of this synthetic gene was altered to match a low pathogenic cleavage site sequence. The H5N2-HA (Mut-HA H5N2) was further modified to include three amino acid mutations S136N, D171N, S239N (or in mature HA protein without signal peptide, S120N, D155N and S223N, Hoffmann, et al., 2005, PNAS, 102(36), p12915-12920).

Simian Virus 40 (SV40) promoter was used in the construct. The insertion locus is intergenic site of UL55 in HVT (Refer to FIG. 2). Donor plasmid_pHVTIG1SVMut-HAsyn SbfI (an insertion plasmid containing the UL55 flanking regions of HVT virus+SV40+synthetic polyA) was prepared as described below. Chicken embryo fibroblast cells (CEF) were used for in vitro recombination.

Donor Plasmid Construction

A fragment encompassing the synthetic H5N2-HA gene was excised from 3 Mut-HA H5N2 in pUC57 (synthesized by GeneScript) using NotI and inserted into the same site as the pHVTIG2SVCaFsyn SbfI plasmid containing SV40 promoter, NDV-F gene, and synthetic polyA tail which was also NotI digested and CIP treated, to replacing the NDV-F gene with the 3 Mut-HA. The NotI digested insert (3 Mut-HA) and vector (pHVTIG2) was gel extracted using Qiagens Gel Extraction Kit and then ligated. Ligated material was transformed using Top10 Oneshot kit (cat #C404002, Invitrogen). Bacterial colonies were grown in LBamp broth and plasmid was extracted using Qiagens MiniSpin Prep kit. The plasmids were screened for insert orientation using SmaI digestion. The correct donor plasmid was designated pHVTIG2SVMut-HAsyn SbfI. pHVTIG2SVMut-HAsyn SbfI mini-prep plasmid was transfected onto one well of a 6-well plate and an IFA was performed using chicken anti-sera against Avian Influenza H5N2 (Charles Rivers Laboratories) and anti-chicken FITC (Sigma, Cat #F8888). Once transient expression was verified the plasmid was grown in a larger scale culture and plasmid extraction was done by using Qiagens Maxi Prep kit.

Figure 11:
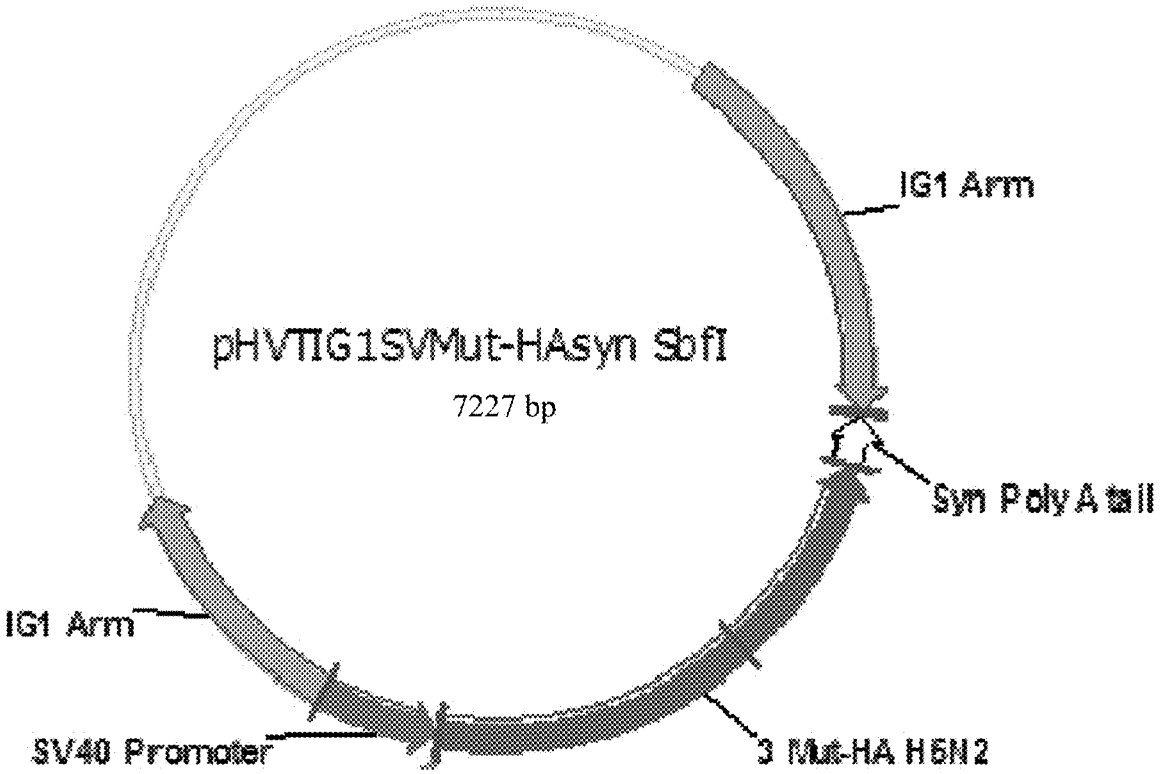
FIG. 11 depicts pHVTIG1SVMut-HAsyn SbfI plasmid map.

An SbfI digest was performed on the pHVTIG2SVMut-HAsyn SbfI maxi prep and pIG1HHV3gBroCaFoptsyn SbfI maxi prep (a previously constructed and sequence verified plasmid). The SV40 H5N2-HA synthetic poly A tail expression cassette flanked by SbfIrestriction enzymes was gel extracted from the pHVTIG2SVMut-HAsyn SbfI plasmid using Qiagens Gel Extraction Kit. The pIG1HHV3gBroCaFoptsyn SbfI vector flanked by SbfI restriction enzymes was also gel extracted and CIP treated. The pHVTIG2SVMut-HAsyn SbfI expression cassette was ligated to the pIG1HHV3gBCaFsyn SbfI vector. Ligated material was transformed using Top10 Oneshot kit (cat #C404002, Invitrogen). Bacterial colonies were grown in LBamp broth and plasmid was extracted using Qiagens MiniSpin Prep kit. The plasmids were screened for insert orientation using EcoRI+SmaI digestion. An anti-genome orientation plasmid was selected, grown in a larger scale culture, and plasmid extraction was done by using Qiagens Maxi Prep kit. This plasmid was sequence verified and designated pHVTIG1SVMut-HAsyn SbfI (FIG. 11).

Recombinant Generation

The homologous recombination procedure described in Example 1.1 was followed to make the recombinant rHVT503.

Analysis of Recombinant by PCR

The PCR procedure described in Example 1.1 was performed to verify rHVT503.

Expression Analysis

The expression analysis procedure described in Example 1.1 was used.

Results

The nucleotide and amino acid sequences of the donor plasmid pHVTIG1SVMut-HAsyn SbfI are assigned SEQ ID NOs as shown in FIG. 1.

Recombinant Generation and Expression Analyses

Genomic DNA of HVT FC126 virus was co-electroporated with pHVTIG1HHV3gBroSVMut-HAsyn SbfI donor plasmid to generate recombinant HVT using homologous recombination technique. Recombinant virus was separated from parental HVT virus by immunofluorescent positive well selection and PCR screening in multiple rounds of plaque purification. A plaque purified recombinant HVT virus expressing the 3 Mut-HA H5N2 protein, designated vHVT503, was scaled up from tissue culture flasks to 2×850 $cm^2$ roller bottles. After about 72 hrs post infection the infected CEFs were harvested. Aliquots were frozen in liquid nitrogen containing 10% FBS and 10% DMSO. Titrations were performed in triplicate on CEFs and a titer of $3\times10^5$ pfu/ml was obtained for vHVT503.

Figure 12:
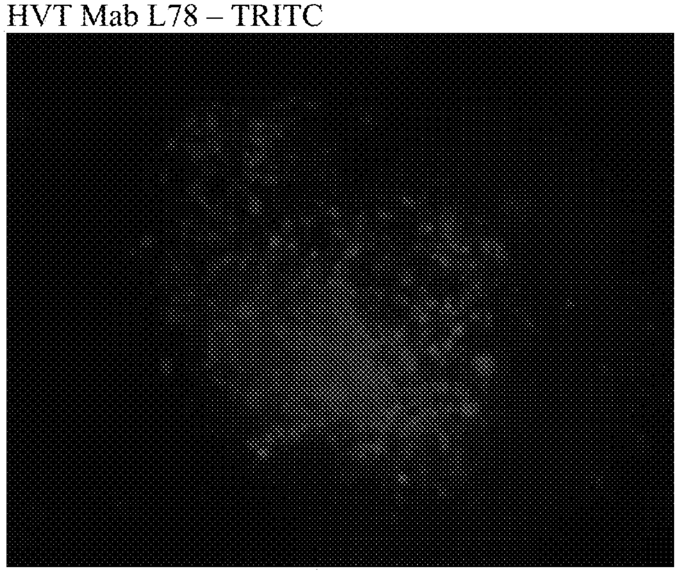
FIG. 12 depicts the dual immunofluorescent staining of recombinant vHVT503 virus expressing 3 Mut-HA H5N2 protein.
Figure 12:
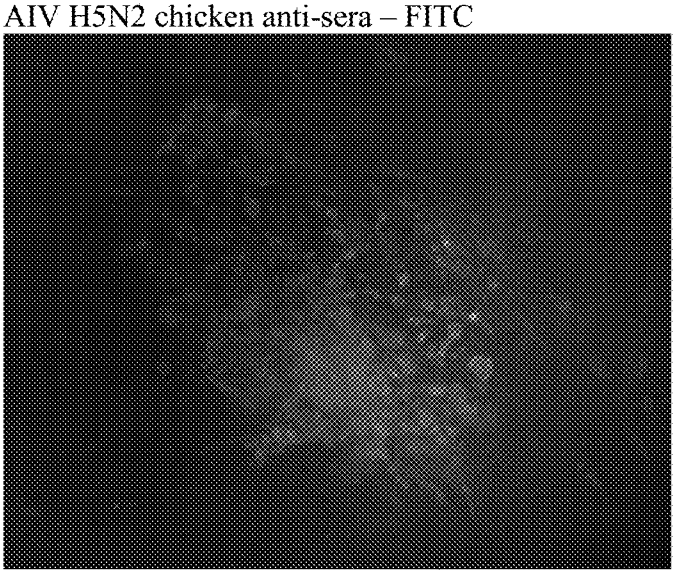

Immunofluorescents was performed using chicken antisera (lot #J0210, Charles Rivers Laboratories) and a monoclonal antibody specific to HVT followed by a FITC labeled anti-chicken IgG (cat #F8888, Sigma) and TRITC labeled anti-mouse IgG (cat #A10037, Life Technologies). All examined plaques of vHVT503 were found to express LPC-HA H5N2 protein (FIG. 12).

PCR Analysis of rHVT503

Figure 13:
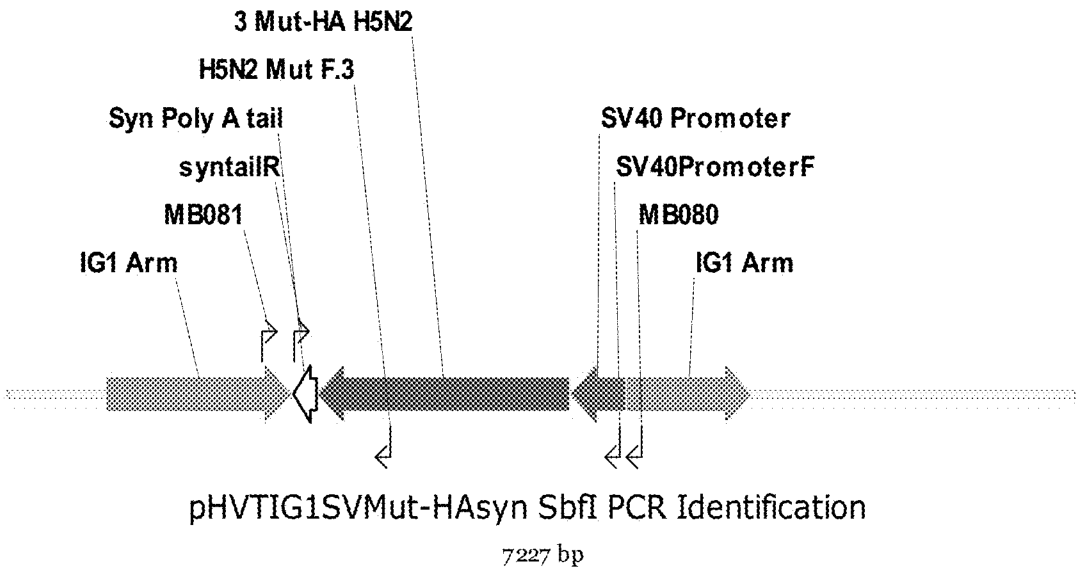
FIG. 13 depicts the schematic representation of primer binding sites.

Purity of recombinant virus was verified by PCR using primer pairs that are specific to the HVT flanking arms, the SV40 promoter, the 3 Mut-HA H5N2 gene, and the synthetic polyA tail. The PCR results demonstrate that recombinant virus vHVT503 carries the intended expression cassette and the virus stock is free from detectable amounts of parental HVT virus (Table 3 and FIGS. 13-14).

TABLE 3

Primer sequences and expected PCR bands

| primers | HVT FC126 | pHVTIG1SVMut-HAsyn donor | rHVT501 |
|---|---|---|---|
| MB080 + MB081 | 323 bp | 2593 bp | 2593 bp |
| SV40PromoterF + syntailR | — | 2223 bp | 2223 bp |
| MB081 + H5N2 LPC F.3 | — | 888 bp | 888 bp |

Figure 14:
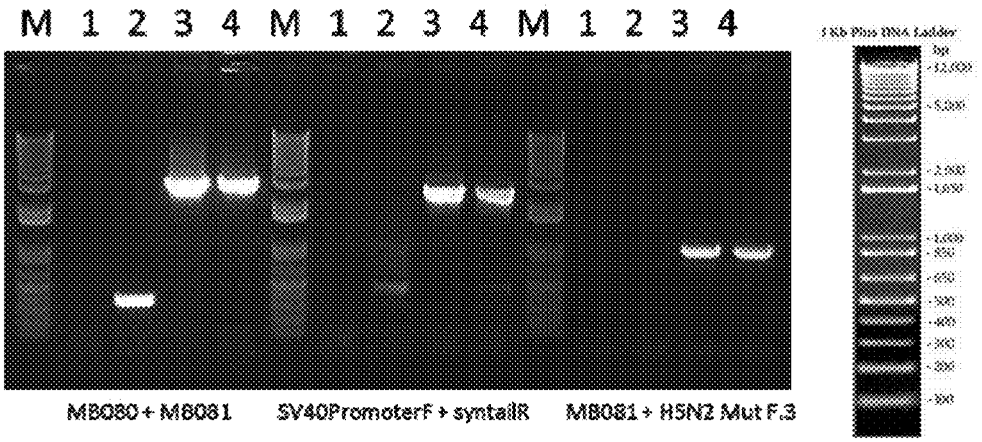
FIG. 14 depicts the PCR results to identify rHVT503.

PCR reactions with all primer pairs resulted in the expected PCR products and banding patterns. As shown in FIG. 14, there is no evidence of parental FC126 in rHVT503.

Conclusion

Based on PCR testing and immunofluorescence analysis, rHVT503 is a recombinant HVT expressing an H5N2-HA gene under the control of an SV40 promoter. rHVT503 is free of any detectable parental HVT virus.

Example 1.4

Construction of Recombinant HVT510 Expressing Mutant H5N2-HA

The objective of the study is to construct a recombinant HVT virus in which an expression cassette containing the mCMV promoter, Avian Influenza Virus mutant Hemagglutinin (HA) glycoprotein, and an SV40 polyA tail is inserted in the intergenic site of UL55 in HVT virus (FIG. 2).

The parental virus used in the construct is HVT FC126. An Avian Influenza Virus Heagglutinin (HA) glycoprotein (named LPC-HA) corresponding to H5N2-HA sequence (SEQ ID NO:2 encoded by SEQ ID NO:17, wild-type DNA, not codon-optimized) was chemically synthesized (GenScript).

The promoter is mCMV promoter (SEQ ID NO:16). The insertion locus is intergenic site of UL55 (IG1) in HVT (FIG. 2). Donor plasmid pCD046-H5N2 HA, an insertion plasmid containing the UL55 flanking regions of HVT virus+mCMV promoter+SV40 polyA (SEQ ID NO:18) was constructed as described below. Chicken embryo fibroblast cells (CEF) were used for in vitro recombination.

In this construct, the expression of H5N2-HA is driven by mCMV promoter and the H5N2-HA gene is wild-type DNA, not codon-optimized. A strong promoter like CMV and codon optimization lead to genetic instability of the construct.

Donor Plasmid Construction

Figure 15A:
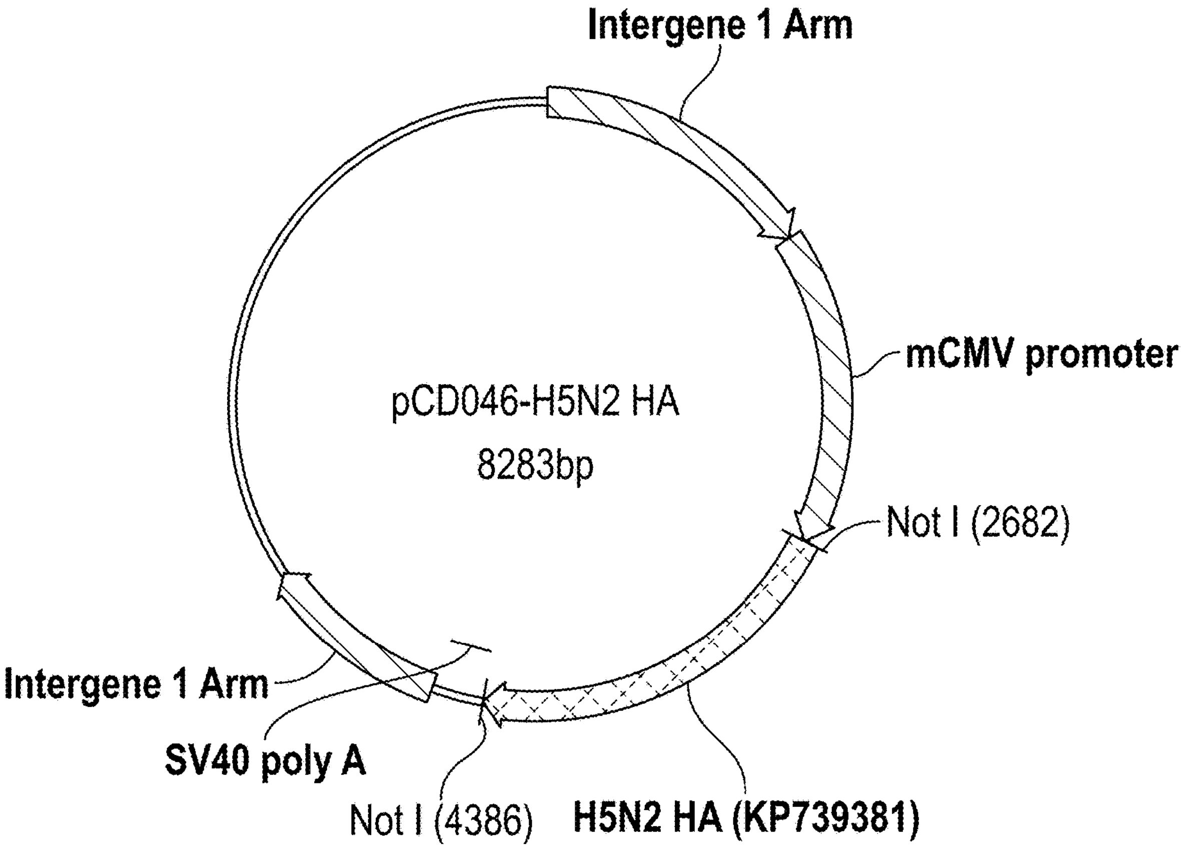
FIG. 15A depicts pCD046-H5N2 HA plasmid map.
Figure 15B:
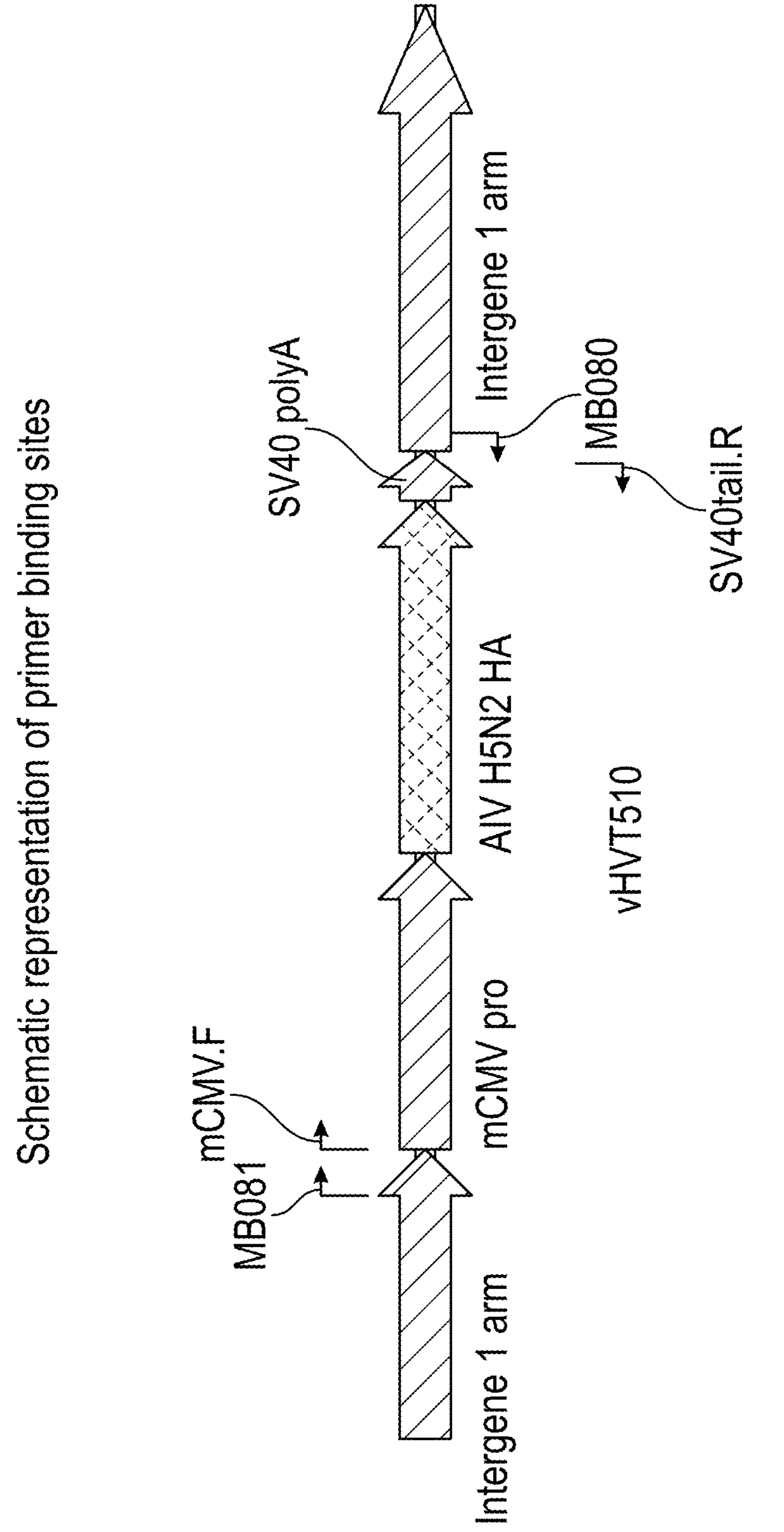
FIG. 15B depicts the schematic representation of primer binding sites.

The H5N2 HA gene (GenBank Accession number-KP739381) (1704 bp) of the "pUC57-H5N2 HA" plasmid (4424 bp) was generated by gene synthesis (GenScript) and cloned into the EcoRV site of pUC57. The donor plasmid, pCD046 was digested with NotI and CIP treated, and the 6.6 kb fragment was gel extracted. The pUC57-H5N2 HA was also digested with NotI and a 1.7 kb fragment containing H5N2 HA was gel extracted. The 6.6 kb and 1.7 kb fragments were ligated to create pCD046-H5N2 HA (see FIG. 15).

Recombinant Generation

The homologous recombination procedure described in Example 1.1 was followed to make the recombinant rHVT510.

PCR Analysis of rHVT510

The PCR procedure described in Example 1.1 was performed to verify rHVT510.

Expression Analysis

The expression analysis procedure described in Example 1.1 was used.

Results

The nucleotide and amino acid sequences of the donor plasmid pHVTIG1SVMut-HAsyn SbfI are assigned SEQ ID NOs as shown in FIG. 1.

Recombinant Virus

After two rounds of plaque purification, pure recombinant virus (rHVT510) was isolated. The rHVT510 was tested by IFA and PCR to validate the appropriate transgene insertion as well as no remnant parental virus. Genetic stability analysis results showed that rHVT510 is stable after more than 12 passages.

PCR Analysis of rHVT510

PCR primers were designed to identify the presence of the AIV H5N2 HA, the mCMV promoter, SV40 polyA tail, the flanking recombination arms of HVT virus. PCR amplifications were preformed using~200 ng of DNA template along with the primer pairs indicated in Table 3.1 and FIG. 15B.

TABLE 3.1

Primer sequences and expected PCR bands

| Primer sets | Expected amplicons (bp) rHVT510 | HVT Fc126 |
|---|---|---|
| MB080 + MB081 | 3649 | 323 |
| mCMV.F + SV40tail.R | 3320 | none |
| SV40pro.F + syntail.R | none | none |

Figure 15C:
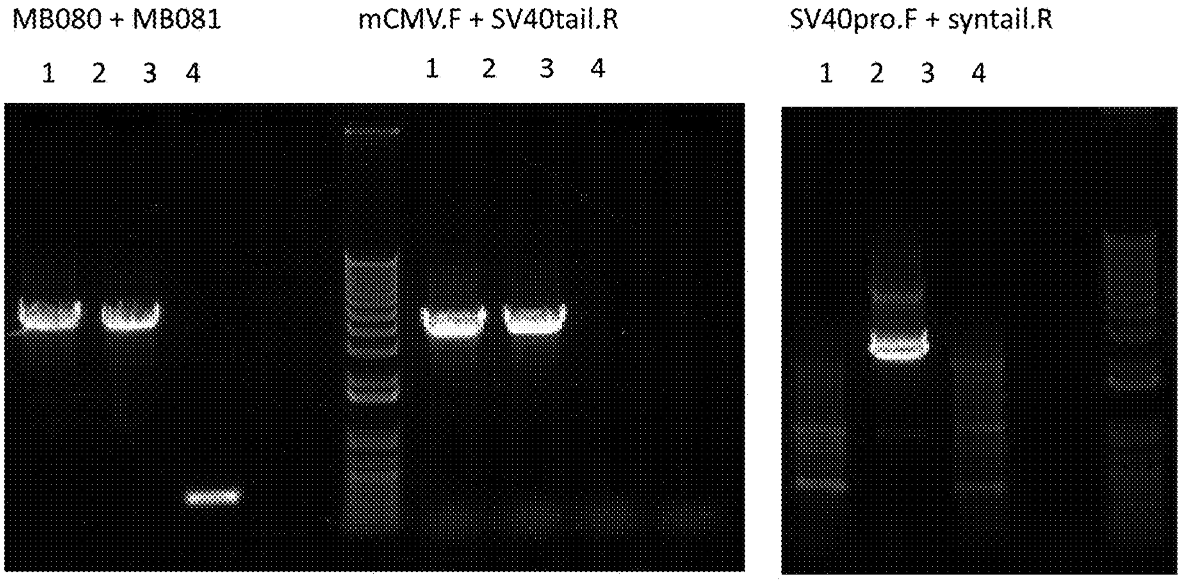
FIG. 15C depicts the PCR results to identify rHVT510.

PCR amplification with various primers listed in Table 3.1 confirmed that rHVT510 has expected amplification pattern and amplicons (FIG. 15C).

It was confirmed that rHVT510 is a recombinant HVT expressing an H5N2-HA gene under the control of an mCMV promoter. rHVT510 is free of any detectable parental HVT virus.

Example 2

Construction of Recombinant Fowlpox Virus Vectors Expressing H5N2-HA

Example 2.1

Construction of Recombinant FPV3003 Expressing H5N2-HA

Figure 16:
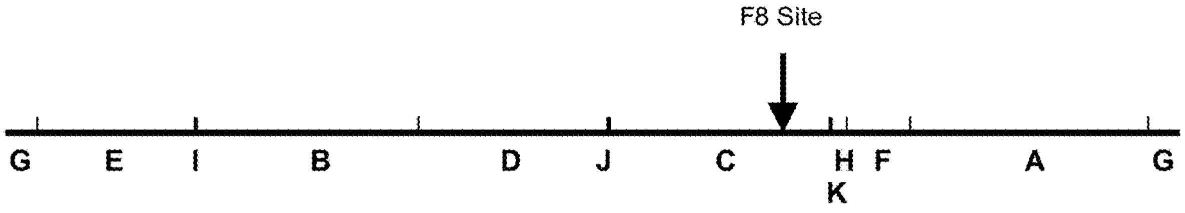
FIG. 16 depicts the schematic representation of the position of the F8 insertion site within the fowlpox virus (TROVAC) genome.

The objective of the study is to construct a recombinant Fowlpox virus in which an expression cassette containing a vaccinia H6 promoter and Avian Influenza Virus Hemagglutinin (HA) glycoprotein replacing the FPV158 CDS (also known as F8) in Fowlpox virus (FIG. 16).

The parental virus used in the construct is attenuated Fowlpox virus (TROVAC). An Avian Influenza Virus Heagglutinin (HA) glycoprotein corresponding to H5N2-HA sequence (SEQ ID NO:2 encoded by SEQ ID NO:1) was chemically synthesized (GenScript). The HA glycoprotein cleavage site of this synthetic gene was altered to match a low pathogenic cleavage site sequence.

The promoter is vaccinia H6 (H6) promoter (SEQ ID NO:11). The insertion locus is FPV158 CDS (F8) replacement. Donor plasmid_pF8 H6pLPC-HA H5N2 (a plasmid containing the FPV158 (F8) flanking regions of Fowlpox virus+H6) was constructed as described below. Chicken embryo fibroblast cells (CEF) were used for in vitro recombination.

Donor Plasmid Construction

Figure 17:
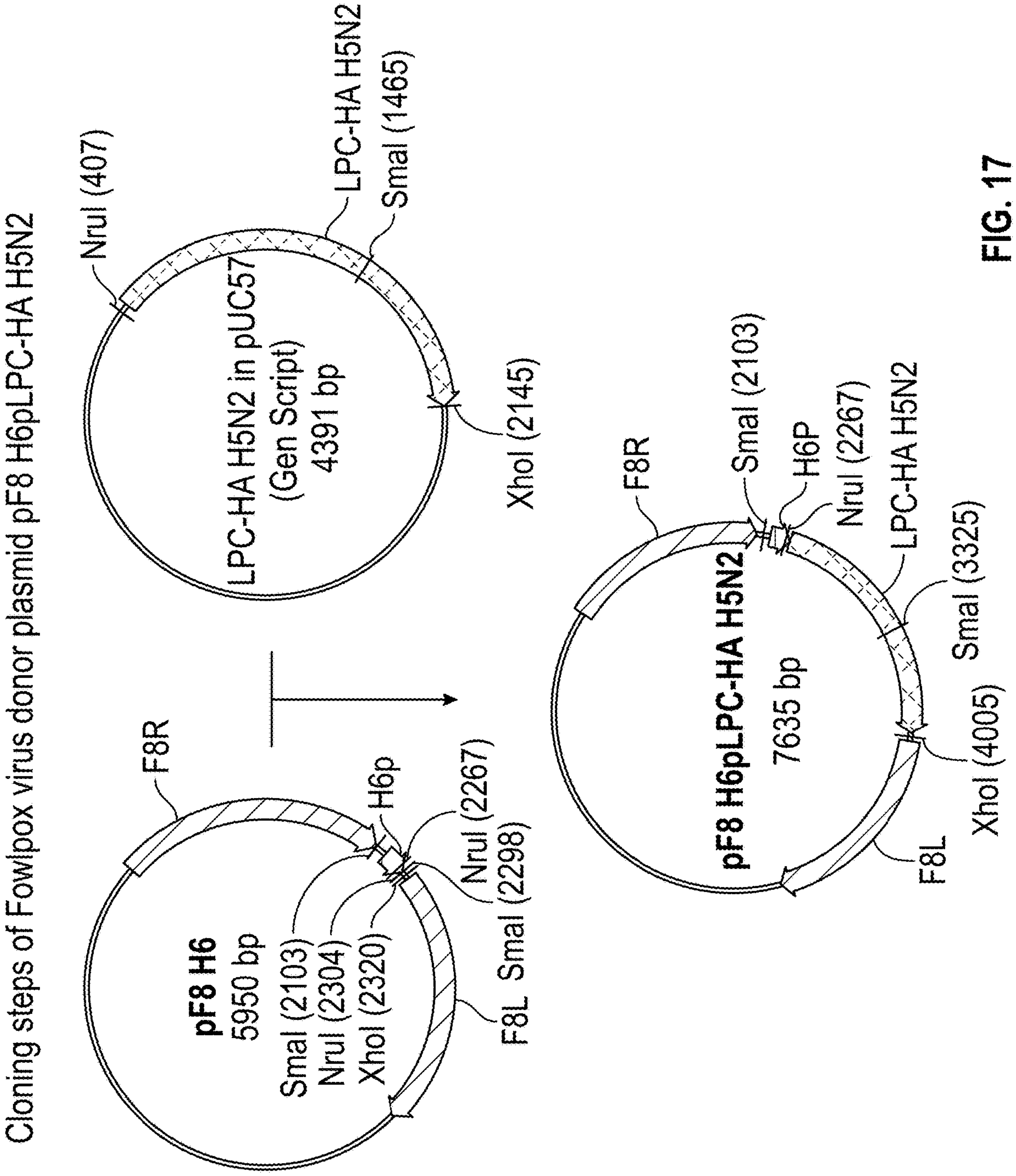
FIG. 17 depicts the cloning steps of fowlpox virus donor plasmid pF8 H6pLPC-HA H5N2.

A fragment encompassing the synthetic H5N2-HA gene was excised from LPC-HA H5N2 in pUC57 (synthesized by GeneScript) using NruI and XhoI and inserted into the same site as the pF8 H6p plasmid (a previously constructed and sequence verified plasmid, Merial) containing H6 promoter (FIG. 17) which was also NruI and XhoI digested. The NruI and XhoI digested insert (LPC-HA) and vector (pF8 H6) were gel extracted using Qiagens Gel Extraction Kit and then ligated. Ligated material was transformed using Top10 Oneshot kit (cat #C404002, Invitrogen). Bacterial colonies were grown in LBamp broth and plasmid was extracted using Qiagens MiniSpin Prep kit. Six miniprep plasmids were screened for the insert using SmaI digestion. All miniprep plasmids had the expected restriction endonuclease pattern. Miniprep #1 was grown in a larger scale culture and plasmid extraction was done by using Qiagens Maxi Prep kit. This plasmid was sequence verified and designated pF8 H6pLPC-HA H5N2.

Recombinant Generation

The homologous recombination procedure as described in Example 1.1 was followed to make recombinant rFPV3003.

Analysis of Recombinant by PCR

The PCR analysis procedure as described in Example 1.1 was performed to verify rFPV3003.

Expression Analysis

The expression analysis described in Example 1.1 was performed to analyze the expression of rFPV3003.

Results

The nucleotide and amino acid sequences of the donor plasmid pF8 H6pLPC-HA H5N2 are assigned SEQ ID NOs as shown in FIG. 1.

Using immunofluorescence technique as described above, recombinant plaques were found to express the hemagglutinin gene of H5N2.

Figure 18:
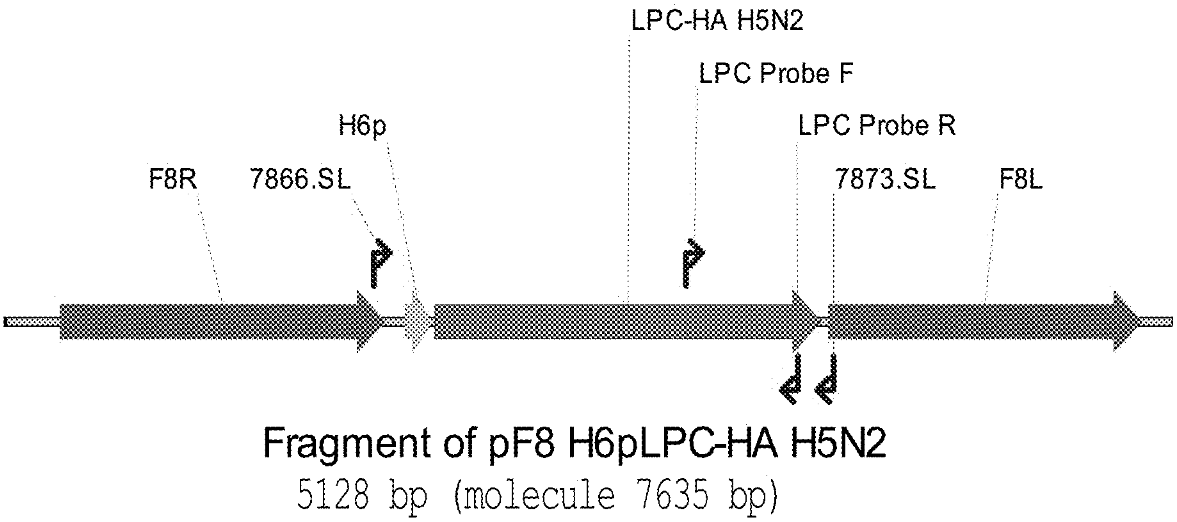
FIG. 18 depicts the schematic representation of primer binding sites for plasmid pF8 H6pLPC-HA H5N2.
Figure 19:
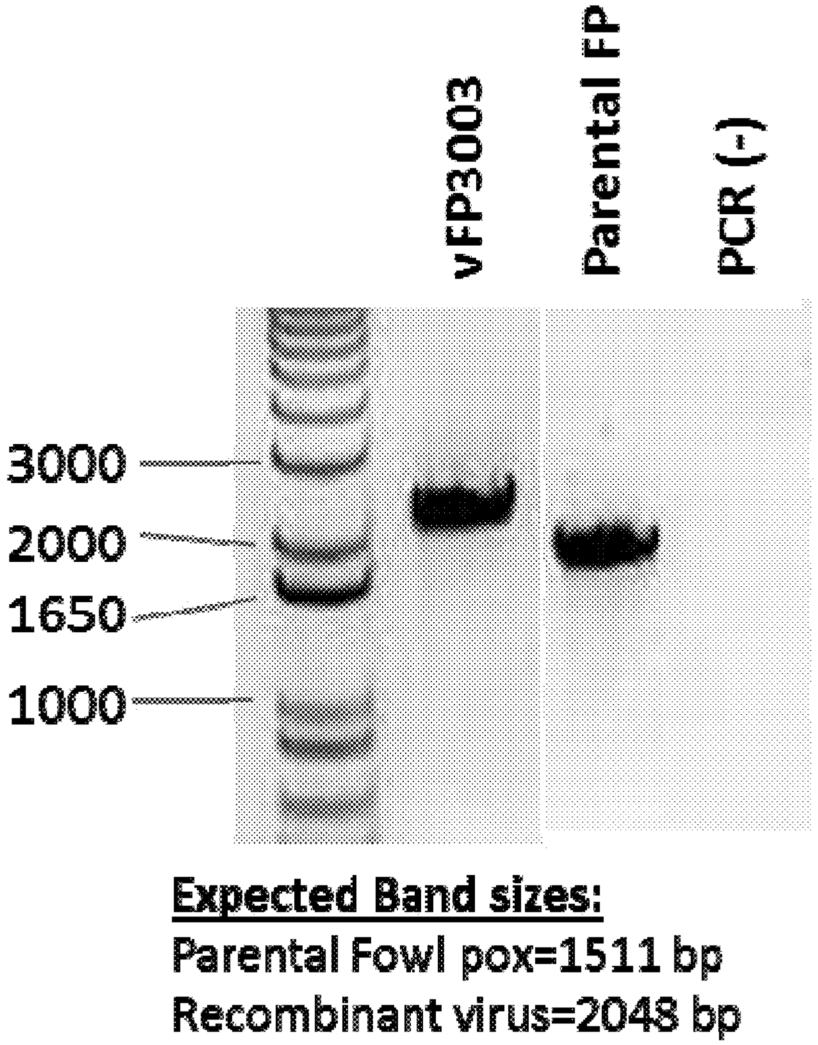
FIG. 19 depicts the PCT results to identify rFPV3003.

Purity of recombinant virus was verified by PCR using primer pairs that are specific to the fowl pox flanking arms (FIG. 18). The PCR results demonstrate that recombinant virus rFP3003 carries the intended expression cassette and the virus stock is free from detectable amounts of parental fowl pox virus (FIG. 19).

Conclusion

Based on PCR testing and immunofluorescence analysis, rFPV3003 is a recombinant FPV expressing an H5N2-HA gene under the control of the vaccinia H6 promoter. rFPV3003 is free of any detectable parental FPV.

Example 2.2

Construction of Recombinant FP3004 Expressing Mutant H5N2-HA

The objective of the study is to construct a recombinant Fowlpox virus in which an expression cassette containing a vaccinia H6 promoter and Avian Influenza Virus Hemagglutinin (HA) glycoprotein replacing the FPV158 CDS in Fowlpox virus (FIG. 16).

The parental virus used is attenuated Fowlpox virus (TROVAC). An Avian Influenza Virus Heagglutinin (HA) glycoprotein corresponding to mutant H5N2-HA sequence (SEQ ID NO:4 encoded by SEQ ID NO:3) was chemically synthesized (GenScript). The HA glycoprotein cleavage site of this synthetic gene was altered to match a low pathogenic cleavage site sequence.

Vaccinia H6 (H6) promoter was used in the construct. The insertion locus is FPV158 CDS replacement (F8). Donor plasmid pF8 H6p3Mut-HA H5N2 (a plasmid containing the FPV158 (F8) flanking regions of Fowlpox virus+H6) was prepared as described below. Chicken embryo fibroblast cells (CEF) were used for in vitro recombination.

Donor Plasmid Construction

Figure 20:
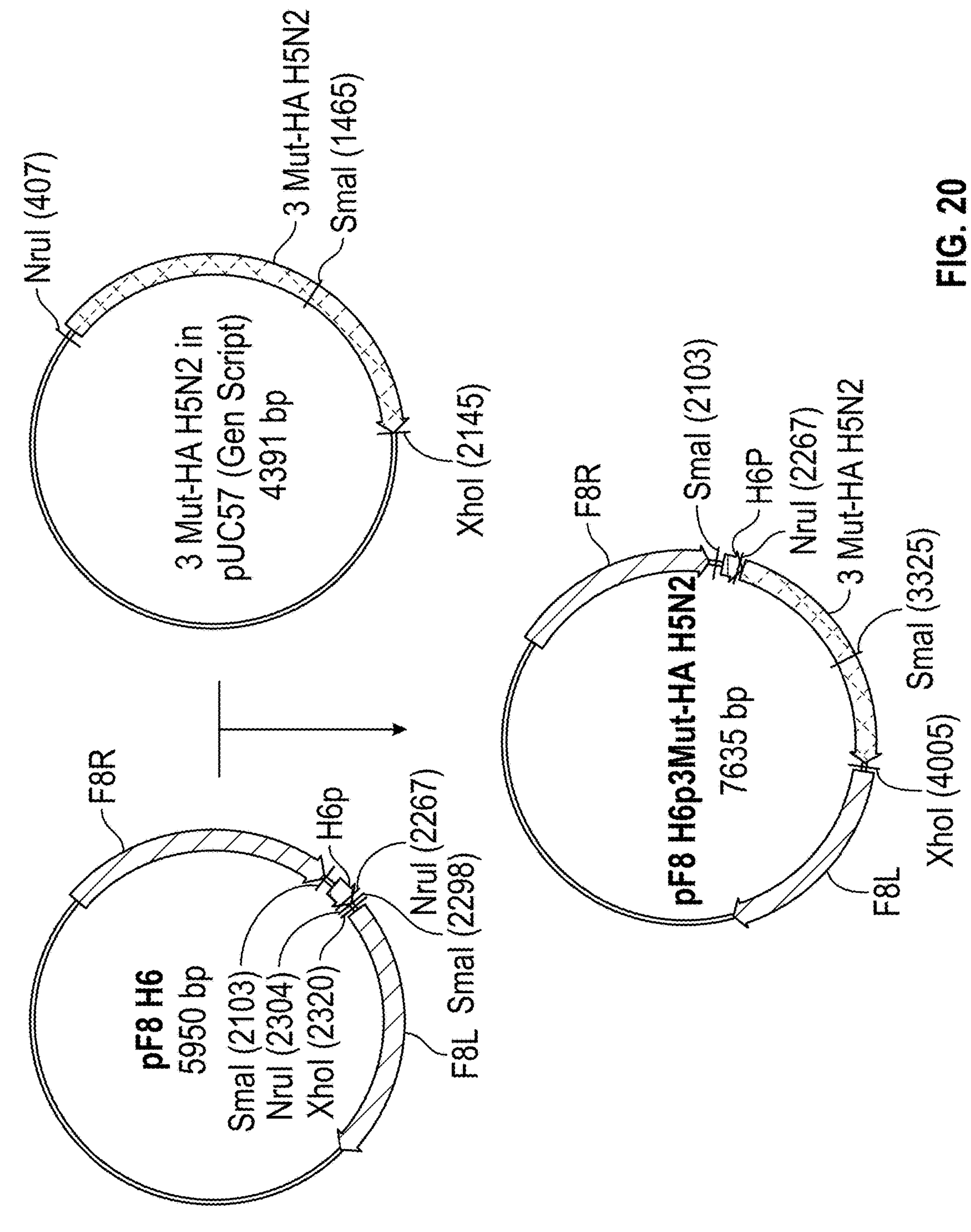
FIG. 20 depicts the cloning steps of fowlpox virus donor plasmid pF8 H6p3Mut-HA H5N2.

A fragment encompassing the synthetic mutant H5N2-HA gene was excised from 3 Mut-HA H5N2 in pUC57 (synthesized by GeneScript) using NruI and XhoI and inserted into the same site as the pF8 H6p plasmid (Merial) containing H6 promoter (FIG. 20) which was also NruI and XhoI digested. The NruI and XhoI digested insert (3 Mut-HA) and vector (pF8 H6) were gel extracted using Qiagens Gel Extraction Kit and then ligated. Ligated material was transformed using Top10 Oneshot kit (cat #C404002, Invitrogen). Bacterial colonies were grown in LBamp broth and plasmid was extracted using Qiagens Mini Spin Prep kit. Six miniprep plasmids were screened for the insert using SmaI digestion. All miniprep plasmids had the expected restriction endonuclease pattern. Miniprep #1 was grown in a larger scale culture and plasmid extraction was done by using Qiagens Maxi Prep kit. This plasmid was sequence verified and designated pF8 H6p3Mut-HA H5N2.

Recombinant Generation

The homologous recombination procedure as described in Example 1.1 was followed to make recombinant rFP3004.

Analysis of Recombinant by PCR

The PCR analysis procedure as described in Example 1.1 was performed to verify rFP3004.

Expression Analysis

The expression analysis described in Example 1.1 was performed to analyze the expression of rFP3004.

Results

The nucleotide and amino acid sequences of the donor plasmid pF8 H6p3Mut-HA H5N2 are assigned SEQ ID NOs as shown in FIG. 1.

Using immunofluorescence technique as described above, recombinant plaques were found to express the hemagglutinin gene of H5N2.

Figure 21:
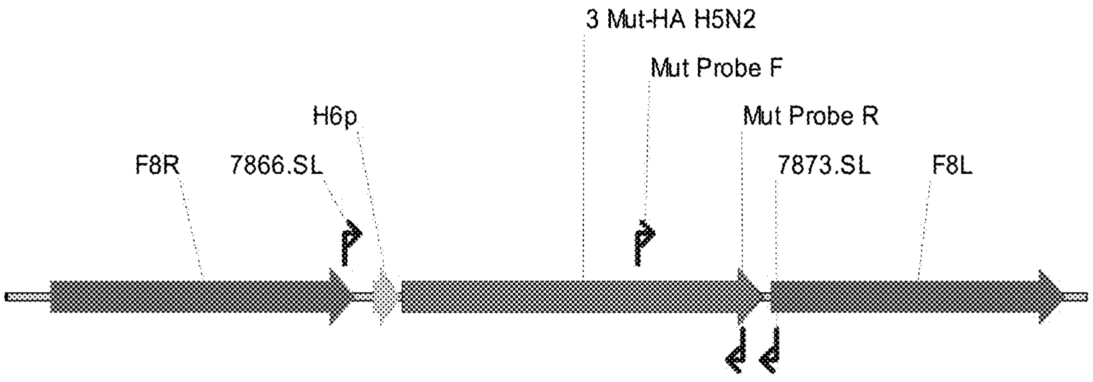
FIG. 21 depicts the schematic representation of primer binding sites for plasmid plasmid pF8 H6p3Mut-HA H5N2.
Figure 22:
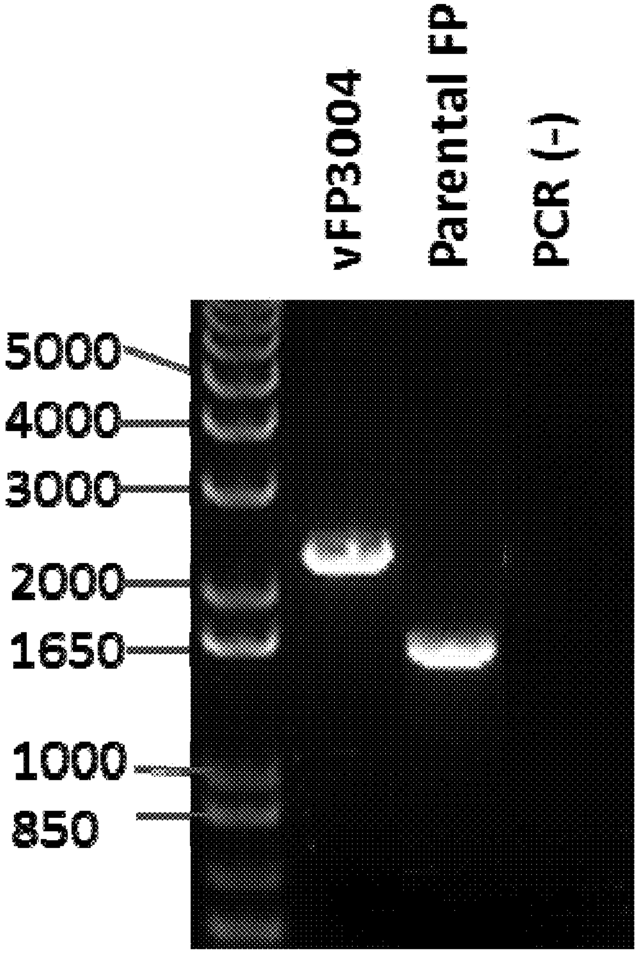
FIG. 22 depicts the PCT results to identify rFPV3004.

Purity of recombinant virus was verified by PCR using primer pairs that are specific to the fowlpox flanking arms (FIG. 21). The PCR results demonstrate that recombinant virus rFP3004 carries the intended expression cassette and the virus stock is free from detectable amounts of parental fowlpox virus (FIG. 22).

Conclusion

Based on PCR testing and immunofluorescence analysis, rFPV3004 is a recombinant FPV expressing a mutant H5N2-HA gene under the control of the vaccinia H6 promoter. rFPV3004 is free of any detectable parental FPV.

Example 3

Immunogenicity and Challenge Studies in SPF Chickens

Immunogenicity and challenge studies were conducted in specific pathogen free (SPF) chickens vaccinated subcutaneous, 0.2 ml per chick, 3100 pfu/dose, at one day of age with HVT-AIV recombinant vaccines. Twenty chickens were assigned to each vaccine group (see Table 4). A group vaccinated with diluent only was included as a challenge control.

TABLE 4

Vaccination scheme

| Group | Vaccines |
|---|---|
| SHAM(1)[a] | Diluent only |
| rHVT-501(1)[a] | rHVT-501 vector |
| rHVT-502(2)[b] | rHVT-502 vector |
| rHVT-503(2)[b] | rHVT-503 vector |
| SHAM(2)[b] | Diluent only |

[a]rHVT-501: Study 1

[b]rHVT-502; rHVT-503: Study 2

Challenge Study

One-day-old chickens were vaccinated according to Table 4. At 4 weeks of age, chickens were challenged with Tk/MN/12582/15 H5N2 at $10^{6.0}$ $EID_{50}$ per chicken. After challenge, the chickens were observed daily for morbidity and mortality, and the morbid chickens were counted as infected with influenza. Oropharyngeal swabs to determine challenge virus shedding from respiratory tract were collected at 2 and 4 days post-challenge (DPC) in 1.5 ml of brain heart infusion (BHI) medium (Becton-Dickinson, Sparks, Md.) containing antimicrobial compounds (100m/mL gentamicin, 100 units/mL penicillin, and 5 μg/mL amphotericin B). Remaining chickens from all groups were bled for serum collection at days 42 and 56 of age. The birds were euthanized with intravenous sodium pentobarbital (100 mg/kg body weight) at 56 days of age.

As shown in Tables 5 and 6, for the groups challenged with Tk/MN/12582/15 H5N2, surprisingly, rHVT501 expressing the H5N2 HA (LPC-HA H5N2) provided better protection in chickens than rHVT503 which contains the mutant H5N2 HA gene. rHVT501 gave 100% protection against clinical disease, while rHVT502 and rHVT 503 gave 45-50% and 15% protection against clinical disease, respectively. All three rHVT recombinant vaccines provided protection against avian influenza virus infections compared to the controls.

TABLE 5

Results of rHVT-AIV efficacy - number of birds survived after challenge

| Days post inoculation | SHAM(1) | rHVT-501(1) | rHVT-502(2) | rHVT-503(2) | SHAM(2) |
|---|---|---|---|---|---|
| 0 | 20 | 19 | 20 | 20 | 20 |
| 1 | 20 | 19 | 20 | 20 | 20 |
| 2 | 6 | 19 | 11 | 5 | 5 |
| 3 | 3 | 19 | 10 | 3 | 1 |
| 4 | 1 | 19 | 10 | 3 | 0 |
| 5 | 1 | 19 | 10 | 3 | 0 |
| 6 | 1 | 19 | 9 | 3 | 0 |
| 7 | 1 | 19 | 9 | 3 | 0 |
| 8 | 1 | 19 | 9 | 3 | 0 |
| 9 | 1 | 19 | 9 | 3 | 0 |
| 10 | 1 | 19 | 9 | 3 | 0 |
| 11 | 1 | 19 | 9 | 3 | 0 |
| 12 | 1 | 19 | 9 | 3 | 0 |
| 13 | 1 | 19 | 9 | 3 | 0 |
| 14 | 1 | 19 | 9 | 3 | 0 |

TABLE 6

Results of rHVT-AIV efficacy - percent survival after challenge

| Days post inoculation | SHAM(1) | rHVT-501(1) | rHVT-502(2) | rHVT-503(2) | SHAM(2) |
|---|---|---|---|---|---|
| 0 | 100 | 100 | 100 | 100 | 100 |
| 1 | 100 | 100 | 100 | 100 | 100 |
| 2 | 30 | 100 | 55 | 25 | 25 |
| 3 | 15 | 100 | 50 | 15 | 5 |
| 4 | 5 | 100 | 50 | 15 | 0 |
| 5 | 5 | 100 | 50 | 15 | 0 |
| 6 | 5 | 100 | 45 | 15 | 0 |
| 7 | 5 | 100 | 45 | 15 | 0 |
| 8 | 5 | 100 | 45 | 15 | 0 |
| 9 | 5 | 100 | 45 | 15 | 0 |
| 10 | 5 | 100 | 45 | 15 | 0 |
| 11 | 5 | 100 | 45 | 15 | 0 |
| 12 | 5 | 100 | 45 | 15 | 0 |
| 13 | 5 | 100 | 45 | 15 | 0 |
| 14 | 5 | 100 | 45 | 15 | 0 |

Viral shedding was investigated using quantitative RT-PCR test on oropharynx and cloacal swabs samples taken from survivor birds at 2 and 4 dpc. The swabs were tested by quantitative real time reverse transcriptase polymerase chain reaction (qRRT-PCR) for avian influenza virus, and qRRT-PCR cycle threshold values were converted to equivalent infectious titers in embryonating chicken eggs based on regression line produced using a challenge virus dilution series (Lee et al., Journal of Virological Methods 119(2): 151-158). Briefly, RNA was extracted from oropharyngeal swab material by adding 250 μl of swab medium to 750 μl of Trizol LS (Invitrogen Inc., Carlsbad, Calif.), followed by mixing via vortexing, incubation at room temperature for 10 min, and then 200 μl of chloroform was added. The samples were vortexed again, incubated at room temperature for 10 min, and then centrifuged for 15 min at approximately 12,000×g. The aqueous phase was collected and RNA isolated with the MagMAX AI/ND viral RNA isolation kit (Ambion, Inc. Austin Tex.) in accordance with the kit instructions using the KingFisher magnetic particle processing system (Thermo Scientific, Waltham, Mass.). The avian influenza virus challenge strains were used to produce the RNA for the quantitative standard. Allantoic fluid virus stocks were diluted in BHI broth (Becton-Dickinson) and titrated in embryonating chicken eggs at the time of dilution as per standard methods (Swayne et al., 2008, Avian influenza. In: Isolation and Identification of Avian Pathogens. 5th ed., pp. 128-134). Whole virus RNA was extracted from ten-fold dilutions of titrated virus as described for swab material. qRRT-PCR for the influenza matrix gene was performed as previously described (Lee et al., 2004). Virus titers in samples were calculated based on the standard curves, either calculated by the Smart Cycler II (Cepheid, Inc. Sunnyvale, Calif.) software or extrapolation of the standard curve equation.

In addition to providing 100% protection against clinical disease, rHVT501 also reduced virus shedding significantly as determined by the virus copy number in 10 ul swab material as shown in FIG. 23.

Example 4

Immunogenicity and Challenge Studies in SPF Chickens Against Homologous and Heterologous AIV Challenges The goal of the study is to determine efficacy of rHVT501 and rHVT510 administered to one-day-old SPF chickens, against challenge with two (homologous and heterologous) high-pathogenicity Avian Influenza Virus (HPAIV) strains.

Seventy-two one-day-old chickens were separated into 6 groups (see Table 7). The study was carried out according to the timeline outlined in Table 8.

TABLE 7

Study groups

| Group | Vaccine PFU/dose | Route/ Volume (ml) | Number Of Birds Placed | Number Of Birds at Challenge | H5 challenge* |
|---|---|---|---|---|---|
| 1 | rHVT501 ~2,200 | 0.2 ml/SQ | 12 | 10 | [Minnesota/ 12582] |
| 2 | rHVT510 ~2,100 | 0.2 ml/SQ | 12 | 10 | [Minnesota/ 12582] |
| 3 | Sham-Vaccinated Negative Controls | 0.2 ml/SQ | 12 | 10 | [Minnesota/ 12582] |
| 4 | rHVT501 ~2,200 | 0.2 ml/SQ | 12 | 10 | Heterologous |
| 5 | rHVT510 ~2,100 | 0.2 ml/SQ | 12 | 10 | Heterologous |
| 6 | Sham-Vaccinated Negative Controls | 0.2 ml/SQ | 12 | 10 | Heterologous |

*The birds were challenged on Study Day 28, with one of two strains of HPAIV H5: "Homologous" A/turkey/Minnesota/12582/2015; Clade 2.3.4.4; [Minnesota/12582]; or "Heterologous" - (A/Egypt/N04915/2014, H5N1), by the intrachoanal route, with ~$10^{6.0}$ $EID_{50}$ per dose.

TABLE 8

| Study timeline | |
|---|---|
| Study Day or Range | Activity |
| Day 0 | All birds were vaccinated or sham-vaccinated by the SQ route. |
| Days 16-25 | All groups were reduced to ten (10) birds and neck banded for individual identification with numbered bands. |
| Days 25-28 | Blood was collected via venipuncture from the wing or jugular vein. |
| Day 28 | All the birds were challenged with HPAIV by the intrachoanal route, 0.1 ml per bird. |
| Day 28-42 | The birds were observed daily for any unfavorable reactions to the challenge. |
| Day 30* | Oropharyngeal and/or cloacal swabs were collected from all birds (including birds found dead on this study day) and stored in brain and heart infusion media (BHI) at −70° C. until molecular testing to determine virus shedding was conducted. |
| Day 32* | Oropharyngeal and/or cloacal swabs were collected from all birds (including birds found dead on this study day) and stored in brain and heart infusion media (BHI) at −70° C. until molecular testing to determine virus shedding was conducted. |
| Day 42 | Blood was collected from all the remaining birds and the birds were terminated. |

*Swabs samples were collected only on Study Days 30 and 32, from all birds alive on these days and also from birds found dead on these particular study days. Any other birds that are found dead or are euthanized on any other study day were not sampled.

All birds were observed for typical HPAIV clinical signs, including mortality for 14 days post-challenge. The clinical signs include: severe depression, nervous or respiratory system signs and/or death. At the end of the observation period (Study Day 42), the survivors will be bled for serology and terminated.

The serum collected pre and post-challenge were used in hemagglutination inhibition (HI) assays to determine the antibody levels against selected AIV strains. An aliquot of the pre-challenge serum was also used for cross-neutralization tests.

HPAIV viral load was tested by real time RT-PCR in the collected swabs following routine procedures. Viral RNA was extracted using MagMAX™-96 AI/ND Viral RNA Isolation Kit® (Ambion, Inc.) following the manufacturer's instructions. The resulting viral RNA extracts were quantified by one-step qRRT-PCR which targets the influenza matrix gene using 7500 FAST Real-time PCR System (Applied Biosystems, Foster City, Calif., USA). The standard curves for viral RNA quantification were established with RNA extracted from dilutions of the same titrated stocks of the challenge viruses. For analysis, all the negative samples were considered to be lower than the limit of detection established for each virus.

Results

The mortality results are shown in Table 9 below. The results demonstrated that both rHVT501 and rHVT510 provided 100% protection against homologous AIV challenges, rHVT510 provided 100% protection against heterologous MV challenges and rHVT501 provided 90% protection against heterologous AIV challenges.

TABLE 9

| Number of birds positive for HPAIV and percent protection/infection by Group | | | | |
|---|---|---|---|---|
| Group | Vaccine PFU/dose* | H5 challenge** | # Positive/ Total # birds | % Protection (% Infection) |
| 1 | rHVT501 2,200 | Minnesota/ 12582 | 0/10 | 100 |
| 2 | rHVT510 2,100 | Minnesota/ 12582 | 0/10 | 100 |
| 3 | Sham- Vaccinated Negative Controls | Minnesota/ 12582 | 10/10 | (100%) |
| 4 | rHVT501 2,200 | Egypt/2014 | 1/10 | 90 |
| 5 | rHVT510 2,100 | Egypt/2014 | 0/10 | 100 |
| 6 | Sham- Vaccinated Negative Controls | Egypt/2014 | 10/10 | (100%) |

*All birds were challenged on Study Day 28, by the intrachoanal route with A/turkey/Minnesota/12582/2015; Clade 2.3.4.4; [Minnesota/12582], at $10^{6.9}$ $EID_{50}$ per dose (Groups 1-3) or A/Egypt/N04915/2014, H5N1, clade 2.2.1; [Egypt/2014], at $10^{5.7}$ $EID_{50}$ per dose (Groups 4-6).

Figure 23A:
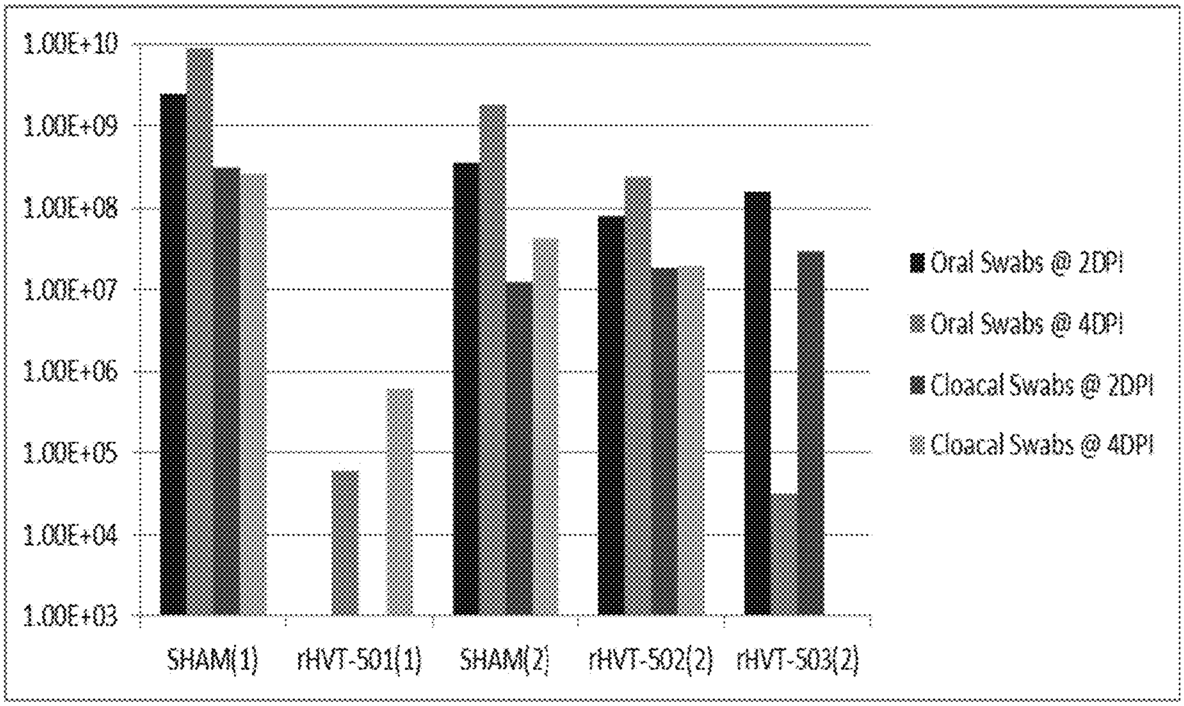
FIG. 23A depicts the rHVT-H5 virus shedding data in RNA copy number/10 ul.
Figure 23B:
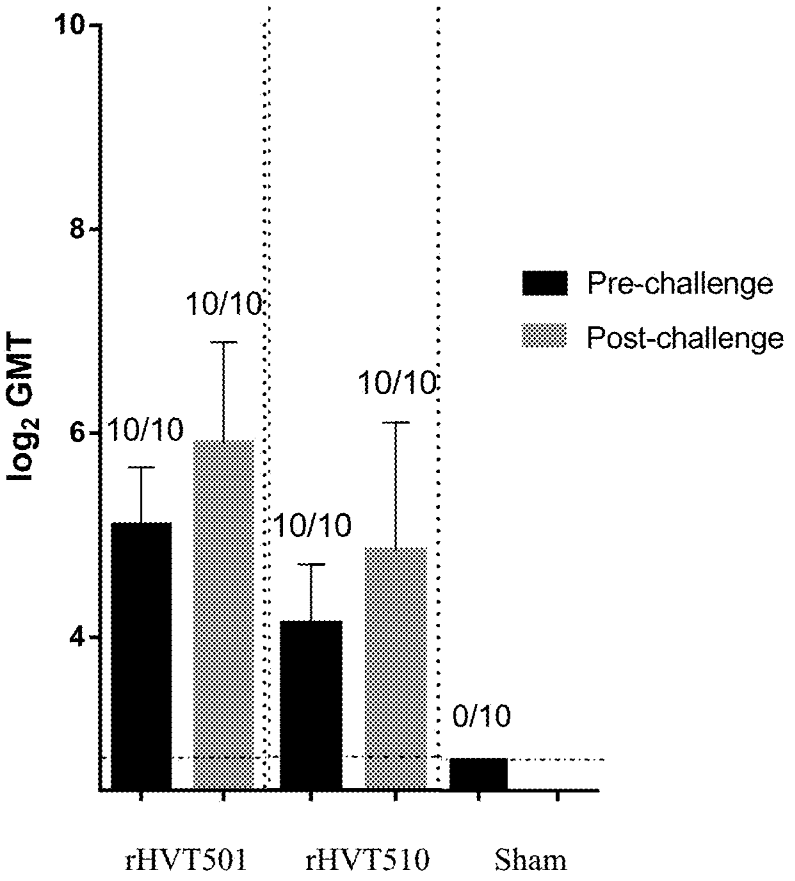
FIG. 23B depicts the serology results in A/Turkey/Minnesota/12582/2015 (H5N2) homologous challenge.
Figure 23C:
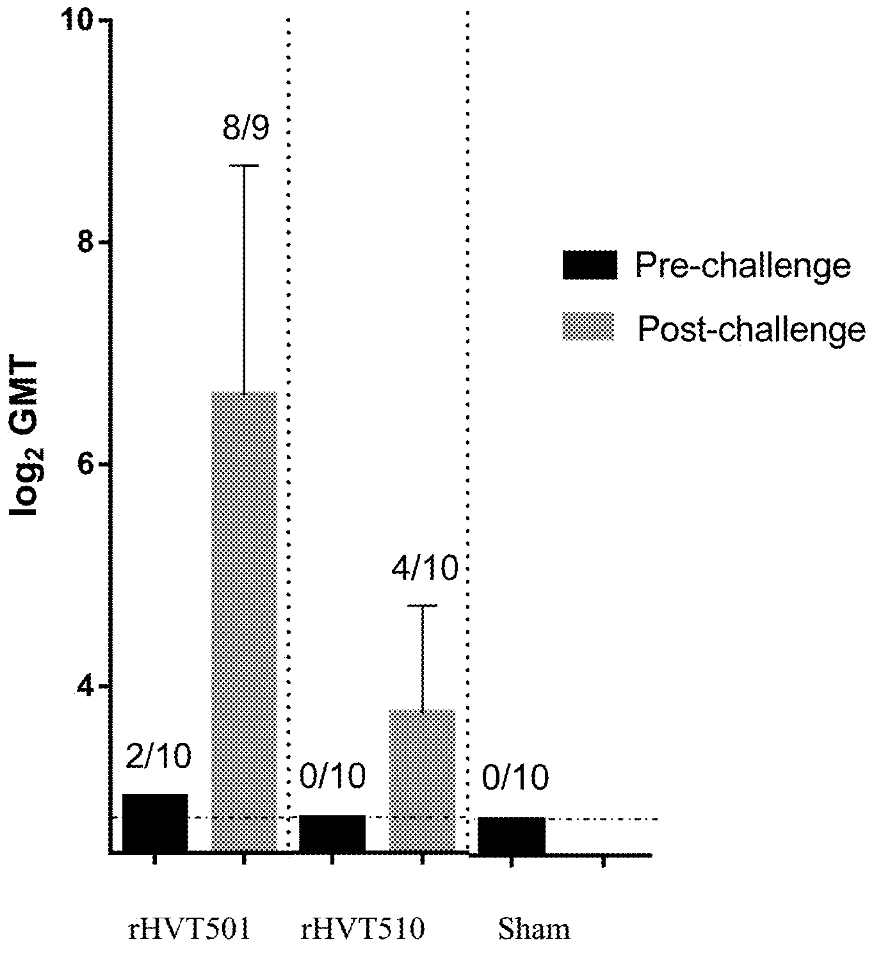
FIG. 23C depicts the serology results in A/Egypt/N04915/2014 (H5N1) heterologous challenge.

Serology results are shown in FIGS. 23B and 23C and Tables 10 and 11.

TABLE 10

| Hemagglutination inhibition (HI) assay results - A/Turkey/Minnesota/12582/2015 (H5N2) homologous challenge | | | | | |
|---|---|---|---|---|---|
| | | HI Serology-Number Positive* per Total (GMT-includes positive birds) | | log2 GMT | |
| Group | Bird # | Pre-challenge | Post-challenge | Pre-challenge | Post-challenge |
| rHVT501 | 1 | 16 | 128 | 4 | 7 |
| | 2 | 32 | 64 | 5 | 6 |
| | 3 | 32 | 128 | 5 | 7 |
| | 4 | 32 | 16 | 5 | 4 |
| | 5 | 32 | 32 | 5 | 5 |
| | 6 | 32 | 128 | 5 | 7 |
| | 7 | 64 | 64 | 6 | 6 |
| | 8 | 32 | 64 | 5 | 6 |
| | 9 | 64 | 64 | 6 | 6 |
| | 10 | 32 | 32 | 5 | 5 |
| | #birds | 10/10 | 10/10 | | |
| | GMT | 34.3 | 59.7 | | |
| | log2 GMT | 5.1 | 5.9 | | |
| rHVT510 | 1 | 32 | 128 | 5 | 7 |
| | 2 | 16 | 16 | 4 | 4 |
| | 3 | 16 | 32 | 4 | 5 |
| | 4 | 16 | 32 | 4 | 5 |
| | 5 | 16 | 8 | 4 | 3 |
| | 6 | 16 | 32 | 4 | 5 |
| | 7 | 8 | 8 | 3 | 3 |
| | 8 | 16 | 32 | 4 | 5 |
| | 9 | 16 | 32 | 4 | 5 |
| | 10 | 32 | 64 | 5 | 6 |
| | #birds | 10/10 | 10/10 | | |
| | GMT | 17.1 | 27.9 | | |
| | log2 GMT | 4.1 | 4.8 | | |
| sham | 1 | 4 | —** | 2 | — |
| | 2 | 4 | — | 2 | — |
| | 3 | 4 | — | 2 | — |
| | 4 | 4 | — | 2 | — |
| | 5 | 4 | — | 2 | — |
| | 6 | 4 | — | 2 | — |
| | 7 | 4 | — | 2 | — |

TABLE 10-continued

Hemagglutination inhibition (HI) assay results - A/Turkey/Minnesota/12582/2015 (H5N2) homologous challenge

| Group | Bird # | HI Serology-Number Positive* per Total (GMT-includes positive birds) Pre-challenge | HI Serology-Number Positive* per Total (GMT-includes positive birds) Post-challenge | log2 GMT Pre-challenge | log2 GMT Post-challenge |
|---|---|---|---|---|---|
| | 8 | 4 | — | 2 | — |
| | 9 | 4 | — | 2 | — |
| | 10 | 4 | — | 2 | — |
| | #birds | | | | |
| | GMT | | | | |
| | log2 GMT | | | | |

Positive*: above 4 log2 GMT are considered positive.
—**: bird not survived the challenge.

TABLE 11

Hemagglutination inhibition (HI) assay results - A/Egypt/N04915/2014 (H5N1) heterologous challenge

| Group | Bird # | HI Serology-Number Positive* per Total (GMT-includes positive birds) Pre-challenge | HI Serology-Number Positive* per Total (GMT-includes positive birds) Post-challenge | log2 GMT Pre-challenge | log2 GMT Post-challenge |
|---|---|---|---|---|---|
| rHVT501 | 1 | 8 | 512 | 3 | 9 |
| | 2 | 4 | 64 | 2 | 6 |
| | 3 | 4 | — | 2 | — |
| | 4 | 4 | 128 | 2 | 7 |
| | 5 | 8 | 8 | 3 | 3 |
| | 6 | 4 | 4 | 2 | 2 |
| | 7 | 4 | 512 | 2 | 9 |
| | 8 | 4 | 256 | 2 | 8 |
| | 9 | 4 | 32 | 2 | 5 |
| | 10 | 4 | 64 | 2 | 6 |
| | #birds | 2/10 | 8/9 | | |
| | GMT | 8 | 69.1 | | |
| | log2 GMT | 3 | 6.1 | | |
| rHVT510 | 1 | 4 | 4 | 2 | 2 |
| | 2 | 4 | 4 | 2 | 2 |
| | 3 | 4 | 4 | 2 | 2 |
| | 4 | 4 | 4 | 2 | 2 |
| | 5 | 4 | 8 | 2 | 2 |
| | 6 | 4 | 4 | 2 | 2 |
| | 7 | 4 | 8 | 2 | 3 |
| | 8 | 4 | 32 | 2 | 5 |
| | 9 | 4 | 16 | 2 | 4 |
| | 10 | 4 | 4 | 2 | 2 |
| | #birds | 0/10 | 4/10 | | |
| | GMT | 4 | 13.5 | | |
| | log2 GMT | 2 | 3.8 | | |
| sham | 1 | 4 | — | 2 | — |
| | 2 | 4 | — | 2 | — |
| | 3 | 4 | — | 2 | — |
| | 4 | 4 | — | 2 | — |
| | 5 | 4 | — | 2 | — |
| | 6 | 4 | — | 2 | — |
| | 7 | 4 | — | 2 | — |
| | 8 | 4 | — | 2 | — |

TABLE 11-continued

Hemagglutination inhibition (HI) assay results - A/Egypt/N04915/2014 (H5N1) heterologous challenge

| Group | Bird # | HI Serology-Number Positive* per Total (GMT-includes positive birds) Pre-challenge | HI Serology-Number Positive* per Total (GMT-includes positive birds) Post-challenge | log2 GMT Pre-challenge | log2 GMT Post-challenge |
|---|---|---|---|---|---|
| | 9 | 4 | — | 2 | — |
| | 10 | 4 | — | 2 | — |
| | #birds | 0/10 | | | |
| | GMT | 4 | | | |
| | log2 GMT | 2 | | | |

The HI results showed that for the pre-challenge response, a total of 12 birds have HI titers above the cut-off in rHVT501 group versus 10 in rHVT510 group, and for the post-challenge response the respective numbers are 18 and 14. The difference in the post-heterologous-challenge response indicated that fewer birds reacted in rHVT510 group because the vaccine has well controlled the replication of the challenge virus. Also the lower level of HI titer in the rHVT510 group when compared to the rHVT501 group indicates that the challenge virus was not able to replicate easily.

Figure 23D:
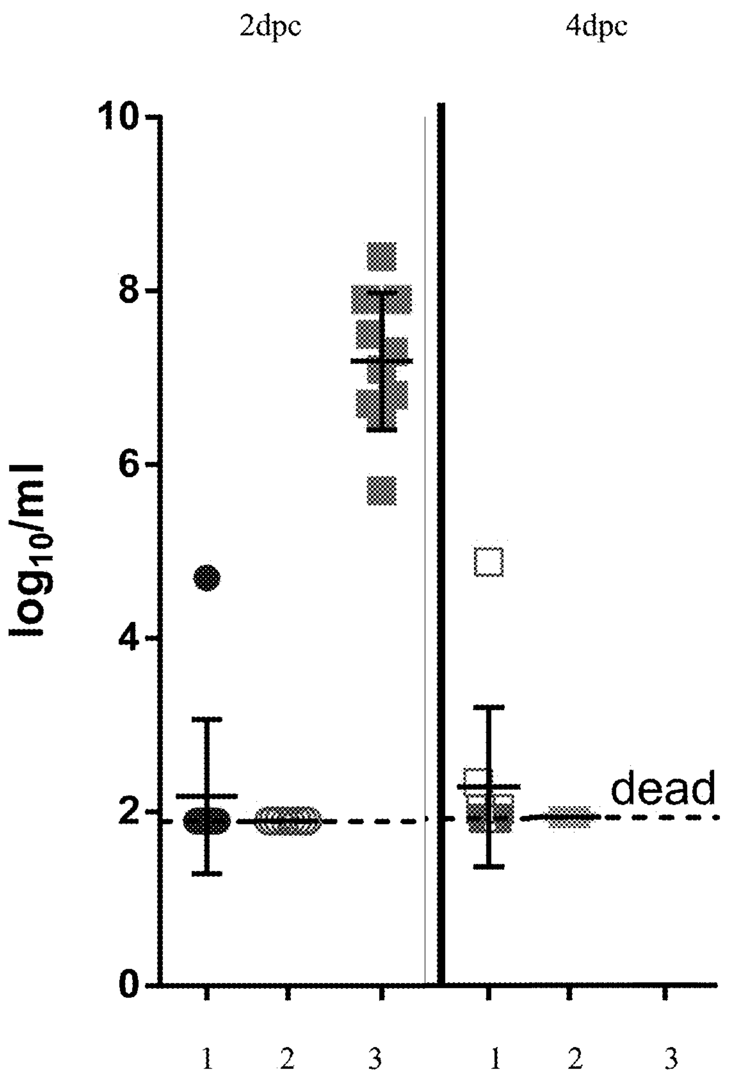
FIG. 23D depicts the viral shedding results in A/Turkey/Minnesota/12582/2015 (H5N2) homologous challenge.
Figure 23E:
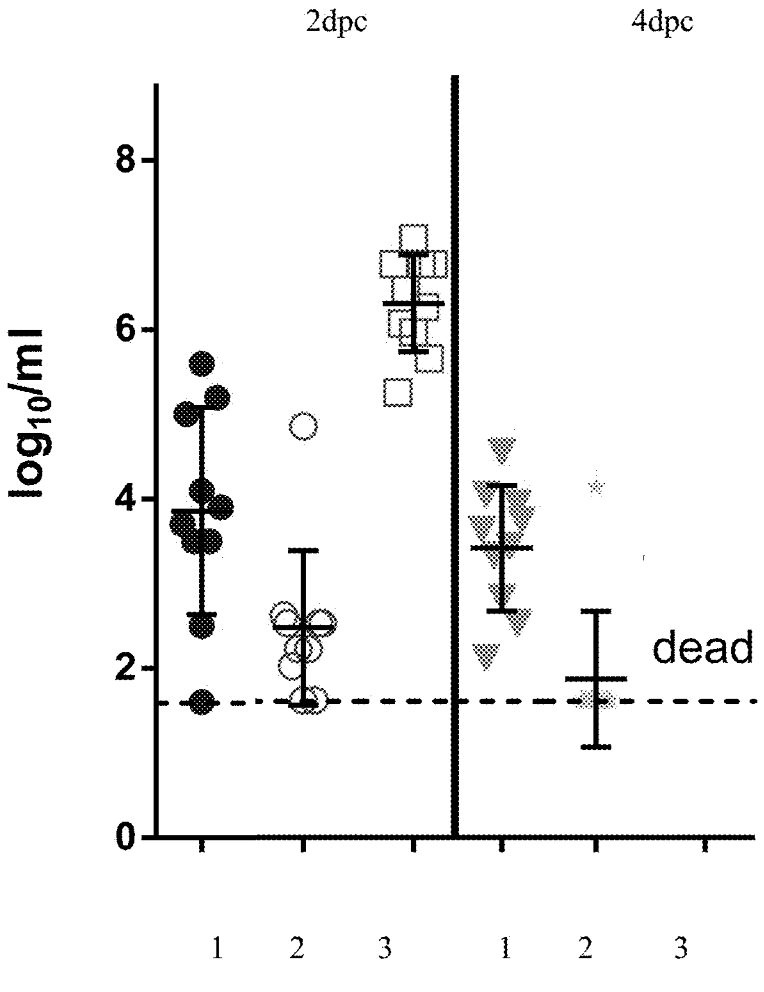
FIG. 23E depicts the viral shedding results in A/Egypt/N04915/2014 (H5N1) heterologous challenge.

Viral shedding results are shown in FIGS. 23D and 23E and Tables 12 and 13.

TABLE 12

Viral shedding results - A/Turkey/Minnesota/12582/2015 (H5N2) homologous challenge

| Group | Bird # | qRT-PCR (log10 EID50 titer/1 ml) 2dpc | qRT-PCR (log10 EID50 titer/1 ml) 4dpc |
|---|---|---|---|
| rHVT501 | 1 | 1.9* | 1.9 |
| | 2 | 1.9 | 1.9 |
| | 3 | 1.9 | 2.0 |
| | 4 | 1.9 | 2.3 |
| | 5 | 1.9 | 1.9 |
| | 6 | 1.9 | 2.0 |
| | 7 | 1.9 | 1.9 |
| | 8 | 4.7 | 4.8 |
| | 9 | 1.9 | 1.9 |
| | 10 | 1.9 | 1.9 |
| | #birds | 1/10 | 4/10 |
| | Mean | 2.2 | 2.2 |
| | STD | 0.9 | 0.9 |
| rHVT510 | 1 | 1.9 | 1.9 |
| | 2 | 1.9 | 1.9 |
| | 3 | 1.9 | 1.9 |
| | 4 | 1.9 | 1.9 |
| | 5 | 1.9 | 1.9 |
| | 6 | 1.9 | 1.9 |
| | 7 | 1.9 | 1.9 |
| | 8 | 1.9 | 1.9 |
| | 9 | 1.9 | 1.9 |
| | 10 | 1.9 | 1.9 |
| | #birds | 0/10 | 0/10 |
| | Mean | 1.9 | 1.9 |
| | STD | 0.0 | 0.0 |
| sham | 1 | 7.3 | — |
| | 2 | 7.9 | — |

TABLE 12-continued

Viral shedding results - A/Turkey/Minnesota/12582/2015 (H5N2) homologous challenge

| Group | Bird # | qRT-PCR (log10 EID50 titer/1 ml) 2dpc | 4dpc |
|---|---|---|---|
| | 3 | 7.1 | — |
| | 4 | 5.7 | — |
| | 5 | 7.9 | — |
| | 6 | 6.6 | — |
| | 7 | 6.8 | — |
| | 8 | 8.4 | — |
| | 9 | 7.5 | — |
| | 10 | 6.7 | — |
| | #birds | 10/10 | |
| | Mean | 7.2 | |
| | STD | 0.8 | |

*2.0 = Lowest Limit of Detection. Negatives is 1.9

TABLE 13

Viral shedding results - A/Egypt/N04915/2014 (H5N1) heterologous challenge

| Group | Bird # | qRT-PCR (log10 EID50 titer/lml) 2dpc | 4dpc |
|---|---|---|---|
| rHVT501 | 1 | 3.5* | 3.4 |
| | 2 | 3.7 | 3.3 |
| | 3 | 4.1 | 4.0 |
| | 4 | 5.2 | 4.5 |
| | 5 | 1.6 | 2.5 |
| | 6 | 2.5 | 2.1 |
| | 7 | 3.9 | 3.6 |
| | 8 | 5.6 | 3.7 |
| | 9 | 3.5 | 2.8 |
| | 10 | 5.0 | 3.9 |
| | #birds | 9/10 | 10/10 |
| | Mean | 3.9 | 3.4 |
| | STD | 1.2 | 0.7 |
| rHVT510 | 1 | 3.5 | 3.7 |
| | 2 | 2.4 | 1.6 |
| | 3 | 4.6 | 4.2 |
| | 4 | 2.8 | 1.7 |
| | 5 | 5.2 | 4.4 |
| | 6 | 4.4 | 4.5 |
| | 7 | 2.1 | 1.6 |
| | 8 | 4.8 | 4.1 |
| | 9 | 4.3 | 4.8 |
| | 10 | 2.0 | 2.1 |
| | #birds | 10/10 | 8/10 |
| | Mean | 3.6 | 3.3 |
| | STD | 1.2 | 1.4 |
| sham | 1 | 5.9 | — |
| | 2 | 7.0 | — |
| | 3 | 6.7 | — |
| | 4 | 6.7 | — |
| | 5 | 6.0 | — |
| | 6 | 5.2 | — |
| | 7 | 5.6 | — |
| | 8 | 6.4 | — |
| | 9 | 6.2 | — |
| | 10 | 6.7 | — |

TABLE 13-continued

Viral shedding results - A/Egypt/N04915/2014 (H5N1) heterologous challenge

| Group | Bird # | qRT-PCR (log10 EID50 titer/lml) 2dpc | 4dpc |
|---|---|---|---|
| | #birds | 10/10 | |
| | Mean | 6.2 | |
| | STD | 0.6 | |

*1.7 = Lowest Limit of Detection. Negatives is 1.6

Tables 12-13 and FIG. 23D-23E demonstrated that both rHVT501 and rHVT510 reduced viral shedding in vaccinated birds. The average viral shedding in rHVT501 and rHVT510 groups is much lower than the viral shedding in the sham group in both homologous and heterologous challenge studies. The viral shedding results showed that in the A/Turkey/Minnesota/12582/2015 (H5N2) homologous challenge study, none (0/10) of the birds in rHVT510 group shed any virus at both 2 dpc and 4 dpc, and one (1/10) and four (4/10) birds in rHVT501 group shed virus at 2 dpc and 4 dpc, respectively. All birds (10/10) in the sham group shed virus. The viral shedding results confirmed the HI results that rHVT510 has well controlled the replication of the challenge virus so that the challenge virus was not able to replicate easily.

Example 5

Immunogenicity and Challenge Studies in Broiler Chickens with Maternally Derived Antibody (MDA)

The goal of the study is to evaluate the prime-boost administration (two administrations) of two heterologous vaccines or administration at the same time (one administration) of two heterologous vaccines in MDA-positive broiler chickens to overcome MDA and increase immune response. The heterologous vaccines may be different types of vaccines, such as HVT AIV-HA vaccine or FPV AIV-HA vaccine.

Broiler chickens with AI H5 MDA are vaccinated with rHVT501 alone in ovo or one-day-old and boosted 3 weeks later with a recombinant NDV expressing influenza HA (rNDV-H5) to determine the presence of synergy between these two vaccine candidates. The birds are challenged 3 weeks post-boost (6 weeks of age) with Tk/MN/12582/15 H5N2 at $10^{6.0}$ $EID_{50}$ per chicken by the intranasal route.

Cloacal and Oropharyngeal swabs are taken at 2 and 4 DPC to evaluate impact on viral shed as described previously.

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A composition or vaccine comprising one or more recombinant herpesvirus of turkeys (HVT) viral vectors, wherein at least one HVT vector comprises one or more heterologous polynucleotides coding for and expressing at least one antigen of an avian influenza virus;

wherein at least one of the one or more heterologous polynucleotides encodes an HA antigen; and wherein the heterologous polynucleotide coding for and expressing the HA antigen comprising the amino acid sequence as set forth in SEQ ID NO: 2, 4, 20, 21, 22, 23, 24, 25, 26, 27, or 28 or wherein the heterologous polynucleotide encoding a polypeptide coding for the HA antigen comprising at least 75% sequence identity to the sequence as set forth in SEQ ID NO:1 or 3, or 99% sequence identity to the amino acid sequence as set forth in SEQ ID NO: 17.

2. The composition or vaccine of claim 1, wherein the polynucleotide encoding the HA antigen is operably linked to a promoter selected from the group consisting of an immediate early cytomegalovirus (CMV) promoter, guinea pig CMV promoter, an SV40 promoter, Human Herpesvirus Type III glycoprotein B (HHV3gB) promoter, Pseudorabies Virus promoters, glycoprotein X promoter, Herpes Simplex Virus-1 alpha 4 promoter, a Marek's Disease Virus glycoprotein A (or gC) promoter, a Marek's Disease Virus glycoprotein B promoter, a Marek's Disease Virus glycoprotein E promoter, a Marek's Disease Virus glycoprotein I promoter, an Infectious Laryngotracheitis Virus glycoprotein B, an Infectious Laryngotracheitis Virus glycoprotein E promoter, an Infectious Laryngotracheitis Virus glycoprotein D promoter, an Infectious Laryngotracheitis Virus glycoprotein I promoter, vaccinia H6, and a combination thereof.

3. The composition or vaccine of claim 1, wherein the polynucleotide encoding the HA antigen is inserted in the region selected from the group consisting of the IG1 locus (UL55), the IG2 locus, the IG3 locus, the UL43 locus, the US10 locus, and the SORF3/US2 locus on the HVT genome.

4. The composition or vaccine of claim 1, wherein the HA antigen comprises a mutated HA cleavage region having the sequence as set forth in SEQ ID NO:15.

5. The composition or vaccine of claim 1, wherein the composition or vaccine further comprises a second viral vector comprising a heterologous polynucleotide coding for and expressing at least one antigen of an avian influenza virus.

6. The composition or vaccine of claim 5, wherein the second viral vector is selected from a herpesvirus of turkeys (HVT) or a fowlpox virus (FPV).

7. The composition or vaccine of claim 5, wherein the second viral vector comprises a heterologous polynucleotide coding for and expressing an HA antigen having at least 95% sequence identity to the amino acid sequence as set forth in SEQ ID NO:2 or 80% sequence identity to the amino acid sequence as set forth in SEQ ID NO: 4, 20, 21, 22, 23, 24, 25, 26, 27, or 28.

8. The composition or vaccine of claim 5, wherein the second viral vector comprises a heterologous polynucleotide encoding a polypeptide coding for the HA antigen having at least 75% sequence identity to the sequence as set forth in SEQ ID NO:1, 3, 8, 9, 10, 12, 13, 17 or 19.

9. The composition or vaccine of claim 1, wherein the composition or vaccine further comprises a pharmaceutically or veterinarily acceptable carrier, excipient, vehicle or adjuvant.

10. A recombinant herpesvirus of turkeys (HVT) viral vector comprising one or more heterologous polynucleotides coding for and expressing at least one antigen of an avian influenza virus; wherein at least one of the one or more heterologous polynucleotides encodes an HA antigen; and wherein the heterologous polynucleotide coding for and expressing the HA antigen comprising the amino acid sequence as set forth in SEQ ID NO: 2, 4, 20, 21, 22, 23, 24, 25, 26, 27, or 28 or wherein the heterologous polynucleotide encoding a polypeptide coding for the HA antigen comprising at least 75% sequence identity to the sequence as set forth in SEQ ID NO:1 or 3, or 99% sequence identity to the amino acid sequence as set forth in SEQ ID NO: 17.

11. The recombinant viral vector of claim 10, wherein the polynucleotide encoding the HA antigen is operably linked to a promoter selected from the group consisting of an immediate early cytomegalovirus (CMV) promoter, mouse CMV IE promoter, guinea pig CMV promoter, an SV40 promoter, Human Herpesvirus Type III glycoprotein B (HHV3gB) promoter, Pseudorabies Virus promoters, glycoprotein X promoter, Herpes Simplex Virus-1 alpha 4 promoter, a Marek's Disease Virus glycoprotein A (or gC) promoter, a Marek's Disease Virus glycoprotein B promoter, a Marek's Disease Virus glycoprotein E promoter, a Marek's Disease Virus glycoprotein I promoter, an Infectious Laryngotracheitis Virus glycoprotein B, an Infectious Laryngotracheitis Virus glycoprotein E promoter, an Infectious Laryngotracheitis Virus glycoprotein D promoter, an Infectious Laryngotracheitis Virus glycoprotein I promoter, vaccinia H6, and a combination thereof.

12. The recombinant viral vector of claim 10, wherein the polynucleotide encoding the HA antigen is inserted in the region selected from the group consisting of the IG1 locus (UL55), the IG2 locus, the IG3 locus, the UL43 locus, the US10 locus, and the SORF3/US2 locus on the HVT genome.

13. The recombinant viral vector of claim 10, wherein the HA antigen comprises a mutated HA cleavage region having the sequence as set forth in SEQ ID NO:15.

14. A method of vaccinating an animal or for inducing an immunogenic or protective response in an animal against avian influenza pathogens, comprising at least one administration of the composition of claim 1 or vector of claim 10.

15. The method of claim 14, wherein the administration comprises a prime-boost administration regimen.

16. The method of claim 15, wherein the prime-boost administration comprises a prime-administration of a composition or vaccine or a polyvalent composition or vaccine comprising one or more viral vectors selected from the group consisting of HVT and FPV, wherein if there is only one viral vector, the viral vector is HVT, and a boost-administration of a composition or vaccine or a polyvalent composition or vaccine comprising one or more viral vectors selected from the group consisting of HVT and FPV which are the same or different from the viral vectors used in the prime-administration.

17. The method of claim 14, wherein the animal is avian.

18. A recombinant viral vector comprising one or more heterologous polynucleotides coding for and expressing at least one antigen of an avian influenza virus, wherein:

the recombinant viral vector is a fowlpox virus (FPV); and the recombinant viral vector comprises a heterologous polypeptide coding for and expressing an HA antigen wherein the heterologous polynucleotide coding for and expressing the HA antigen comprising the amino acid sequence as set forth in SEQ ID NO: 2, 4, 20, 21, 22, 23, 24, 25, 26, 27, or 28 or wherein the heterologous polynucleotide encoding a polypeptide coding for the HA antigen comprising at least 75% sequence identity to the sequence as set forth in SEQ ID NO:1 or 3, or 99% sequence identity to the amino acid sequence as set forth in SEQ ID NO: 17.

19. The recombinant viral vector of claim 18, wherein the polynucleotide encoding the HA antigen is operably linked to a promoter selected from the group consisting of an immediate early cytomegalovirus (CMV) promoter, mouse CMV IE promoter, guinea pig CMV promoter, an SV40 promoter, Human Herpesvirus Type III glycoprotein B (HHV3gB) promoter, Pseudorabies Virus promoters, glycoprotein X promoter, Herpes Simplex Virus-1 alpha 4 promoter, a Marek's Disease Virus glycoprotein A (or gC) promoter, a Marek's Disease Virus glycoprotein B promoter, a Marek's Disease Virus glycoprotein E promoter, a Marek's Disease Virus glycoprotein I promoter, an Infectious Laryngotracheitis Virus glycoprotein B, an Infectious Laryngotracheitis Virus glycoprotein E promoter, an Infectious Laryngotracheitis Virus glycoprotein D promoter, an Infectious Laryngotracheitis Virus glycoprotein I promoter, vaccinia H6, and a combination thereof.

20. The recombinant viral vector of claim 18, wherein the polynucleotide encoding the HA antigen is inserted in the region selected from the group consisting of the F7 locus and the F8 locus on the FPV genome.

21. The recombinant viral vector of claim 18, wherein the HA antigen comprises a mutated HA cleavage region having the sequence as set forth in SEQ ID NO:15.

22. A recombinant viral vector comprising a heterologous polynucleotide having at least 75% sequence identity to the sequence as set forth in SEQ ID NO: 8, 9, 10 or 19, or 90% sequence identity to the amino acid sequence as set forth in SEQ ID NO: 12 or 13.

* * * * *

SEQUENCE LISTING

<160> NUMBER OF SEQ ID NOS: 28

<210> SEQ ID NO 1
<211> LENGTH: 1692
<212> TYPE: DNA
<213> ORGANISM: artificial
<220> FEATURE:
<223> OTHER INFORMATION: DNA encoding H5N2 HA protein in plasmid
pHVTIG1SVLPC-HAsyn SbfI and pHVTIG1HHV3gBroSVLPC-HAsyn SbfI

<400> SEQUENCE: 1

```
atggaaaaga ttgtgctgct gtttgctgtg attagcctgg tgaagtcaga tcagatttgt     60
atcggttacc atgccaataa ttctactaaa caggtggata caattatgga aaagaacgtg    120
accgtgacac acgctcagga catcctggag agaactcata acgggaagct gtgcgatctg    180
aatggtgtga aacccctgat cctgaaggac tgctctgtgg caggctggct gctgggaaac    240
cccatgtgtg atgagttcat cagagtgcct gaatggtcct acattgtgga gagggctaac    300
cctgcaaatg atctgtgcta cccaggaacc ctgaacgact atgaggaact gaagcacctg    360
ctgagccgca tcaaccattt cgaaaagaca ctgatcatcc cccggagctc ctggcctaat    420
cacgagacta gcctgggagt gtccgcagct tgtccatacc agggagcatc ttcattcttt    480
cgcaacgtgg tgtggctgat caagaaaaat gatgcctacc ccaccatcaa aatctcatac    540
aacaacacaa accgggaaga tcttctgatc ctgtggggca tccaccattc caacaatgca    600
gccgagcaga ctaacctgta caaaaatcct gatacctatg tgtctgtggg gacttcaacc    660
ctgaaccagc gcctggtgcc aaagatcgcc actcggtcac aagtgaatgg gcagagtggt    720
cgcatggatt tcttttggac catcctgaag ccaaacgacg ctattcactt cgaaagcaac    780
ggcaatttta tcgcccccga gtacgcttat aagattgtga agaaaggaga cagtaccatc    840
atgaaaagcg agatggaata cggcactgc aacacaaagt gtcagactcc tatcggtgcc    900
attaacagta gcatgccatt ccacaatatc catcccctga caattgggga gtgccccaag    960
tatgtgaaat ctaacaagct ggtgctggct actggtctga gaaacagccc cctgagagag   1020
acccggggcc tgtttggagc aattgctggg tttattgagg gcggatggca gggtatggtg   1080
gatgggtggt acggttatca ccattccaac gaacaggggt ctggttacgc tgcagataaa   1140
gagtccacac agaaggctat tgacggagtg actaacaaag tgaacagcat cattgacaag   1200
atgaatactc agttcgaggc agtggggaga gaatttaaca atctggagag aaggatcgaa   1260
aacctgaata agaaaatgga agatggcttc ctggacgtgt ggacctacaa cgcagagctg   1320
ctggtgctga tggagaatga aaggacactg gattttcacg acagcaacgt gaaaaatctg   1380
tatgataaag tgagactgca gctgagggac aacgctaaag aactgggcaa tggatgtttc   1440
gagttttacc ataagtgcga taacgagtgt atggaaagtg tgagaaatgg cacatacgac   1500
tatccaaaat atagcgagga agcaatcctg aagagggagg aaattagcgg cgtgaaactg   1560
gagtccatcg gaacctacca gatcctgtca atttatagta cagtggcctc ctctctggca   1620
ctggccatca ttgtggctgg gctgtctctg tggatgtgta gtaacgggag tctgcagtgt   1680
aggatttgta tc                                                        1692
```

<210> SEQ ID NO 2
<211> LENGTH: 564
<212> TYPE: PRT
<213> ORGANISM: artificial
<220> FEATURE:
<223> OTHER INFORMATION: H5N2 HA protein in vHVT-501, vHVT-502 and
vHVT510

<400> SEQUENCE: 2

```
Met Glu Lys Ile Val Leu Leu Phe Ala Val Ile Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Ser Ser Trp Pro Asn His Glu Thr Ser
    130                 135                 140

Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
```

-continued

```
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 3
<211> LENGTH: 1692
<212> TYPE: DNA
<213> ORGANISM: artificial
<220> FEATURE:
<223> OTHER INFORMATION: DNA encoding mutant H5N2 HA in plasmid
      pHVTIG1SVMut-HAsyn SbfI (vHVT503)

<400> SEQUENCE: 3

atggaaaaga ttgtgctgct gtttgctgtg atttccctgg tgaagtccga ccagatttgt      60

attggctacc acgctaataa ctcaaccaaa caggtggata caattatgga aaagaacgtg     120

accgtgacac acgctcagga catcctggag agaactcata acgggaagct gtgcgatctg     180

aatggtgtga aacccctgat cctgaaggac tgctcagtgg caggctggct gctgggaaac     240

cccatgtgtg atgagttcat cagagtgcct gaatggtcct acattgtgga gagggctaac     300

cctgcaaatg atctgtgcta cccaggaacc ctgaacgact atgaggaact gaagcacctg     360

ctgagtcgca tcaaccattt cgaaaagaca ctgatcatcc cccggaacag ctggcctaat     420

cacgagactt cactgggcgt gagtgccgct tgtccatacc agggagcaag ctccttcttt     480

cgcaacgtgg tgtggctgat caagaaaaac aatgcctacc ccaccatcaa aatctcctac     540

aacaacacaa atcgggaaga tcttctgatc ctgtggggca tccaccattc taacaatgca     600

gccgagcaga ctaacctgta caaaaatcct gacacctatg tgagcgtggg gacttccacc     660

ctgaaccagc gcctggtgcc aaagatcgcc actcggtctc aggtgaacgg gcagaatggt     720

cgcatggatt tcttttggac catcctgaag ccaaatgacg ctattcactt cgaatccaac     780

ggcaatttta tcgcccccga gtacgcttat aagattgtga agaaaggaga ctctaccatc     840

atgaaatcag agatggaata cgggcactgc aacacaaagt gtcagactcc tatcggtgcc     900

attaactctt caatgccatt ccacaatatc catcccctga caattgggga gtgccccaag     960

tatgtgaaat caaacaagct ggtgctggct actggtctga ggaatagtcc tctgcgcgaa    1020

acccggggcc tgtttggagc aattgctggt tttattgagg gcggatggca gggtatggtg    1080

gatgggtggt acggttatca ccatagtaac gaacagggga gcggttacgc tgcagataaa    1140
```

-continued

```
gagtctacac agaaggctat tgacggagtg actaacaaag tgaacagcat cattgacaag   1200

atgaacactc agttcgaggc agtggggaga gaatttaaca atctggagag aaggatcgaa   1260

aacctgaata agaaaatgga agatggcttc ctggacgtgt ggacctacaa cgcagagctg   1320

ctggtgctga tggagaatga aaggacactg gattttcacg acagcaacgt gaaaaatctg   1380

tatgataaag tgagactgca gctgagggac aacgctaaag aactgggcaa tggatgtttc   1440

gagttttacc ataagtgcga taacgagtgt atggaaagcg tgagaaatgg cacatacgac   1500

tatccaaaat attccgagga agcaatcctg aagagggagg aaatttccgg cgtgaaactg   1560

gagtctatcg gaacctacca gatcctgtcc atttattcta cagtggccag tagcctggca   1620

ctggccatca ttgtggctgg tctgtctctg tggatgtgtt caaacggtag tctgcagtgt   1680

agaatctgta tc                                                       1692
```

```
<210> SEQ ID NO 4
<211> LENGTH: 564
<212> TYPE: PRT
<213> ORGANISM: artificial
<220> FEATURE:
<223> OTHER INFORMATION: mutant H5N2 HA in vHVT503

<400> SEQUENCE: 4

Met Glu Lys Ile Val Leu Leu Phe Ala Val Ile Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Asn Ser Trp Pro Asn His Glu Thr Ser
    130                 135                 140

Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asn Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Asn Gly
225                 230                 235                 240

Arg Met Asp Phe Phe Trp Thr Ile Leu Lys Pro Asn Asp Ala Ile His
                245                 250                 255
```

-continued

```
Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 5
<211> LENGTH: 368
<212> TYPE: DNA
<213> ORGANISM: artificial
<220> FEATURE:
<223> OTHER INFORMATION: SV40 promoter

<400> SEQUENCE: 5

```
caattcgagc tcggtacagc ttggctgtgg aatgtgtgtc agttagggtg tggaaagtcc      60

ccaggctccc cagcaggcag aagtatgcaa agcatgcatc tcaattagtc agcaaccagg     120

tgtggaaagt ccccaggctc cccagcaggc agaagtatgc aaagcatgca tctcaattag     180

tcagcaacca tagtcccgcc cctaactccg cccatcccgc ccctaactcc gcccagttcc     240

gcccattctc cgccccatgg ctgactaatt ttttttattt atgcagaggc cgaggccgcc     300
```

```
tcggcctctg agctattcca gaagtagtga ggaggctttt ttggaggcct aggcttttgc    360

aaaaagct                                                              368


<210> SEQ ID NO 6
<211> LENGTH: 478
<212> TYPE: DNA
<213> ORGANISM: artificial
<220> FEATURE:
<223> OTHER INFORMATION: HHV3gB promoter

<400> SEQUENCE: 6

ttatatcttc tgattgtgtg ggctctactt gtaaactctc aaaaaacgag cttggagaga     60

ccgacacaac cgccgtaaca aacaaagaaa atatgcataa aaagcataac cacaccccccg   120

taacggatgt tatgaaaacg ccgggtccgt tgaatccgga gccagccgct gcattagggt   180

gtatagaaga gaaaaaacgt ctgaatcgta gattacgacg gtattctggt cgatccctgt   240

ttctccactt tgaataatag ccacaagggg acatgtttct tcgtacgtta aataaatgcc   300

gtctaagggt ccgtgggaac tgcctatacc tttaggttga gacgtgcacc cgcgtggatc   360

cttacctaga cggtcaacgc gacataaccg cacctcccca caatggaaaa cagaggtgaa   420

tagtgtggtt gcaaacacaa gctccctaat atatttccag gcaagtctct gaattccc     478


<210> SEQ ID NO 7
<211> LENGTH: 154
<212> TYPE: DNA
<213> ORGANISM: artificial
<220> FEATURE:
<223> OTHER INFORMATION: Synthetic Poly A

<400> SEQUENCE: 7

aataaaatat ctttattttc attacatctg tgtgttggtt ttttgtgtga atcgatagta     60

ctaacatacg ctctccatca aaacaaaacg aaacaaaaca aactagcaaa ataggctgtc   120

cccagtgcaa gtgcaggtgc cagaacattt ctct                               154


<210> SEQ ID NO 8
<211> LENGTH: 4359
<212> TYPE: DNA
<213> ORGANISM: artificial
<220> FEATURE:
<223> OTHER INFORMATION: Nucleotide sequence of donor plasmid:
      pHVTIG1SVLPC-HAsyn SbfI
<220> FEATURE:
<221> NAME/KEY: Flanking Arms
<222> LOCATION: (1)..(832)
<220> FEATURE:
<221> NAME/KEY: SV40 Promoter
<222> LOCATION: (853)..(1220)
<220> FEATURE:
<221> NAME/KEY: HA H5N2
<222> LOCATION: (1236)..(2930)
<220> FEATURE:
<221> NAME/KEY: Synthetic Poly A
<222> LOCATION: (2945)..(3098)
<220> FEATURE:
<221> NAME/KEY: Flanking Arms
<222> LOCATION: (3119)..(4359)

<400> SEQUENCE: 8

ctcgaggata catccaaaga ggttgagtat tctctctaca cttcttgtta aatggaaagt     60

gcatttgctt gttcttacaa tcggcccgag tctcgttcac agcgcctcgt tcacacttaa   120

accacaaata gtctacaggc tatatgggag ccagactgaa actcacatat gactaatatt   180

cgggggtgtt agtcacgtgt agcccattgt gtgcatataa cgatgttgga cgcgtcctta   240
```

```
ttcgcggtgt acttgatact atggcagcga gcatgggata ttcatcctcg tcatcgttaa    300
catctctacg ggttcagaat gtttggcatg tcgtcgatcc tttgcccatc gttgcaaatt    360
acaagtccga tcgccatgac cgcgataagc ctgtaccatg tggcattagg gtgacatctc    420
gatcatacat tataagacca acgtgcgagt cttccaaaga cctgcacgcc ttcttcttcg    480
gattgtcaac gggttcttca gaatctatgc ccatatctgg cgttgagacc attgtgcgtt    540
taatgaacaa taaagcggca tgccatggaa aggagggctg cagatctcca ttttctcacg    600
ccactatcct ggacgctgta gacgataatt ataccatgaa tatagagggg gtatgtttcc    660
actgccactg tgatgataag ttttctccag attgttggat atctgcattt tctgctgccg    720
aacaaacttc atcgctatgc aaagagatgc gtgtgtacac gcgccgttga gtatacggga    780
aactaaatgt tcatagaggt ctttgggcta tatgttatta aataaaataa ttgtcgaccc    840
tgcaggtcga cccaattcga gctcggtaca gcttggctgt ggaatgtgtg tcagttaggg    900
tgtggaaagt ccccaggctc cccagcaggc agaagtatgc aaagcatgca tctcaattag    960
tcagcaacca ggtgtggaaa gtccccaggc tccccagcag gcagaagtat gcaaagcatg   1020
catctcaatt agtcagcaac catagtcccg cccctaactc cgcccatccc gcccctaact   1080
ccgcccagtt ccgcccattc tccgccccat ggctgactaa ttttttttat ttatgcagag   1140
gccgaggccg cctcggcctc tgagctattc cagaagtagt gaggaggctt ttttggaggc   1200
ctaggctttt gcaaaaagct cccgggggcgg ccgccatgga aaagattgtg ctgctgtttg   1260
ctgtgattag cctggtgaag tcagatcaga tttgtatcgg ttaccatgcc aataattcta   1320
ctaaacaggt ggatacaatt atggaaaaga acgtgaccgt gacacacgct caggacatcc   1380
tggagagaac tcataacggg aagctgtgcg atctgaatgg tgtgaaaccc ctgatcctga   1440
aggactgctc tgtggcaggc tggctgctgg gaaaccccat gtgtgatgag ttcatcagag   1500
tgcctgaatg gtcctacatt gtggagaggg ctaaccctgc aaatgatctg tgctacccag   1560
gaaccctgaa cgactatgag gaactgaagc acctgctgag ccgcatcaac catttcgaaa   1620
agacactgat catcccccgg agctcctggc ctaatcacga gactagcctg ggagtgtccg   1680
cagcttgtcc ataccaggga gcatcttcat tctttcgcaa cgtggtgtgg ctgatcaaga   1740
aaaatgatgc ctaccccacc atcaaaatct catacaacaa cacaaaccgg gaagatcttc   1800
tgatcctgtg gggcatccac cattccaaca atgcagccga gcagactaac ctgtacaaaa   1860
atcctgatac ctatgtgtct gtggggactt caaccctgaa ccagcgcctg gtgccaaaga   1920
tcgccactcg gtcacaagtg aatgggcaga gtggtcgcat ggatttcttt tggaccatcc   1980
tgaagccaaa cgacgctatt cacttcgaaa gcaacggcaa ttttatcgcc cccgagtacg   2040
cttataagat tgtgaagaaa ggagacagta ccatcatgaa aagcgagatg gaatacgggc   2100
actgcaacac aaagtgtcag actcctatcg gtgccattaa cagtagcatg ccattccaca   2160
atatccatcc cctgacaatt ggggagtgcc ccaagtatgt gaaatctaac aagctggtgc   2220
tggctactgg tctgagaaac agccccctga gagagacccg gggcctgttt ggagcaattg   2280
ctgggtttat tgagggcgga tggcagggta tggtggatgg gtggtacggt tatcaccatt   2340
ccaacgaaca ggggtctggt tacgctgcag ataaagagtc cacacagaag gctattgacg   2400
gagtgactaa caaagtgaac agcatcattg acaagatgaa tactcagttc gaggcagtgg   2460
ggagagaatt taacaatctg gagagaagga tcgaaaacct gaataagaaa atggaagatg   2520
gcttcctgga cgtgtggacc tacaacgcag agctgctggt gctgatggag aatgaaagga   2580
```

-continued

```
cactggattt tcacgacagc aacgtgaaaa atctgtatga taaagtgaga ctgcagctga   2640

gggacaacgc taaagaactg ggcaatggat gtttcgagtt ttaccataag tgcgataacg   2700

agtgtatgga aagtgtgaga aatggcacat acgactatcc aaaatatagc gaggaagcaa   2760

tcctgaagag ggaggaaatt agcggcgtga aactggagtc catcggaacc taccagatcc   2820

tgtcaattta tagtacagtg gcctcctctc tggcactggc catcattgtg gctgggctgt   2880

ctctgtggat gtgtagtaac gggagtctgc agtgtaggat ttgtatctga gcggccgcga   2940

tatcaataaa atatctttat tttcattaca tctgtgtgtt ggttttttgt gtgaatcgat   3000

agtactaaca tacgctctcc atcaaaacaa aacgaaacaa aacaaactag caaaataggc   3060

tgtccccagt gcaagtgcag gtgccagaac atttctcttc tagacctgca gggaattcgt   3120

ttaatgttag tttattcaat gcattggttg caaatattca ttacttctcc aatcccaggt   3180

cattctttag cgagatgatg ttatgacatt gctgtgaaaa ttactacagg atatattttt   3240

aagatgcagg agtaacaatg tgcatagtag gcgtagttat cgcagacgtg caacgcttcg   3300

catttgagtt accgaagtgc ccaacagtgc tgcggttatg gtttatgcgc acagaatcca   3360

tgcatgtcct aattgaacca tccgattttt cttttaatcg cgatcgttgt ttgggcaact   3420

gcgttatttc agatctaaaa aatttaccct ttatgaccat cacatctctc tggctcatac   3480

cccgcttgga taagatatca tgtagattcc gccctaagaa atgcaaacta acattattgt   3540

cggttccata tacacttcca tcttgtcctt cgaaaataac aaactcgcgc aatagaccgt   3600

ccgtacatgc atggccgatg tgtgtcaaca tcattggtct gctagatccc gatgggacga   3660

atcgtacagt cgtcgctcca gcattggcaa aaatccccag ataccctcca tgcggcaaat   3720

ctaaattgcg accccgaaga gactgcacca aagtcttatc gacgcacgct gatttttttg   3780

aacagcggga gcccattatc ttcagtggag cgtagacggg cgaggctaat tatgtgacat   3840

agcaacactg catgtatgtt tttataaatc aataagagta cataatttat tacgtatcat   3900

ttccgtttgt aatatactgt atacatcatc cacactatta gtcagcacta gcgcgcgggc   3960

gcacgttaca atagcagcgt gcccgttatc tatattgtcc gatatttaca cataacattt   4020

catcgacatg attaaatacc taagtactgc acacagatgt ttaatgtata tcgtcatata   4080

aattatatcg ctaggacaga cccaaacgac ctttatccca aacagtcaga tcctcttctc   4140

aagtgtcgat ttctgttatg gaatatgcat accctggccc agaaattgca cgcacgagcg   4200

tagtgaatgc gtcattggtt ttacatttaa aggctaaatg cacaaattct ttagacgaca   4260

gcacatcgtt aaatagcatc tctagcgttc ttatgaatgc taagcattgg agtcctcctg   4320

gtcggccaca ataacagctg agtatcatac cctgagctc                          4359
```

```
<210> SEQ ID NO 9
<211> LENGTH: 4852
<212> TYPE: DNA
<213> ORGANISM: artificial
<220> FEATURE:
<223> OTHER INFORMATION: Nucleotide sequence of donor plasmid:
      pHVTIG1HHV3gBroSVLPC-HAsyn SbfI
<220> FEATURE:
<221> NAME/KEY: Flanking Arms
<222> LOCATION: (1)..(1241)
<220> FEATURE:
<221> NAME/KEY: HHV3gB promoter
<222> LOCATION: (1271)..(1748)
<220> FEATURE:
<221> NAME/KEY: SV40 Promoter
<222> LOCATION: (1755)..(2122)
<220> FEATURE:
<221> NAME/KEY: HA H5N2
```

<222> LOCATION: (2138)..(3832)
<220> FEATURE:
<221> NAME/KEY: Synthetic Poly A
<222> LOCATION: (3847)..(4000)
<220> FEATURE:
<221> NAME/KEY: Flanking Arms
<222> LOCATION: (4021)..(4852)

<400> SEQUENCE: 9

```
gagctcaggg tatgatactc agctgttatt gtggccgacc aggaggactc caatgcttag     60
cattcataag aacgctagag atgctattta acgatgtgct gtcgtctaaa gaatttgtgc    120
atttagcctt taaatgtaaa accaatgacg cattcactac gctcgtgcgt gcaatttctg    180
ggccagggta tgcatattcc ataacagaaa tcgacacttg agaagaggat ctgactgttt    240
gggataaagg tcgtttgggt ctgtcctagc gatataattt atatgacgat atacattaaa    300
catctgtgtg cagtacttag gtatttaatc atgtcgatga aatgttatgt gtaaatatcg    360
gacaatatag ataacgggca cgctgctatt gtaacgtgcg cccgcgcgct agtgctgact    420
aatagtgtgg atgatgtata cagtatatta caaacggaaa tgatacgtaa taaattatgt    480
actcttattg atttataaaa acatacatgc agtgttgcta tgtcacataa ttagcctcgc    540
ccgtctacgc tccactgaag ataatgggct cccgctgttc aaaaaaatca gcgtgcgtcg    600
ataagacttt ggtgcagtct cttcggggtc gcaatttaga tttgccgcat ggagggtatc    660
tggggatttt tgccaatgct ggagcgacga ctgtacgatt cgtcccatcg ggatctagca    720
gaccaatgat gttgacacac atcggccatg catgtacgga cggtctattg cgcgagtttg    780
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaaaga aaaatcggat ggttcaatta ggacatgcat ggattctgtg cgcataaacc   1020
ataaccgcag cactgttggg cacttcggta actcaaatgc gaagcgttgc acgtctgcga   1080
taactacgcc tactatgcac attgttactc ctgcatctta aaaatatatc ctgtagtaat   1140
tttcacagca atgtcataac atcatctcgc taaagaatga cctgggattg gagaagtaat   1200
gaatatttgc aaccaatgca ttgaataaac taacattaaa cgaattccct gcaggtcgag   1260
gccgcccggg ttatatcttc tgattgtgtg ggctctactt gtaaactctc aaaaaacgag   1320
cttggagaga ccgacacaac cgccgtaaca aacaaagaaa atatgcataa aaagcataac   1380
cacacccccg taacggatgt tatgaaaacg ccgggtccgt tgaatccgga gccagccgct   1440
gcattagggt gtatagaaga gaaaaaacgt ctgaatcgta gattacgacg gtattctggt   1500
cgatccctgt ttctccactt tgaataatag ccacaagggg acatgtttct tcgtacgtta   1560
aataaatgcc gtctaagggt ccgtgggaac tgcctatacc tttaggttga gacgtgcacc   1620
cgcgtggatc cttacctaga cggtcaacgc gacataaccg cacctcccca caatggaaaa   1680
cagaggtgaa tagtgtggtt gcaaacacaa gctccctaat atatttccag gcaagtctct   1740
gaattccctc gacccaattc gagctcggta cagcttggct gtggaatgtg tgtcagttag   1800
ggtgtggaaa gtccccaggc tccccagcag gcagaagtat gcaaagcatg catctcaatt   1860
agtcagcaac caggtgtgga aagtccccag gctccccagc aggcagaagt atgcaaagca   1920
tgcatctcaa ttagtcagca accatagtcc cgcccctaac tccgcccatc ccgcccctaa   1980
ctccgcccag ttccgcccat tctccgcccc atggctgact aatttttttt atttatgcag   2040
aggccgaggc cgcctcggcc tctgagctat tccagaagta gtgaggaggc ttttttggag   2100
```

-continued

```
gcctaggctt ttgcaaaaag ctcccggggc ggccgccatg gaaaagattg tgctgctgtt   2160
tgctgtgatt agcctggtga agtcagatca gatttgtatc ggttaccatg ccaataattc   2220
tactaaacag gtggatacaa ttatggaaaa gaacgtgacc gtgacacacg ctcaggacat   2280
cctggagaga actcataacg ggaagctgtg cgatctgaat ggtgtgaaac ccctgatcct   2340
gaaggactgc tctgtggcag gctggctgct gggaaacccc atgtgtgatg agttcatcag   2400
agtgcctgaa tggtcctaca ttgtggagag ggctaaccct gcaaatgatc tgtgctaccc   2460
aggaaccctg aacgactatg aggaactgaa gcacctgctg agccgcatca accatttcga   2520
aaagacactg atcatccccc ggagctcctg gcctaatcac gagactagcc tgggagtgtc   2580
cgcagcttgt ccataccagg gagcatcttc attctttcgc aacgtggtgt ggctgatcaa   2640
gaaaaatgat gcctacccca ccatcaaaat ctcatacaac aacacaaacc gggaagatct   2700
tctgatcctg tggggcatcc accattccaa caatgcagcc gagcagacta acctgtacaa   2760
aaatcctgat acctatgtgt ctgtggggac ttcaaccctg aaccagcgcc tggtgccaaa   2820
gatcgccact cggtcacaag tgaatgggca gagtggtcgc atggatttct tttggaccat   2880
cctgaagcca aacgacgcta ttcacttcga aagcaacggc aattttatcg cccccgagta   2940
cgcttataag attgtgaaga aaggagacag taccatcatg aaaagcgaga tggaatacgg   3000
gcactgcaac acaaagtgtc agactcctat cggtgccatt aacagtagca tgccattcca   3060
caatatccat cccctgacaa ttggggagtg ccccaagtat gtgaaatcta acaagctggt   3120
gctggctact ggtctgagaa acagcccccct gagagagacc cggggcctgt ttggagcaat   3180
tgctgggttt attgagggcg gatggcaggg tatggtggat gggtggtacg gttatcacca   3240
ttccaacgaa caggggtctg gttacgctgc agataaagag tccacacaga aggctattga   3300
cggagtgact aacaaagtga acagcatcat tgacaagatg aatactcagt tcgaggcagt   3360
ggggagagaa tttaacaatc tggagagaag gatcgaaaac ctgaataaga aaatggaaga   3420
tggcttcctg gacgtgtgga cctacaacgc agagctgctg gtgctgatgg agaatgaaag   3480
gacactggat tttcacgaca gcaacgtgaa aaatctgtat gataaagtga gactgcagct   3540
gagggacaac gctaaagaac tgggcaatgg atgtttcgag ttttaccata agtgcgataa   3600
cgagtgtatg gaaagtgtga gaaatggcac atacgactat ccaaaatata gcgaggaagc   3660
aatcctgaag agggaggaaa ttagcggcgt gaaactggag tccatcggaa cctaccagat   3720
cctgtcaatt tatagtacag tggcctcctc tctggcactg gccatcattg tggctgggct   3780
gtctctgtgg atgtgtagta acgggagtct gcagtgtagg atttgtatct gagcggccgc   3840
gatatcaata aaatatcttt attttcatta catctgtgtg ttggtttttt gtgtgaatcg   3900
atagtactaa catacgctct ccatcaaaac aaaacgaaac aaaacaaact agcaaaatag   3960
gctgtcccca gtgcaagtgc aggtgccaga acatttctct tctagacctg cagggtcgac   4020
aattatttta tttaataaca tatagcccaa agacctctat gaacatttag tttcccgtat   4080
actcaacggc gcgtgtacac acgcatctct ttgcatagcg atgaagtttg ttcggcagca   4140
gaaaatgcag atatccaaca atctggagaa aacttatcat cacagtggca gtggaaacat   4200
accccctcta tattcatggt ataattatcg tctacagcgt ccaggatagt ggcgtgagaa   4260
aatggagatc tgcagccctc ctttccatgg catgccgctt tattgttcat taaacgcaca   4320
atggtctcaa cgccagatat gggcatagat tctgaagaac ccgctgacaa tccgaagaag   4380
aaggcgtgca ggtctttgga agactcgcac gttggtctta taatgtatga tcgagatgtc   4440
```

accctaatgc cacatggtac aggcttatcg cggtcatggc gatcggactt gtaatttgca 4500
acgatgggca aaggatcgac gacatgccaa acattctgaa cccgtagaga tgttaacgat 4560
gacgaggatg aatatcccat gctcgctgcc atagtatcaa gtacaccgcg aataaggacg 4620
cgtccaacat cgttatatgc acacaatggg ctacacgtga ctaacacccc cgaatattag 4680
tcatatgtga gtttcagtct ggctcccata tagcctgtag actatttgtg gtttaagtgt 4740
gaacgaggcg ctgtgaacga gactcgggcc gattgtaaga acaagcaaat gcactttcca 4800
tttaacaaga agtgtagaga gaatactcaa cctctttgga tgtatcctcg ag 4852

<210> SEQ ID NO 10
<211> LENGTH: 4359
<212> TYPE: DNA
<213> ORGANISM: artificial
<220> FEATURE:
<223> OTHER INFORMATION: Nucleotide sequence of donor plasmid: pHVTIG1SVMut-HAsyn SbfI
<220> FEATURE:
<221> NAME/KEY: Flanking Arms
<222> LOCATION: (1)..(832)
<220> FEATURE:
<221> NAME/KEY: SV40 Promoter
<222> LOCATION: (853)..(1220)
<220> FEATURE:
<221> NAME/KEY: Mut-HA H5N2
<222> LOCATION: (1236)..(2930)
<220> FEATURE:
<221> NAME/KEY: Synthetic Poly A
<222> LOCATION: (2945)..(3098)
<220> FEATURE:
<221> NAME/KEY: Flanking Arms
<222> LOCATION: (3119)..(4359)

<400> SEQUENCE: 10
ctcgaggata catccaaaga ggttgagtat tctctctaca cttcttgtta aatggaaagt 60
gcatttgctt gttcttacaa tcggcccgag tctcgttcac agcgcctcgt tcacacttaa 120
accacaaata gtctacaggc tatatgggag ccagactgaa actcacatat gactaatatt 180
cgggggtgtt agtcacgtgt agcccattgt gtgcatataa cgatgttgga cgcgtcctta 240
ttcgcggtgt acttgatact atggcagcga gcatgggata ttcatcctcg tcatcgttaa 300
catctctacg ggttcagaat gtttggcatg tcgtcgatcc tttgcccatc gttgcaaatt 360
acaagtccga tcgccatgac cgcgataagc ctgtaccatg tggcattagg gtgacatctc 420
gatcatacat tataagacca acgtgcgagt cttccaaaga cctgcacgcc ttcttcttcg 480
gattgtcaac gggttcttca gaatctatgc ccatatctgg cgttgagacc attgtgcgtt 540
taatgaacaa taaagcggca tgccatggaa aggagggctg cagatctcca ttttctcacg 600
ccactatcct ggacgctgta gacgataatt ataccatgaa tatagagggg gtatgtttcc 660
actgccactg tgatgataag ttttctccag attgttggat atctgcattt tctgctgccg 720
aacaaacttc atcgctatgc aaagagatgc gtgtgtacac gcgccgttga gtatacggga 780
aactaaatgt tcatagaggt ctttgggcta tatgttatta aataaaataa ttgtcgaccc 840
tgcaggtcga cccaattcga gctcggtaca gcttggctgt ggaatgtgtg tcagttaggg 900
tgtggaaagt ccccaggctc cccagcaggc agaagtatgc aaagcatgca tctcaattag 960
tcagcaacca ggtgtggaaa gtccccaggc tccccagcag gcagaagtat gcaaagcatg 1020
catctcaatt agtcagcaac catagtcccg cccctaactc cgcccatccc gcccctaact 1080
ccgcccagtt ccgcccattc tccgccccat ggctgactaa ttttttttat ttatgcagag 1140
gccgaggccg cctcggcctc tgagctattc cagaagtagt gaggaggctt ttttggaggc 1200

```
ctaggctttt gcaaaaagct cccggggcgg ccgccatgga aaagattgtg ctgctgtttg   1260
ctgtgatttc cctggtgaag tccgaccaga tttgtattgg ctaccacgct aataactcaa   1320
ccaaacaggt ggatacaatt atggaaaaga acgtgaccgt gacacacgct caggacatcc   1380
tggagagaac tcataacggg aagctgtgcg atctgaatgg tgtgaaaccc ctgatcctga   1440
aggactgctc agtggcaggc tggctgctgg gaaaccccat gtgtgatgag ttcatcagag   1500
tgcctgaatg gtcctacatt gtggagaggg ctaaccctgc aaatgatctg tgctacccag   1560
gaaccctgaa cgactatgag gaactgaagc acctgctgag tcgcatcaac catttcgaaa   1620
agacactgat catcccccgg aacagctggc ctaatcacga gacttcactg ggcgtgagtg   1680
ccgcttgtcc ataccaggga gcaagctcct tctttcgcaa cgtggtgtgg ctgatcaaga   1740
aaaacaatgc ctaccccacc atcaaaatct cctacaacaa cacaaatcgg gaagatcttc   1800
tgatcctgtg gggcatccac cattctaaca atgcagccga gcagactaac ctgtacaaaa   1860
atcctgacac ctatgtgagc gtggggactt ccaccctgaa ccagcgcctg gtgccaaaga   1920
tcgccactcg gtctcaggtg aacgggcaga atggtcgcat ggatttcttt tggaccatcc   1980
tgaagccaaa tgacgctatt cacttcgaat ccaacggcaa ttttatcgcc cccgagtacg   2040
cttataagat tgtgaagaaa ggagactcta ccatcatgaa atcagagatg gaatacgggc   2100
actgcaacac aaagtgtcag actcctatcg gtgccattaa ctcttcaatg ccattccaca   2160
atatccatcc cctgacaatt ggggagtgcc ccaagtatgt gaaatcaaac aagctggtgc   2220
tggctactgg tctgaggaat agtcctctgc gcgaaacccg gggcctgttt ggagcaattg   2280
ctggttttat tgagggcgga tggcagggta tggtggatgg gtggtacggt tatcaccata   2340
gtaacgaaca ggggagcggt tacgctgcag ataaagagtc tacacagaag gctattgacg   2400
gagtgactaa caaagtgaac agcatcattg acaagatgaa cactcagttc gaggcagtgg   2460
ggagagaatt taacaatctg gagagaagga tcgaaaacct gaataagaaa atggaagatg   2520
gcttcctgga cgtgtggacc tacaacgcag agctgctggt gctgatggag aatgaaagga   2580
cactggattt tcacgacagc aacgtgaaaa atctgtatga taaagtgaga ctgcagctga   2640
gggacaacgc taaagaactg ggcaatggat gtttcgagtt ttaccataag tgcgataacg   2700
agtgtatgga aagcgtgaga aatggcacat acgactatcc aaaatattcc gaggaagcaa   2760
tcctgaagag ggaggaaatt tccggcgtga aactggagtc tatcggaacc taccagatcc   2820
tgtccattta ttctacagtg gccagtagcc tggcactggc catcattgtg gctggtctgt   2880
ctctgtggat gtgttcaaac ggtagtctgc agtgtagaat ctgtatctga gcggccgcga   2940
tatcaataaa atatctttat tttcattaca tctgtgtgtt ggttttttgt gtgaatcgat   3000
agtactaaca tacgctctcc atcaaaacaa aacgaaacaa aacaaactag caaaataggc   3060
tgtccccagt gcaagtgcag gtgccagaac atttctcttc tagacctgca gggaattcgt   3120
ttaatgttag tttattcaat gcattggttg caaatattca ttacttctcc aatcccaggt   3180
cattctttag cgagatgatg ttatgacatt gctgtgaaaa ttactacagg atatattttt   3240
aagatgcagg agtaacaatg tgcatagtag gcgtagttat cgcagacgtg caacgcttcg   3300
catttgagtt accgaagtgc ccaacagtgc tgcggttatg gtttatgcgc acagaatcca   3360
tgcatgtcct aattgaacca tccgattttt cttttaatcg cgatcgttgt ttgggcaact   3420
gcgttatttc agatctaaaa aatttaccct ttatgaccat cacatctctc tggctcatac   3480
cccgcttgga taagatatca tgtagattcc gccctaagaa atgcaaacta acattattgt   3540
```

-continued

```
cggttccata tacacttcca tcttgtcctt cgaaaataac aaactcgcgc aatagaccgt   3600

ccgtacatgc atggccgatg tgtgtcaaca tcattggtct gctagatccc gatgggacga   3660

atcgtacagt cgtcgctcca gcattggcaa aaatccccag ataccctcca tgcggcaaat   3720

ctaaattgcg accccgaaga gactgcacca aagtcttatc gacgcacgct gatttttttg   3780

aacagcggga gcccattatc ttcagtggag cgtagacggg cgaggctaat tatgtgacat   3840

agcaacactg catgtatgtt tttataaatc aataagagta cataatttat tacgtatcat   3900

ttccgtttgt aatatactgt atacatcatc cacactatta gtcagcacta gcgcgcgggc   3960

gcacgttaca atagcagcgt gcccgttatc tatattgtcc gatatttaca cataacattt   4020

catcgacatg attaaatacc taagtactgc acacagatgt ttaatgtata tcgtcatata   4080

aattatatcg ctaggacaga cccaaacgac ctttatccca aacagtcaga tcctcttctc   4140

aagtgtcgat ttctgttatg gaatatgcat accctggccc agaaattgca cgcacgagcg   4200

tagtgaatgc gtcattggtt ttacatttaa aggctaaatg cacaaattct ttagacgaca   4260

gcacatcgtt aaatagcatc tctagcgttc ttatgaatgc taagcattgg agtcctcctg   4320

gtcggccaca ataacagctg agtatcatac cctgagctc                            4359
```

<210> SEQ ID NO 11
<211> LENGTH: 124
<212> TYPE: DNA
<213> ORGANISM: artificial
<220> FEATURE:
<223> OTHER INFORMATION: vaccinia H6 promoter

<400> SEQUENCE: 11

```
ttctttattc tatacttaaa aagtgaaaat aaatacaaag gttcttgagg gttgtgttaa     60

attgaaagcg agaaataatc ataaattatt tcattatcgc gatatccgtt aagtttgtat    120

cgta                                                                 124
```

<210> SEQ ID NO 12
<211> LENGTH: 4754
<212> TYPE: DNA
<213> ORGANISM: artificial
<220> FEATURE:
<223> OTHER INFORMATION: Nucleotide sequence of donor plasmid pF8
      H6pLPC-HA H5N2
<220> FEATURE:
<221> NAME/KEY: Flanking Arms
<222> LOCATION: (1)..(1429)
<220> FEATURE:
<221> NAME/KEY: H6 Promoter
<222> LOCATION: (1516)..(1639)
<220> FEATURE:
<221> NAME/KEY: HA H5N2
<222> LOCATION: (1649)..(3343)
<220> FEATURE:
<221> NAME/KEY: Flanking Arms
<222> LOCATION: (3379)..(4754)

<400> SEQUENCE: 12

```
gacccttac aagaataaaa gaagaaacaa ctgtgaaata gtttataaat gtaattcgta     60

tgcagaaaac gataatatat tttggtatga gaaatctaaa ggagacatag tttgtataga    120

catgcgctct tccgatgaga tattcgatgc ttttctaatg tatcatatag ctacaagata    180

tgcctatcat gatgatgata tatatctaca aatagtgtta tattattcta ataatcaaaa    240

tgttatatct tatattacga aaaataaata cgttaagtat ataagaaata aaactagaga    300

cgatattcat aaagtaaaaa tattagctct agaagacttt acaacggaag aaatatattg    360
```

-continued

```
ttggattagt aatatataac agcgtagctg cacggttttg atcattttcc aacaatataa    420
accaatgaag gaggacgact catcaaacat aaataacatt cacggaaaat attcagtatc    480
agatttatca caagatgatt atgttattga atgtatagac ggatcttttg attcgatcaa    540
gtatagagat ataaaggtta taataatgaa gaataacggt tacgttaatt gtagtaaatt    600
atgtaaaatg cggaataaat acttttctag atggttgcgt ctttctactt ctaaagcatt    660
attagacatt tacaataata agtcagtaga taatgctatt gttaaagtct atggtaaagg    720
taagaaactt attataacag gattttatct caaacaaaat atgatacgtt atgttattga    780
gtggataggg gatgatttta caaacgatat atacaaaatg attaatttct ataatgcgtt    840
attcggtaac gatgaattaa aaatagtatc ctgtgaaaac actctatgcc cgtttataga    900
acttggtaga tgctattatg gtaaaaaatg taagtatata cacggagatc aatgtgatat    960
ctgtggtcta tatatactac accctaccga tattaaccaa cgagtttctc acaagaaaac   1020
ttgtttagta gatagagatt ctttgattgt gtttaaaaga agtaccagta aaaagtgtgg   1080
catatgcata gaagaaataa acaaaaaaca tatttccgaa cagtattttg gaattctccc   1140
aagttgtaaa catatttttt gcctatcatg tataagacgt tgggcagata ctaccagaaa   1200
tacagatact gaaaatacgt gtcctgaatg tagaatagtt tttcctttca taatacccag   1260
taggtattgg atagataata aatatgataa aaaaatatta tataatagat ataagaaaat   1320
gatttttaca aaaataccta taagaacaat aaaaatataa ttacatttac ggaaaatagc   1380
tggttttagt ttaccaactt agagtaatta tcatattgaa tctatattgc taattagcta   1440
ataaaaaccc gggttaatta attagtcatc aggcagggcg agaacgagac tatctgctcg   1500
ttaattaatt agagcttctt tattctatac ttaaaaagtg aaaataaata caaaggttct   1560
tgagggttgt gttaaattga aagcgagaaa taatcataaa ttatttcatt atcgcgatat   1620
ccgttaagtt tgtatcgtag cggccgccat ggaaaagatt gtgctgctgt ttgctgtgat   1680
tagcctggtg aagtcagatc agatttgtat cggttaccat gccaataatt ctactaaaca   1740
ggtggataca attatggaaa agaacgtgac cgtgacacac gctcaggaca tcctggagag   1800
aactcataac gggaagctgt gcgatctgaa tggtgtgaaa cccctgatcc tgaaggactg   1860
ctctgtggca ggctggctgc tgggaaaccc catgtgtgat gagttcatca gagtgcctga   1920
atggtcctac attgtggaga gggctaaccc tgcaaatgat ctgtgctacc caggaaccct   1980
gaacgactat gaggaactga agcacctgct gagccgcatc aaccatttcg aaaagacact   2040
gatcatcccc cggagctcct ggcctaatca cgagactagc ctgggagtgt ccgcagcttg   2100
tccataccag ggagcatctt cattctttcg caacgtggtg tggctgatca agaaaaatga   2160
tgcctacccc accatcaaaa tctcatacaa caacacaaac cgggaagatc ttctgatcct   2220
gtggggcatc caccattcca acaatgcagc cgagcagact aacctgtaca aaaatcctga   2280
tacctatgtg tctgtgggga cttcaaccct gaaccagcgc ctggtgccaa agatcgccac   2340
tcggtcacaa gtgaatgggc agagtggtcg catggatttc ttttggacca tcctgaagcc   2400
aaacgacgct attcacttcg aaagcaacgg caattttatc gcccccgagt acgcttataa   2460
gattgtgaag aaaggagaca gtaccatcat gaaaagcgag atggaatacg ggcactgcaa   2520
cacaaagtgt cagactccta tcggtgccat taacagtagc atgccattcc acaatatcca   2580
tcccctgaca attggggagt gccccaagta tgtgaaatct aacaagctgg tgctggctac   2640
tggtctgaga aacagccccc tgagagagac ccggggcctg tttggagcaa ttgctgggtt   2700
tattgagggc ggatggcagg gtatggtgga tgggtggtac ggttatcacc attccaacga   2760
```

-continued

```
acaggggtct ggttacgctg cagataaaga gtccacacag aaggctattg acggagtgac   2820

taacaaagtg aacagcatca ttgacaagat gaatactcag ttcgaggcag tggggagaga   2880

atttaacaat ctggagagaa ggatcgaaaa cctgaataag aaaatggaag atggcttcct   2940

ggacgtgtgg acctacaacg cagagctgct ggtgctgatg gagaatgaaa ggacactgga   3000

ttttcacgac agcaacgtga aaaatctgta tgataaagtg agactgcagc tgagggacaa   3060

cgctaaagaa ctgggcaatg gatgtttcga gttttaccat aagtgcgata acgagtgtat   3120

ggaaagtgtg agaaatggca catacgacta tccaaaatat agcgaggaag caatcctgaa   3180

gagggaggaa attagcggcg tgaaactgga gtccatcgga acctaccaga tcctgtcaat   3240

ttatagtaca gtggcctcct ctctggcact ggccatcatt gtggctgggc tgtctctgtg   3300

gatgtgtagt aacgggagtc tgcagtgtag gatttgtatc tgagcggccg cctcgagttt   3360

ttattgacta gttaatcata agataaataa tatacagcat tgtaaccatc gtcatccgtt   3420

atacggggaa taatattacc atacagtatt attaaatttt cttacgaaga atatagatcg   3480

gtatttatcg ttagtttatt ttacatttat taattaaaca tgtctactat tacctgttat   3540

ggaaatgaca aatttagtta tataatttat gataaaatta agataataat aatgaaatca   3600

aataattatg taaatgctac tagattatgt gaattacgag gaagaaagtt tacgaactgg   3660

aaaaaattaa gtgaatctaa aatattagtc gataatgtaa aaaaaataaa tgataaaact   3720

aaccagttaa aaacggatat gattatatac gttaaggata ttgatcataa aggaagagat   3780

acttgcggtt actatgtaca ccaagatctg gtatcttcta tatcaaattg gatatctccg   3840

ttattcgccg ttaaggtaaa taaaattatt aactattata tatgtaatga atatgatata   3900

cgacttagcg aaatggaatc tgatatgaca gaagtaatag atgtagttga taaattagta   3960

ggaggataca atgatgaaat agcagaaata atatatttgt ttaataaatt tatagaaaaa   4020

tatattgcta acatatcgtt atcaactgaa ttatctagta tattaaataa ttttataaat   4080

tttaataaaa aatacaataa cgacataaaa gatattaaat ctttaattct tgatctgaaa   4140

aacacatcta taaaactaga taaaaagtta ttcgataaag ataataatga atcgaacgat   4200

gaaaaattgg aaacagaagt tgataagcta atttttttca tctaaatagt attattttat   4260

tgaagtacga agttttacgt tagataaata ataaaggtcg atttttattt tgttaaatat   4320

caaatatgtc attatctgat aaagatacaa aaacacacgg tgattatcaa ccatctaacg   4380

aacagatatt acaaaaaata cgtcggacta tggaaaacga agctgatagc ctcaatagaa   4440

gaagcattaa agaaattgtt gtagatgtta tgaagaattg ggatcatcct ctcaacgaag   4500

aaatagataa agttctaaac tggaaaaatg atacattaaa cgatttagat catctaaata   4560

cagatgataa tattaaggaa atcatacaat gtctgattag agaatttgcg tttaaaaaga   4620

tcaattctat tatgtatagt tatgctatgg taaaactcaa ttcagataac gaaacattga   4680

aagataaaat taaggattat tttatagaaa ctattcttaa agacaaacgt ggttataaac   4740

aaaagccatt accc                                                       4754
```

<210> SEQ ID NO 13
<211> LENGTH: 4754
<212> TYPE: DNA
<213> ORGANISM: artificial
<220> FEATURE:
<223> OTHER INFORMATION: Nucleotide sequence of donor plasmid pF8
H6p3Mut-HA H5N2
<220> FEATURE:
<221> NAME/KEY: Flanking Arms -continued
<222> LOCATION: (1)..(1429)
<220> FEATURE:
<221> NAME/KEY: H6 Promoter
<222> LOCATION: (1516)..(1639)
<220> FEATURE:
<221> NAME/KEY: Mut-HA H5N2
<222> LOCATION: (1649)..(3343)
<220> FEATURE:
<221> NAME/KEY: Flanking Arms
<222> LOCATION: (3379)..(4754)

<400> SEQUENCE: 13

```
gaccctttac aagaataaaa gaagaaacaa ctgtgaaata gtttataaat gtaattcgta     60
tgcagaaaac gataatatat tttggtatga gaaatctaaa ggagacatag tttgtataga    120
catgcgctct tccgatgaga tattcgatgc ttttctaatg tatcatatag ctacaagata    180
tgcctatcat gatgatgata tatatctaca aatagtgtta tattattcta ataatcaaaa    240
tgttatatct tatattacga aaaataaata cgttaagtat ataagaaata aaactagaga    300
cgatattcat aaagtaaaaa tattagctct agaagacttt acaacggaag aaatatattg    360
ttggattagt aatatataac agcgtagctg cacggttttg atcattttcc aacaatataa    420
accaatgaag gaggacgact catcaaacat aaataacatt cacggaaaat attcagtatc    480
agatttatca caagatgatt atgttattga atgtatagac ggatcttttg attcgatcaa    540
gtatagagat ataaaggtta taataatgaa gaataacggt tacgttaatt gtagtaaatt    600
atgtaaaatg cggaataaat acttttctag atggttgcgt ctttctactt ctaaagcatt    660
attagacatt tacaataata agtcagtaga taatgctatt gttaaagtct atggtaaagg    720
taagaaactt attataacag gattttatct caaacaaaat atgatacgtt atgttattga    780
gtggataggg gatgatttta caaacgatat atacaaaatg attaatttct ataatgcgtt    840
attcggtaac gatgaattaa aaatagtatc ctgtgaaaac actctatgcc cgtttataga    900
acttggtaga tgctattatg gtaaaaaatg taagtatata cacggagatc aatgtgatat    960
ctgtggtcta tatatactac accctaccga tattaaccaa cgagtttctc acaagaaaac   1020
ttgtttagta gatagagatt ctttgattgt gtttaaaaga agtaccagta aaaagtgtgg   1080
catatgcata gaagaaataa acaaaaaaca tatttccgaa cagtattttg gaattctccc   1140
aagttgtaaa catatttttt gcctatcatg tataagacgt tgggcagata ctaccagaaa   1200
tacagatact gaaaatacgt gtcctgaatg tagaatagtt tttcctttca taatacccag   1260
taggtattgg atagataata aatatgataa aaaaatatta tataatagat ataagaaaat   1320
gatttttaca aaaataccta taagaacaat aaaaatataa ttacatttac ggaaaatagc   1380
tggttttagt ttaccaactt agagtaatta tcatattgaa tctatattgc taattagcta   1440
ataaaaaccc gggttaatta attagtcatc aggcagggcg agaacgagac tatctgctcg   1500
ttaattaatt agagcttctt tattctatac ttaaaaagtg aaaataaata caaaggttct   1560
tgagggttgt gttaaattga aagcgagaaa taatcataaa ttatttcatt atcgcgatat   1620
ccgttaagtt tgtatcgtag cggccgccat ggaaaagatt gtgctgctgt ttgctgtgat   1680
ttccctggtg aagtccgacc agatttgtat tggctaccac gctaataact caaccaaaca   1740
ggtggataca attatggaaa agaacgtgac cgtgacacac gctcaggaca tcctggagag   1800
aactcataac gggaagctgt gcgatctgaa tggtgtgaaa cccctgatcc tgaaggactg   1860
ctcagtggca ggctggctgc tgggaaaccc catgtgtgat gagttcatca gagtgcctga   1920
atggtcctac attgtggaga gggctaaccc tgcaaatgat ctgtgctacc caggaaccct   1980
```

-continued

```
gaacgactat gaggaactga agcacctgct gagtcgcatc aaccatttcg aaaagacact   2040
gatcatcccc cggaacagct ggcctaatca cgagacttca ctgggcgtga gtgccgcttg   2100
tccataccag ggagcaagct ccttctttcg caacgtggtg tggctgatca agaaaaacaa   2160
tgcctacccc accatcaaaa tctcctacaa caacacaaat cgggaagatc ttctgatcct   2220
gtggggcatc caccattcta acaatgcagc cgagcagact aacctgtaca aaaatcctga   2280
cacctatgtg agcgtgggga cttccaccct gaaccagcgc ctggtgccaa agatcgccac   2340
tcggtctcag gtgaacgggc agaatggtcg catggatttc ttttggacca tcctgaagcc   2400
aaatgacgct attcacttcg aatccaacgg caattttatc gcccccgagt acgcttataa   2460
gattgtgaag aaaggagact ctaccatcat gaaatcagag atggaatacg ggcactgcaa   2520
cacaaagtgt cagactccta tcggtgccat taactcttca atgccattcc acaatatcca   2580
tcccctgaca attggggagt gccccaagta tgtgaaatca aacaagctgg tgctggctac   2640
tggtctgagg aatagtcctc tgcgcgaaac ccggggcctg tttggagcaa ttgctggttt   2700
tattgagggc ggatggcagg gtatggtgga tgggtggtac ggttatcacc atagtaacga   2760
acaggggagc ggttacgctg cagataaaga gtctacacag aaggctattg acggagtgac   2820
taacaaagtg aacagcatca ttgacaagat gaacactcag ttcgaggcag tggggagaga   2880
atttaacaat ctggagagaa ggatcgaaaa cctgaataag aaaatggaag atggcttcct   2940
ggacgtgtgg acctacaacg cagagctgct ggtgctgatg gagaatgaaa ggacactgga   3000
ttttcacgac agcaacgtga aaatctgta tgataaagtg agactgcagc tgagggacaa   3060
cgctaaagaa ctgggcaatg gatgtttcga gttttaccat aagtgcgata acgagtgtat   3120
ggaaagcgtg agaaatggca catacgacta tccaaaatat tccgaggaag caatcctgaa   3180
gagggaggaa atttccggcg tgaaactgga gtctatcgga acctaccaga tcctgtccat   3240
ttattctaca gtggccagta gcctggcact ggccatcatt gtggctggtc tgtctctgtg   3300
gatgtgttca aacggtagtc tgcagtgtag aatctgtatc tgagcggccg cctcgagttt   3360
ttattgacta gttaatcata agataaataa tatacagcat tgtaaccatc gtcatccgtt   3420
atacggggaa taatattacc atacagtatt attaaatttt cttacgaaga atatagatcg   3480
gtatttatcg ttagtttatt ttacatttat taattaaaca tgtctactat tacctgttat   3540
ggaaatgaca aatttagtta tataatttat gataaaatta agataataat aatgaaatca   3600
aataattatg taaatgctac tagattatgt gaattacgag gaagaaagtt tacgaactgg   3660
aaaaaattaa gtgaatctaa aatattagtc gataatgtaa aaaaaataaa tgataaaact   3720
aaccagttaa aaacggatat gattatatac gttaaggata ttgatcataa aggaagagat   3780
acttgcggtt actatgtaca ccaagatctg gtatcttcta tatcaaattg gatatctccg   3840
ttattcgccg ttaaggtaaa taaaattatt aactattata tatgtaatga atatgatata   3900
cgacttagcg aaatggaatc tgatatgaca gaagtaatag atgtagttga taaattagta   3960
ggaggataca atgatgaaat agcagaaata atatatttgt ttaataaatt tatagaaaaa   4020
tatattgcta acatatcgtt atcaactgaa ttatctagta tattaaataa ttttataaat   4080
tttaataaaa aatacaataa cgacataaaa gatattaaat ctttaattct tgatctgaaa   4140
aacacatcta taaaactaga taaaaagtta ttcgataaag ataataatga atcgaacgat   4200
gaaaaattgg aaacagaagt tgataagcta atttttttca tctaaatagt attattttat   4260
tgaagtacga agttttacgt tagataaata ataaaggtcg atttttattt tgttaaatat   4320
caaatatgtc attatctgat aaagatacaa aaacacacgg tgattatcaa ccatctaacg   4380
```

aacagatatt acaaaaaata cgtcggacta tggaaaacga agctgatagc ctcaatagaa 4440
gaagcattaa agaaattgtt gtagatgtta tgaagaattg ggatcatcct ctcaacgaag 4500
aaatagataa agttctaaac tggaaaaatg atacattaaa cgatttagat catctaaata 4560
cagatgataa tattaaggaa atcatacaat gtctgattag agaatttgcg tttaaaaaga 4620
tcaattctat tatgtatagt tatgctatgg taaaactcaa ttcagataac gaaacattga 4680
aagataaaat taaggattat tttatagaaa ctattcttaa agacaaacgt ggttataaac 4740
aaaagccatt accc 4754

<210> SEQ ID NO 14
<211> LENGTH: 7
<212> TYPE: PRT
<213> ORGANISM: artificial
<220> FEATURE:
<223> OTHER INFORMATION: highly pathogenic HA cleavage site

<400> SEQUENCE: 14

Arg Glu Arg Arg Arg Lys Arg
1 5

<210> SEQ ID NO 15
<211> LENGTH: 4
<212> TYPE: PRT
<213> ORGANISM: artificial
<220> FEATURE:
<223> OTHER INFORMATION: low pathogenic HA cleavage site

<400> SEQUENCE: 15

Arg Glu Thr Arg
1

<210> SEQ ID NO 16
<211> LENGTH: 1412
<212> TYPE: DNA
<213> ORGANISM: artificial
<220> FEATURE:
<223> OTHER INFORMATION: mCMV promoter

<400> SEQUENCE: 16
gaattcacta gtggatcccc caactccgcc cgttttatga ctagaaccaa tagtttttaa 60
tgccaaatgc actgaaatcc cctaatttgc aaagccaaac gccccctatg tgagtaatac 120
ggggactttt tacccaattt cccaagcgga aagcccccta atacactcat atggcatatg 180
aatcagcacg gtcatgcact ctaatggcgg cccataggga ctttccacat agggggcgtt 240
caccatttcc cagcataggg gtggtgactc aatggccttt acccaagtac attgggtcaa 300
tgggaggtaa gccaatgggt ttttcccatt actggcaagc acactgagtc aaatgggact 360
ttccactggg ttttgcccaa gtacattggg tcaatgggag gtgagccaat gggaaaaacc 420
cattgctgcc aagtacactg actcaatagg gactttccaa tgggtttttc cattgttggc 480
aagcatataa ggtcaatgtg ggtgagtcaa tagggacttt ccattgtatt ctgcccagta 540
cataaggtca ataggggtg aatcaacagg aaagtcccat tggagccaag tacactgcgt 600
caatagggac tttccattgg gttttgccca gtacataagg tcaatagggg atgagtcaat 660
gggaaaaacc cattggagcc aagtacactg actcaatagg gactttccat tgggttttgc 720
ccagtacata aggtcaatag ggggtgagtc aacaggaaag tcccattgga gccaagtaca 780
ttgagtcaat agggactttc caatgggttt tgcccagtac ataaggtcaa tgggaggtaa 840

```
gccaatgggt ttttcccatt actggcacgt atactgagtc attagggact ttccaatggg    900

ttttgcccag tacataaggt caataggggt gaatcaacag gaaagtccca ttggagccaa    960

gtacactgag tcaataggga ctttccattg ggttttgccc agtacaaaag gtcaataggg   1020

ggtgagtcaa tgggtttttc ccattattgg cacgtacata aggtcaatag ggtgagtca   1080

ttgggttttt ccagccaatt taattaaaac gccatgtact ttcccaccat tgacgtcaat   1140

gggctattga aactaatgca acgtgacctt taaacggtac tttcccatag ctgattaatg   1200

ggaaagtacc gttctcgagc caatacacgt caatgggaag tgaaagggca gccaaaacgt   1260

aacaccgccc cggttttccc ctggaaattc catattggca cgcattctat tggctgagct   1320

gcgttctacg tgggtataag aggcgcgacc agcgtcggta ccgtcgcagt cttcggtctg   1380

accaccgtag aacgcagagc tcctcgctgc ag                                 1412


<210> SEQ ID NO 17
<211> LENGTH: 1692
<212> TYPE: DNA
<213> ORGANISM: artificial
<220> FEATURE:
<223> OTHER INFORMATION: DNA encoding mutant H5N2 HA in plasmid pCD046-
      H5N2 HA (rHVT510), wild-type

<400> SEQUENCE: 17

atggagaaaa tagtgcttct tttgcagtg attagccttg ttaaaagtga tcagatttgc      60

attggttacc atgcaaacaa ctcaacaaag caggttgaca cgataatgga gaaaaacgtc    120

actgttacac atgcccaaga catactggaa aggacacaca acgggaagct ctgcgatctt    180

aatggagtga aacccctgat tctaaaggat tgtagcgtag ctgggtggct ccttggaaat    240

ccaatgtgcg acgagttcat cagggtaccg gaatggtctt acatcgtgga gagggctaac    300

ccagccaacg acctctgtta cccagggacc ctcaatgact atgaggaact gaaacaccta    360

ttgagcagaa taaatcattt tgagaaaact ctgatcatcc ccaggagttc ttggcccaat    420

catgaaacat cattaggggt gagcgcagca tgtccatacc agggagcatc ctcatttttc    480

agaaatgtgg tatggctcat caaaaagaac gatgcatacc cgacaataaa gataagctac    540

aataatacca atcgggaaga tcttttgata ctgtggggga ttcatcattc caacaatgca    600

gcagagcaga caaatctcta taaaaaccca gacacttatg tttccgttgg gacatcaaca    660

ttaaaccaga gattggtgcc aaaaatagct actagatccc aagtaaacgg gcagagtgga    720

agaatggatt tcttctggac aattttaaaa ccgaatgatg caatccactt tgagagtaat    780

ggaaatttca ttgctccaga atatgcatac aaaattgtca agaaagggga ctcaacaatt    840

atgaaaagtg aaatggagta tggccactgc aacaccaaat gtcaaactcc aatagggcg    900

ataaactcta gcatgccatt ccacaatata caccctctca ccatcgggga atgccccaaa    960

tacgtgaagt caaacaaatt agtccttgcg actgggctca gaaatagtcc tctaagagaa   1020

acgagaggac tatttggagc tatagcaggg tttatagagg gaggatggca gggaatggta   1080

gacggttggt atgggtatca tcatagcaat gagcagggga gtgggtacgc tgcagacaaa   1140

gaatcaaccc aaaaggcaat agatggagtt accaataagg tcaactcaat cattgacaaa   1200

atgaacactc aatttgaggc cgttggaagg gaatttaata acttagaaag gagaatagag   1260

aatttaaaca agaaaatgga agacggattc ctagatgtct ggacttataa tgctgaactt   1320

ttagttctca tggaaaatga gagaactcta gatttccatg actcaaatgt caagaacctt   1380

tacgacaaag tccgactaca gcttagggat aatgcaaagg agctgggtaa tggttgtttc   1440
```

-continued

```
gagttctatc ataaatgtga taacgaatgt atggagagcg taagaaatgg gacgtatgac   1500

taccctaagt attcagaaga agcaatatta aaaagagaag aaataagcgg agtgaaatta   1560

gaatcaatag gaacttacca gatactgtca atttattcaa cagtggcgag ttccctagca   1620

ctggcaatca tagtggctgg tctatcttta tggatgtgct ctaatgggtc gttacaatgc   1680

agaatttgca tc                                                       1692
```

<210> SEQ ID NO 18
<211> LENGTH: 218
<212> TYPE: DNA
<213> ORGANISM: artificial
<220> FEATURE:
<223> OTHER INFORMATION: SV40 PolyA tail

<400> SEQUENCE: 18

```
ggggatccag acatgataag atacattgat gagtttggac aaaccacaac tagaatgcag     60

tgaaaaaaat gctttatttg tgaaatttgt gatgctattg ctttatttgt aaccattata    120

agctgcaata aacaagttaa caacaacaat tgcattcatt ttatgtttca ggttcagggg    180

gaggtgtggg aggtttttc ggatcctcta gagtcgac                             218
```

<210> SEQ ID NO 19
<211> LENGTH: 5415
<212> TYPE: DNA
<213> ORGANISM: artificial
<220> FEATURE:
<223> OTHER INFORMATION: Nucleotide sequence of donor plasmid pCD046-
      H5N2 HA
<220> FEATURE:
<221> NAME/KEY: Recombination flanking arm
<222> LOCATION: (1)..(1241)
<220> FEATURE:
<221> NAME/KEY: mCMV promoter
<222> LOCATION: (1242)..(2653)
<220> FEATURE:
<221> NAME/KEY: H5N2 HA
<222> LOCATION: (2663)..(4357)
<220> FEATURE:
<221> NAME/KEY: SV40 polyA
<222> LOCATION: (4366)..(4583)
<220> FEATURE:
<221> NAME/KEY: Recombination flanking arm
<222> LOCATION: (4584)..(5415)

<400> SEQUENCE: 19

```
gagctcaggg tatgatactc agctgttatt gtggccgacc aggaggactc caatgcttag     60

cattcataag aacgctagag atgctattta acgatgtgct gtcgtctaaa gaatttgtgc    120

atttagcctt taaatgtaaa accaatgacg cattcactac gctcgtgcgt gcaatttctg    180

ggccagggta tgcatattcc ataacagaaa tcgacacttg agaagaggat ctgactgttt    240

gggataaagg tcgtttgggt ctgtcctagc gatataattt atatgacgat atacattaaa    300

catctgtgtg cagtacttag gtatttaatc atgtcgatga aatgttatgt gtaaatatcg    360

gacaatatag ataacgggca cgctgctatt gtaacgtgcg cccgcgcgct agtgctgact    420

aatagtgtgg atgatgtata cagtatatta caaacggaaa tgatacgtaa taaattatgt    480

actcttattg atttataaaa acatacatgc agtgttgcta tgtcacataa ttagcctcgc    540

ccgtctacgc tccactgaag ataatgggct cccgctgttc aaaaaaatca gcgtgcgtcg    600

ataagacttt ggtgcagtct cttcggggtc gcaatttaga tttgccgcat ggagggtatc    660

tggggatttt tgccaatgct ggagcgacga ctgtacgatt cgtcccatcg ggatctagca    720

gaccaatgat gttgacacac atcggccatg catgtacgga cggtctattg cgcgagtttg    780
```

```
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaaaga aaaatcggat ggttcaatta ggacatgcat ggattctgtg cgcataaacc   1020
ataaccgcag cactgttggg cacttcggta actcaaatgc gaagcgttgc acgtctgcga   1080
taactacgcc tactatgcac attgttactc ctgcatctta aaaatatatc ctgtagtaat   1140
tttcacagca atgtcataac atcatctcgc taaagaatga cctgggattg gagaagtaat   1200
gaatatttgc aaccaatgca ttgaataaac taacattaaa cgaattcact agtggatccc   1260
ccaactccgc ccgttttatg actagaacca atagttttta atgccaaatg cactgaaatc   1320
ccctaatttg caaagccaaa cgccccctat gtgagtaata cggggacttt ttacccaatt   1380
tcccaagcgg aaagccccct aatacactca tatggcatat gaatcagcac ggtcatgcac   1440
tctaatggcg gcccataggg actttccaca tagggggcgt tcaccatttc ccagcatagg   1500
ggtggtgact caatggcctt tacccaagta cattgggtca atgggaggta agccaatggg   1560
tttttcccat tactggcaag cacactgagt caaatgggac tttccactgg gttttgccca   1620
agtacattgg gtcaatggga ggtgagccaa tgggaaaaac ccattgctgc caagtacact   1680
gactcaatag ggactttcca atgggttttt ccattgttgg caagcatata aggtcaatgt   1740
gggtgagtca atagggactt tccattgtat tctgcccagt acataaggtc aataggggt    1800
gaatcaacag gaaagtccca ttggagccaa gtacactgcg tcaataggga ctttccattg   1860
ggttttgccc agtacataag gtcaataggg gatgagtcaa tgggaaaaac ccattggagc   1920
caagtacact gactcaatag ggactttcca ttgggttttg cccagtacat aaggtcaata   1980
gggggtgagt caacaggaaa gtcccattgg agccaagtac attgagtcaa tagggacttt   2040
ccaatgggtt ttgcccagta cataaggtca atgggaggta agccaatggg tttttcccat   2100
tactggcacg tatactgagt cattagggac tttccaatgg gttttgccca gtacataagg   2160
tcaatagggg tgaatcaaca ggaaagtccc attggagcca agtacactga gtcaataggg   2220
actttccatt gggttttgcc cagtacaaaa ggtcaatagg gggtgagtca atgggttttt   2280
cccattattg gcacgtacat aaggtcaata ggggtgagtc attgggtttt tccagccaat   2340
ttaattaaaa cgccatgtac tttcccacca ttgacgtcaa tgggctattg aaactaatgc   2400
aacgtgacct ttaaacggta ctttcccata gctgattaat gggaaagtac cgttctcgag   2460
ccaatacacg tcaatgggaa gtgaaagggc agccaaaacg taacaccgcc ccggttttcc   2520
cctggaaatt ccatattggc acgcattcta ttggctgagc tgcgttctac gtgggtataa   2580
gaggcgcgac cagcgtcggt accgtcgcag tcttcggtct gaccaccgta gaacgcagag   2640
ctcctcgctg caggcggccg ccatggagaa aatagtgctt ctttttgcag tgattagcct   2700
tgttaaaagt gatcagattt gcattggtta ccatgcaaac aactcaacaa agcaggttga   2760
cacgataatg gagaaaaacg tcactgttac acatgcccaa gacatactgg aaaggacaca   2820
caacgggaag ctctgcgatc ttaatggagt gaaacccctg attctaaagg attgtagcgt   2880
agctgggtgg ctccttggaa atccaatgtg cgacgagttc atcagggtac cggaatggtc   2940
ttacatcgtg gagagggcta acccagccaa cgacctctgt tacccaggga ccctcaatga   3000
ctatgaggaa ctgaaacacc tattgagcag aataaatcat tttgagaaaa ctctgatcat   3060
ccccaggagt tcttggccca atcatgaaac atcattaggg gtgagcgcag catgtccata   3120
```

-continued

```
ccagggagca tcctcatttt tcagaaatgt ggtatggctc atcaaaaaga acgatgcata   3180
cccgacaata aagataagct acaataatac caatcgggaa gatcttttga tactgtgggg   3240
gattcatcat tccaacaatg cagcagagca gacaaatctc tataaaaacc cagacactta   3300
tgtttccgtt gggacatcaa cattaaacca gagattggtg ccaaaaatag ctactagatc   3360
ccaagtaaac gggcagagtg gaagaatgga tttcttctgg acaattttaa aaccgaatga   3420
tgcaatccac tttgagagta atggaaattt cattgctcca gaatatgcat acaaaattgt   3480
caagaaaggg gactcaacaa ttatgaaaag tgaaatggag tatggccact gcaacaccaa   3540
atgtcaaact ccaatagggg cgataaactc tagcatgcca ttccacaata tacaccctct   3600
caccatcggg gaatgcccca aatacgtgaa gtcaaacaaa ttagtccttg cgactgggct   3660
cagaaatagt cctctaagag aaacgagagg actatttgga gctatagcag ggtttataga   3720
gggaggatgg cagggaatgg tagacggttg gtatgggtat catcatagca atgagcaggg   3780
gagtgggtac gctgcagaca aagaatcaac ccaaaaggca atagatggag ttaccaataa   3840
ggtcaactca atcattgaca aaatgaacac tcaatttgag gccgttggaa gggaatttaa   3900
taacttagaa aggagaatag agaatttaaa caagaaaatg gaagacggat tcctagatgt   3960
ctggacttat aatgctgaac ttttagttct catggaaaat gagagaactc tagatttcca   4020
tgactcaaat gtcaagaacc tttacgacaa agtccgacta cagcttaggg ataatgcaaa   4080
ggagctgggt aatggttgtt tcgagttcta tcataaatgt gataacgaat gtatggagag   4140
cgtaagaaat gggacgtatg actaccctaa gtattcagaa gaagcaatat taaaaagaga   4200
agaaataagc ggagtgaaat tagaatcaat aggaacttac cagatactgt caatttattc   4260
aacagtggcg agttccctag cactggcaat catagtggct ggtctatctt tatggatgtg   4320
ctctaatggg tcgttacaat gcagaatttg catctaagcg gccgcgggga tccagacatg   4380
ataagataca ttgatgagtt tggacaaacc acaactagaa tgcagtgaaa aaaatgcttt   4440
atttgtgaaa tttgtgatgc tattgcttta tttgtaacca ttataagctg caataaacaa   4500
gttaacaaca acaattgcat tcattttatg tttcaggttc agggggaggt gtgggaggtt   4560
ttttcggatc ctctagagtc gacaattatt ttatttaata acatatagcc caaagacctc   4620
tatgaacatt tagtttcccg tatactcaac ggcgcgtgta cacacgcatc tctttgcata   4680
gcgatgaagt ttgttcggca gcagaaaatg cagatatcca acaatctgga gaaaacttat   4740
catcacagtg gcagtggaaa catacccccct ctatattcat ggtataatta tcgtctacag   4800
cgtccaggat agtggcgtga gaaaatggag atctgcagcc ctcctttcca tggcatgccg   4860
ctttattgtt cattaaacgc acaatggtct caacgccaga tatgggcata gattctgaag   4920
aacccgttga caatccgaag aagaaggcgt gcaggtcttt ggaagactcg cacgttggtc   4980
ttataatgta tgatcgagat gtcaccctaa tgccacatgg tacaggctta tcgcggtcat   5040
ggcgatcgga cttgtaattt gcaacgatgg gcaaaggatc gacgacatgc caaacattct   5100
gaacccgtag agatgttaac gatgacgagg atgaatatcc catgctcgct gccatagtat   5160
caagtacacc gcgaataagg acgcgtccaa catcgttata tgcacacaat gggctacacg   5220
tgactaacac ccccgaatat tagtcatatg tgagtttcag tctggctccc atatagcctg   5280
tagactattt gtggtttaag tgtgaacgag gcgctgtgaa cgagactcgg gccgattgta   5340
agaacaagca aatgcacttt ccatttaaca agaagtgtag agagaatact caacctcttt   5400
ggatgtatcc tcgag                                                    5415
```

<210> SEQ ID NO 20
<211> LENGTH: 564
<212> TYPE: PRT
<213> ORGANISM: artificial
<220> FEATURE:
<223> OTHER INFORMATION: ALT19477 with modified low pathogenic cleave site hemagglutinin [Influenza A virus (A/wood/Oregon/AH0007263/2015(H5N2))]

<400> SEQUENCE: 20

```
Met Glu Lys Ile Val Leu Leu Phe Ala Val Ile Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Ile Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Ser Ser Trp Pro Asn His Glu Thr Ser
    130                 135                 140

Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365
```

```
Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 21
<211> LENGTH: 564
<212> TYPE: PRT
<213> ORGANISM: artificial
<220> FEATURE:
<223> OTHER INFORMATION: ALT19381 with modified low pathogenic  cleave
      site hemagglutinin [Influenza A virus
      A/mallard/Idaho/AH0007413/2015(H5N2))]

<400> SEQUENCE: 21

Met Glu Lys Ile Val Leu Leu Phe Ala Val Ile Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Ser Ser Trp Pro Asn His Glu Thr Ser
    130                 135                 140

Leu Gly Val Ser Ala Ala Cys Pro Tyr Gln Gly Ala Ser Ser Phe Phe
```

-continued

```
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Lys Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 22
<211> LENGTH: 564
<212> TYPE: PRT
<213> ORGANISM: artificial
<220> FEATURE:
<223> OTHER INFORMATION: AKH14518 with modified low pathogenic cleave site hemagglutinin [Influenza A virusA/turkey/Minnesota/7172-1/2015(H5N2))]

<400> SEQUENCE: 22

```
Met Glu Glu Ile Val Leu Leu Phe Ala Val Ile Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Ser Ser Trp Pro Asn His Glu Thr Ser
    130                 135                 140

Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
```

```
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 23
<211> LENGTH: 564
<212> TYPE: PRT
<213> ORGANISM: artificial
<220> FEATURE:
<223> OTHER INFORMATION: ALH21333 with modified low pathogenic  cleave
      site hemagglutinin [Influenza A virus (A/chicken/Montana/15-
      010559-1/2015(H5N2))]

<400> SEQUENCE: 23

Met Glu Lys Ile Val Leu Leu Phe Ala Val Val Asn Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Ser Ser Trp Pro Asn His Glu Thr Ser
    130                 135                 140
```

-continued

```
Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 24
<211> LENGTH: 564
<212> TYPE: PRT
<213> ORGANISM: artificial
<220> FEATURE:
<223> OTHER INFORMATION: ALT19525 with modified low pathogenic cleave site hemagglutinin [Influenza virus (A/mallard/Oregon/AH0003952/2015(H5N2))]

<400> SEQUENCE: 24

```
Met Glu Lys Ile Val Leu Leu Phe Ala Val Val Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Ser Ser Trp Pro Asn His Glu Thr Ser
    130                 135                 140

Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350
```

```
Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Phe Leu Trp Met Cys Ser Asn Gly Ser Leu Gln Cys
545                 550                 555                 560

Arg Ile Cys Ile


<210> SEQ ID NO 25
<211> LENGTH: 564
<212> TYPE: PRT
<213> ORGANISM: artificial
<220> FEATURE:
<223> OTHER INFORMATION: AKN08877 with modified low pathogenic cleave
      site hemagglutinin [Influenza A virus (A/chicken/Iowa/14589-
      1/2015(H5N2))]

<400> SEQUENCE: 25

Met Glu Lys Ile Val Leu Pro Phe Ala Val Ile Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Ile Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Arg Ser Ser Trp Pro Asn His Glu Thr Ser
    130                 135                 140
```

-continued

```
Leu Gly Val Ser Ala Ala Cys Pro Tyr Gln Gly Ala Pro Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Lys Tyr Ser Glu Glu Ala Ile Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560
```

Arg Ile Cys Ile

<210> SEQ ID NO 26
<211> LENGTH: 564
<212> TYPE: PRT
<213> ORGANISM: artificial
<220> FEATURE:
<223> OTHER INFORMATION: AJS16153 with modified low pathogenic cleave site hemagglutinin [Influenza A virus (A/duck/EasternChina/S0131/2014(H5N2))]

<400> SEQUENCE: 26

Met Glu Lys Ile Val Leu Leu Leu Ala Ile Val Ser Leu Val Lys Ser
1 5 10 15

Asp Gln Ile Cys Ile Gly Tyr His Ala Asn Asn Ser Thr Lys Gln Val
20 25 30

Asp Thr Ile Met Glu Lys Asn Val Thr Val Thr His Ala Gln Asp Ile
35 40 45

Leu Glu Lys Thr His Asn Gly Lys Leu Cys Asp Leu Asn Gly Val Lys
50 55 60

Pro Leu Ile Leu Lys Asp Cys Ser Val Ala Gly Trp Leu Leu Gly Asn
65 70 75 80

Pro Met Cys Asp Glu Phe Ile Arg Val Pro Glu Trp Ser Tyr Ile Val
85 90 95

Glu Arg Ala Asn Pro Ala Asn Asp Leu Cys Tyr Pro Gly Thr Leu Asn
100 105 110

Asp Tyr Glu Glu Leu Lys His Leu Leu Ser Arg Ile Asn His Phe Glu
115 120 125

Lys Thr Leu Ile Ile Pro Lys Ser Ser Trp Pro Asn His Glu Thr Ser
130 135 140

Leu Gly Val Ser Ala Ala Cys Pro Tyr Gln Gly Ala Ser Ser Phe Phe
145 150 155 160

Arg Asn Val Val Trp Leu Ile Lys Lys Asn Asp Ala Tyr Pro Thr Ile
165 170 175

Lys Ile Ser Tyr Asn Asn Thr Asn Arg Glu Asp Leu Leu Ile Leu Trp
180 185 190

Gly Ile His His Ser Asn Asn Ala Ala Glu Gln Thr Asn Leu Tyr Lys
195 200 205

Asn Pro Asp Thr Tyr Val Ser Val Gly Thr Ser Thr Leu Asn Gln Arg
210 215 220

Leu Val Pro Lys Ile Ala Thr Arg Ser Gln Val Asn Gly Gln Arg Gly
225 230 235 240

Arg Met Asp Phe Phe Trp Thr Ile Leu Lys Pro Asn Asp Ala Ile His
245 250 255

Phe Glu Ser Asn Gly Asn Phe Ile Ala Pro Glu Tyr Ala Tyr Lys Ile
260 265 270

Val Lys Lys Gly Asp Ser Thr Ile Met Lys Ser Glu Val Glu Tyr Gly
275 280 285

His Cys Asn Thr Lys Cys Gln Thr Pro Ile Gly Ala Ile Asn Ser Ser
290 295 300

Met Pro Phe His Asn Ile His Pro Leu Thr Ile Gly Glu Cys Pro Lys
305 310 315 320

Tyr Val Lys Ser Asn Lys Leu Val Leu Ala Thr Gly Leu Arg Asn Ser
325 330 335

Pro Leu Arg Glu Thr Arg Gly Leu Phe Gly Ala Ile Ala Gly Phe Ile
340 345 350

```
Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Val Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 27
<211> LENGTH: 564
<212> TYPE: PRT
<213> ORGANISM: artificial
<220> FEATURE:
<223> OTHER INFORMATION: ALP30284 with modified low pathogenic cleave
      site hemagglutinin [Influenza A virus
      (A/duck/Zhejiang/727041/2014(H5N2))]

<400> SEQUENCE: 27

Met Glu Lys Ile Val Leu Leu Leu Ala Val Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Lys Ser Ser Trp Pro Asn His Glu Thr Ser
```

-continued

```
    130                 135                 140

Leu Gly Val Ser Ala Ala Cys Pro Tyr Gln Gly Met Pro Ser Phe Phe
145                 150                 155                 160

Arg Asn Val Val Trp Leu Thr Lys Lys Asn Asp Ala Tyr Pro Thr Ile
                165                 170                 175

Lys Met Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Thr Thr Tyr Val Ser Val Gly Thr Ser Thr Leu Asn Gln Arg
    210                 215                 220

Leu Val Pro Lys Ile Ala Thr Arg Ser Gln Val Asn Gly Gln Arg Gly
225                 230                 235                 240

Arg Met Asp Phe Phe Trp Thr Ile Leu Lys Pro Lys Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Ile Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Arg Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560
```

Arg Ile Cys Ile

<210> SEQ ID NO 28
<211> LENGTH: 564
<212> TYPE: PRT
<213> ORGANISM: artificial
<220> FEATURE:
<223> OTHER INFORMATION: ALP30234 with modified low pathogenic cleave site hemagglutinin [Influenza A virus (A/chicken/Zhejiang/727079/2014(H5N2))]

<400> SEQUENCE: 28

```
Met Glu Lys Ile Val Leu Leu Leu Ala Val Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125

Lys Thr Leu Ile Ile Pro Lys Ser Ser Trp Pro Asn His Glu Thr Ser
    130                 135                 140

Leu Gly Val Ser Ala Ala Cys Pro Tyr Gln Gly Met Pro Ser Phe Phe
145                 150                 155                 160

Arg Asn Val Val Trp Leu Thr Lys Lys Asn Asp Ala Tyr Pro Thr Ile
                165                 170                 175

Lys Met Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Thr Thr Tyr Val Ser Val Gly Thr Ser Thr Leu Asn Gln Arg
    210                 215                 220

Leu Val Pro Lys Ile Ala Thr Arg Ser Gln Val Asn Gly Gln Arg Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
```

-continued

```
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Arg Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr Pro Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Ile
    530                 535                 540

Val Ala Gly Leu Ser Leu Trp Met Cys Ser Asn Gly Ser Leu Gln Cys
545                 550                 555                 560

Arg Ile Cys Ile
```